United States Patent
Mellem et al.

(10) Patent No.: US 11,289,187 B2
(45) Date of Patent: *Mar. 29, 2022

(54) MULTIMODAL BIOMARKERS PREDICTIVE OF TRANSDIAGNOSTIC SYMPTOM SEVERITY

(71) Applicant: Blackthorn Therapeutics, Inc., San Francisco, CA (US)

(72) Inventors: Monika Sharma Mellem, San Francisco, CA (US); Yuelu Liu, San Francisco, CA (US); Parvez Ahammad, San Francisco, CA (US); Humberto Andres Gonzalez Cabezas, San Francisco, CA (US); Matthew Kollada, San Francisco, CA (US)

(73) Assignee: BLACKTHORN THERAPEUTICS, INC., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/270,780

(22) PCT Filed: Aug. 29, 2019

(86) PCT No.: PCT/US2019/048809
§ 371 (c)(1),
(2) Date: Feb. 23, 2021

(87) PCT Pub. No.: WO2020/047253
PCT Pub. Date: May 3, 2020

(65) Prior Publication Data
US 2021/0358594 A1    Nov. 18, 2021

Related U.S. Application Data

(60) Provisional application No. 62/840,178, filed on Apr. 29, 2019, provisional application No. 62/726,009, filed on Aug. 31, 2018.

(51) Int. Cl.
*G16H 20/70* (2018.01)
*G16H 10/20* (2018.01)
(Continued)

(52) U.S. Cl.
CPC .......... *G16H 20/70* (2018.01); *G06T 7/0012* (2013.01); *G16H 10/20* (2018.01); *G16H 50/20* (2018.01);
(Continued)

(58) Field of Classification Search
CPC ...................................................... G16H 20/70
See application file for complete search history.

(56) References Cited

U.S. PATENT DOCUMENTS

2009/0240522 A1* 9/2009 Handal ................. G16H 40/67
705/2
2018/0310870 A1* 11/2018 Givon ................... G16H 50/20

FOREIGN PATENT DOCUMENTS

| AU | 2003/204909 B2 | 1/2004 |
| CA | 2715825 A1 | 8/2009 |
| WO | 2018/074996 A1 | 4/2018 |

OTHER PUBLICATIONS

International Search Report and Written Opinion in International Application No. PCT/US2019/48809, dated Jan. 7, 2020 (11 pages).

* cited by examiner

Primary Examiner — Reginald R Reyes
(74) Attorney, Agent, or Firm — Nixon Peabody LLP

(57) ABSTRACT

The method for evaluating mental health of a patient includes displaying a series of inquiries from mental health questionnaires on a display device. Each inquiry of the series of inquiries includes text and a set of answers. A series of selections is received from a user interface. Each selection of the series of selections is representative of an answer of the set of answers for each corresponding inquiry in the
(Continued)

series of inquiries. Unprocessed MRI data are received. The unprocessed MRI data correspond to a set of MRI images of a biological structure associated with a patient. Using a machine learning model, the series of selections and the unprocessed MRI data are processed. The series of selections being processed corresponds to the series of inquiries. A symptom severity indicator for a mental health category of the patient is outputted.

8 Claims, 44 Drawing Sheets

(51) Int. Cl.
*G16H 50/20* (2018.01)
*G06T 7/00* (2017.01)
(52) U.S. Cl.
CPC ............... *G06T 2207/10088* (2013.01); *G06T 2207/20081* (2013.01); *G06T 2207/20084* (2013.01); *G06T 2207/30016* (2013.01)

Dysregulated Mood Models

Anhedonia Models

Anxiety Models

MULTIMODAL BIOMARKERS PREDICTIVE OF TRANSDIAGNOSTIC SYMPTOM SEVERITY

CROSS-REFERENCE TO RELATED APPLICATION

This application is the National Phase of International Application PCT/US2019/048809, filed Aug. 29, 2019, which designated the United States, which claims priority to and the benefit of U.S. Provisional Patent No. 62/726,009 filed Aug. 31, 2018 and U.S. Provisional Patent No. 62/840,178 filed Apr. 29, 2019, each of which is hereby incorporated by reference herein in its entirety.

TECHNICAL FIELD

The present disclosure relates to biomarkers, and more specifically, to the use of machine learning and multi-modal biomarkers to predict symptom severity.

BACKGROUND

Conventional clinical psychiatric practice focuses on diagnostic classification, relying on making diagnoses and recommending treatment for disorders based solely on clinical phenomenology. This approach hampers prognostic assessment, treatment, and drug development because it does not take into account the neurobiology of patients.

Biomarkers are biological characteristics that can serve as indicators for normal or pathological processes or responses to intervention. Biomarker development within psychiatry lags behind other areas of medicine, partly because psychiatric syndromes have a far more complex relationship between the biology and severity of the symptoms than other fields of medicine. Conventional clinical practice does not provide biological measures which are able to robustly describe complex psychiatric syndromes. Additionally, conventional diagnostic biomarker approaches do not fully account for the heterogeneity of symptoms under the umbrella of a single diagnosis or the shared symptoms between multiple diagnoses. Clinical symptoms, such as depressed/elevated mood, anhedonia, and anxiety, often span multiple diagnostic categories.

Conventional research suggests that derived symptom dimensions are associated with resting-state functional magnetic resonance imaging (rs-fMRI) connectivity transdiagnostically (i.e., where multiple diagnostically-distinct patient groups are modeled together). Other research found links between task-based fMRI activation or rs-fMRI connectivity and existing anhedonic, depressive, and anxiety symptom dimensions transdiagnostically. This symptom-to-neurophysiological-links in conventional research, however, lacks a predictive framework, and any insights from neuro-imaging-based biomarker research have not translated into clinical practice. Therefore, conventional clinical practice does not provide transdiagnostic, multimodal predictive models of symptom severity which include neurobiological characteristics.

In particular, conventional research does not identify whether symptoms have a more circumscribed biological basis to few brain networks as proposed in a recent taxonomy or to multiple networks. Additionally, it is not known whether a single, broad self-report clinical assessment (like the Temperament and Character Inventory or the Hopkins Symptom Checklist, as known in the art) or multiple, more specific instruments are better at assessing multiple symptoms.

SUMMARY

Aspects of the present disclosure include a system for evaluating mental health of a patient. The system comprises a display device, a user interface, a memory, and a control system. The memory contains machine readable medium, comprising machine executable code. The machine executable code stores instructions for performing a method. The control system is coupled to the memory, and includes one or more processors. The control system is configured to execute the machine executable code to cause the control system to perform the method. The method includes displaying a series of inquiries from mental health questionnaires on the display device. Each inquiry of the series of inquiries includes text and a set of answers. A series of selections is received from the user interface. Each selection of the series of selections is representative of an answer of the set of answers for each corresponding inquiry in the series of inquiries. Unprocessed MRI data are received. The unprocessed MRI data correspond to a set of MM images of a biological structure associated with the patient. Using a machine learning model, the series of selections and the unprocessed MM data are processed. The series of selections being processed corresponds to the series of inquiries. A symptom severity indicator for a mental health category of the patient is outputted.

In some aspects, the unprocessed MM data corresponds to MRI data for a brain of the patient. In some aspects, the unprocessed MRI data includes fMRI data. In some aspects, the control system is further configured to preprocess the unprocessed MRI data to identify a plurality of features.

In some aspects, the mental health category of the patient comprises at least one of: depression, anxiety, and anhedonia. In some aspects, the symptom severity indicator for the mental health category is quantitative.

In some aspects, the machine learning model is at least one of: a generalized linear model, a regression model, a supervised regression method, a logistical regression model, random forest, lasso, and an elastic net.

In some aspects, the machine learning model is generated by receiving labeled training data for a plurality of individuals. The labeled training data is indicative of whether each of the plurality of individuals has one or more mental health disorders and a severity of symptoms corresponding to the one or more mental health disorders. The labeled training data includes unprocessed MRI data recorded for each of the plurality of individuals, and a series of selections corresponding to the series of inquiries for each of the plurality of individuals. The machine learning model is further generated by determining a plurality of features based on the received labeled training data. Based on the determined plurality of features, an initial machine learning model is trained in a supervised manner. Based on the training of the initial machine learning model, importance measures for each of the plurality of features are extracted. Based on the extracted importance measures for the plurality of features, a plurality of subset machine learning models is generated. A classification performance of the generated plurality of subset machine learning models is evaluated. At least one of the subset machine learning models is selected as the machine learning model.

In some aspects, the machine learning model is trained on clinical scales data corresponding to the plurality of individuals. In some aspects, the machine learning model is trained on fMRI full connectivity data corresponding to the plurality of individuals.

In some aspects, the machine learning model is trained on sMRI data corresponding to the plurality of individuals. The sMRI data include cortical volume data, cortical thickness data, and cortical surface area data.

In some aspects, the machine learning model is trained on input data corresponding to the plurality of individuals. In an exemplary aspect, for each individual, the input data include clinical scales data and fMRI data. In another exemplary aspect, for each individual, the input data include clinical scales data and sMRI data. In yet another exemplary aspect, for each individual, the input data include fMRI data and sMRI data. In a further exemplary aspect, for each individual, the input data include fMRI data, clinical scales data, and sMRI data.

Additional aspects of the present disclosure include a system for evaluating mental health of a patient. The system includes a display device, a user interface, a memory, and a control system. The memory includes machine readable medium comprising machine executable code. The machine executable code stores instructions for performing a method. The control system is coupled to the memory, and includes one or more processors. The control system is configured to execute the machine executable code to cause the control system to receive a selection of answers from the user interface. The selection of answers corresponds to each question in a series of questions from mental health questionnaires. Unprocessed MM data are received. The unprocessed MRI data correspond to a set of MRI images of a biological structure. Using a machine learning model, the selection of answers and the unprocessed MRI data are processed. A symptom severity indicator for a mental health category of the patient is outputted.

Further aspects of the present disclosure include a machine learning training system. The machine learning training system includes at least one nontransitory processor-readable storage medium, and at least one processor communicatively coupled to the at least one nontransitory processor-readable storage medium. The at least one nontransitory processor-readable storage medium stores at least one of processor-executable instructions or data. In operation, the at least one processor configured to receive labeled training data for a plurality of individuals. The labeled training data are indicative of whether each of the plurality of individuals has one or more mental health disorders and a severity of symptoms corresponding to the one or more mental health disorders. The labeled training data include MRI data recorded for each of the plurality of individuals, and a selection of answers to the series of questions for each of the plurality of individuals. A plurality of features is determined from the labeled training data. Based on the plurality of features, an initial machine learning model is trained in a supervised manner. Based on the training of the initial machine learning model, importance measures for each of the plurality of features are extracted. Based on the extracted importance measures for the plurality of features, a plurality of subset machine learning models is generated. A classification performance of the generated plurality of subset machine learning models is evaluated. At least one of the subset machine learning models is selected as the machine learning model. The plurality of features of the machine learning model is stored in the at least one nontransitory processor-readable storage medium for subsequent use as a screening tool.

In some aspects, the machine learning system further includes using the features of the machine learning model as a screening tool to assess at least one of intermediate or end-point outcomes in at least one clinical trial testing for treatment responses.

In some aspects, each feature in the plurality of features comprises an importance measure. Each of the subset machine learning models includes a sequentially lower number of features than a following subset machine learning model. The features are selected for each subset machine learning model based on a highest importance measure.

In some aspects, the selected subset machine learning model includes a portion of the plurality of features. The portion selected from features includes an importance measure above a threshold value. In some aspects, each of the subset machine learning models includes a different selection of the portion of the plurality of features. In some aspects, each of the subset machine learning models includes a different combination of the plurality of features. In some aspects, at least twenty features of the plurality of features have an importance measure above the threshold value. The portion includes at least ten features and less than twenty features.

In some aspects, the machine learning model is configured to output a symptom severity indicator identifying a severity of at least one mental health symptom of a patient.

In some aspects, training the initial machine learning model includes using k-fold cross validation with logistic regression.

In some aspects, the labeled training data further comprises at least one of functional measurement data or physiological measurement data.

The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present disclosure, when taken in connection with the accompanying drawings and the appended claims.

BRIEF DESCRIPTION OF THE DRAWINGS

The foregoing and other advantages of the present disclosure will become apparent upon reading the following detailed description and upon reference to the drawings.

Figure 1A:
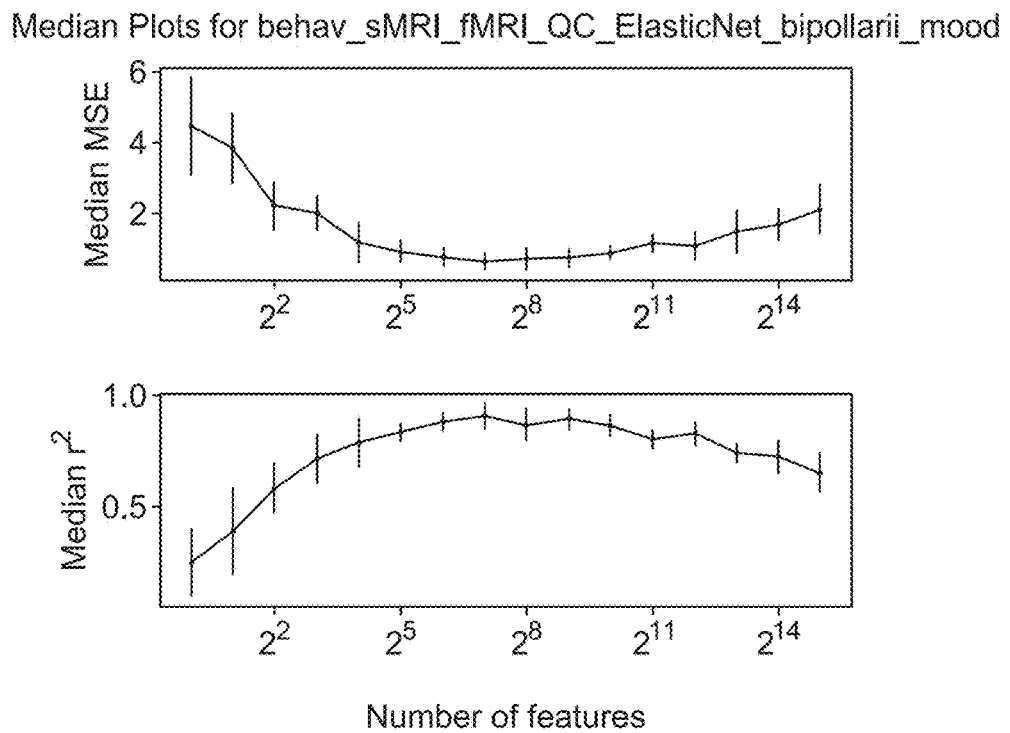
FIG. 1A illustrates X-Y plots of number of features versus predicted outcome scores, according to some implementations of the present disclosure.

While the present disclosure is susceptible to various modifications and alternative forms, specific embodiments have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DETAILED DESCRIPTION

The present disclosure is described with reference to the attached figures, where like reference numerals are used throughout the figures to designate similar or equivalent elements. The figures are not drawn to scale, and are provided merely to illustrate the instant disclosure. Several aspects of the disclosure are described below with reference to example applications for illustration. It should be understood that numerous specific details, relationships, and methods are set forth to provide a full understanding of the disclosure. One having ordinary skill in the relevant art, however, will readily recognize that the disclosure can be practiced without one or more of the specific details, or with other methods. In other instances, well-known structures or operations are not shown in detail to avoid obscuring the disclosure. The present disclosure is not limited by the illustrated ordering of acts or events, as some acts may occur in different orders and/or concurrently with other acts or events. Furthermore, not all illustrated acts or events are required to implement a methodology in accordance with the present disclosure.

Aspects of the present disclosure can be implemented using one or more suitable processing device, such as general-purpose computer systems, microprocessors, digital signal processors, micro-controllers, application-specific integrated circuits (ASIC), programmable logic devices (PLD), field-programmable logic devices (FPLD), field-programmable gate arrays (FPGA), mobile devices such as a mobile telephone or personal digital assistants (PDA), a local server, a remote server, wearable computers, tablet computers, or the like.

Memory storage devices of the one or more processing devices can include a machine-readable medium on which is stored one or more sets of instructions (e.g., software) embodying any one or more of the methodologies or functions described herein. The instructions can further be transmitted or received over a network via a network transmitter receiver. While the machine-readable medium can be a single medium, the term "machine-readable medium" should be taken to include a single medium or multiple media (e.g., a centralized or distributed database, and/or associated caches and servers) that store the one or more sets of instructions. The term "machine-readable medium" can also be taken to include any medium that is capable of storing, encoding, or carrying a set of instructions for execution by the machine and that cause the machine to perform any one or more of the methodologies of the various embodiments, or that is capable of storing, encoding, or carrying data structures utilized by or associated with such a set of instructions. The term "machine-readable medium" can accordingly be taken to include, but not be limited to, solid-state memories, optical media, and magnetic media. A variety of different types of memory storage devices, such as a random access memory (RAM) or a read-only memory (ROM) in the system or a floppy disk, hard disk, CD ROM, DVD ROM, flash, or other computer-readable medium that is read from and/or written to by a magnetic, optical, or other reading and/or writing system that is coupled to the processing device, can be used for the memory or memories.

Overview

The present disclosure provides predictive models for three common symptoms in psychiatric disorders (dysregulated mood, anhedonia, and anxiety). In some examples, the predictive models successfully utilize data from the Consortium for Neuropsychiatric Phenomics (CNP) dataset, which includes clinical scale assessments, resting-state functional MRI (rs-fMRI), and structural-MRI (sMRI) imaging measures. The data is provided from healthy control participants and patients with schizophrenia, bipolar disorder, and attention deficit and hyperactivity disorder (ADHD). In addition, examining symptoms in transdiagnostic groups can be highly informative. The CNP dataset further includes three patient groups with shared genetic risk and includes MRI and clinical scale data for each patient.

According to some implementations of the present disclosure, the disclosed predictive models, using the disclosed feature selection approach discussed herein, were able to explain 65-90% of variance across the three symptom domains. In some examples, the predictive models explain 22% of variance without using the feature selection approach. For feature selection, the present disclosure provides a data-driven feature selection approach from the field of machine learning, relying on importance-weighted forward selection, to search through a high-dimensional space and optimize model performance and interpretability. This importance-ranked, forward selection modeling approach searches for the most predictive input features from a set of clinical scale measures, sMRI measures, and rs-fMRI measures. Notably, this data-driven way of selecting feature subsets led to multimodal neurobehavioral models with consistently high predictability across multiple symptom domains and to high interpretability enabled by importance scores for individual features. Thus, the present disclosure demonstrates that a shorter, broadly-applicable five-minute rs-fMRI scan and a small set of clinical scale assessments can be used to predict a panel of core symptoms commonly found in various psychiatric disorders.

Exemplary methods involve combining rs-fMRI with select questions from clinical scales; this enables high levels of prediction of symptom severity across diagnostically distinct patient groups. In some examples, connectivity measures beyond a few intrinsic RSNs may carry relevant information for symptom severity.

Overall, Elastic Net regression models with all three input feature types explained the most variance. However, features from the different modalities were not equally represented in the models when evaluating feature importance. The individual, edge-level fMRI connectivity measures between specific network nodes dominated across symptom models, with self-report clinical scales being also highly predictive. These models maximize predictability (in terms of variance) for models whose regression coefficients can be used for interpretation, including features that can be assessed for various clinical and scientific insights.

The transdiagnostic symptom-based approach of the present disclosure provides more options for predicting longitudinal and treatment outcomes beyond those afforded by conventional clinical diagnosis alone. The disclosed approach allows clinicians to estimate symptom severity (and can be used as practical tools in other clinical applications) in broader populations, where the patient might not have an initial diagnosis. Also, using a biological marker of a symptom to track and predict eventual treatment response can introduce clinical efficiencies during a medical treatment. If the biomarker detects treatment-related changes sooner than behavioral/symptomatic changes, it can indicate if a patient is responding to an intervention earlier than conventional treatments; this can be the basis for an earlier continue/switch/end treatment decision by a clinician. In some examples, predicting symptom variation itself and symptom severity could predict treatment response altogether.

Therefore, the present disclosure seeks to integrate functional neuroimaging with other data modalities. Combining biological and clinical variables has led to improved predictability in cancer models but is yet underexplored in psychiatry, outside of the present disclosure. The predictive framework is especially powerful beyond associative frameworks (such as correlation analyses), as it not only allows multivariate modeling to deal with high-dimensional, multimodal data but also provides testing of predictive value and generalizability of those models on an independent sample.

The disclosed models retain a high level of interpretability, enabling several clinical and scientific insights, including: (1) structural features do not substantially contribute to the predictive strength of the models, (2) the Temperament and Character Inventory scale is a valuable predictor of symptom variation across diagnoses, and (3) predictive rs-fMRI connectivity features are widely distributed across many intrinsic resting-state networks (RSN). This disclosed models also clarify the biological basis of symptoms or the utility of different clinical scales for prediction.

Exemplary Systems and Methodologies

Figure 14:
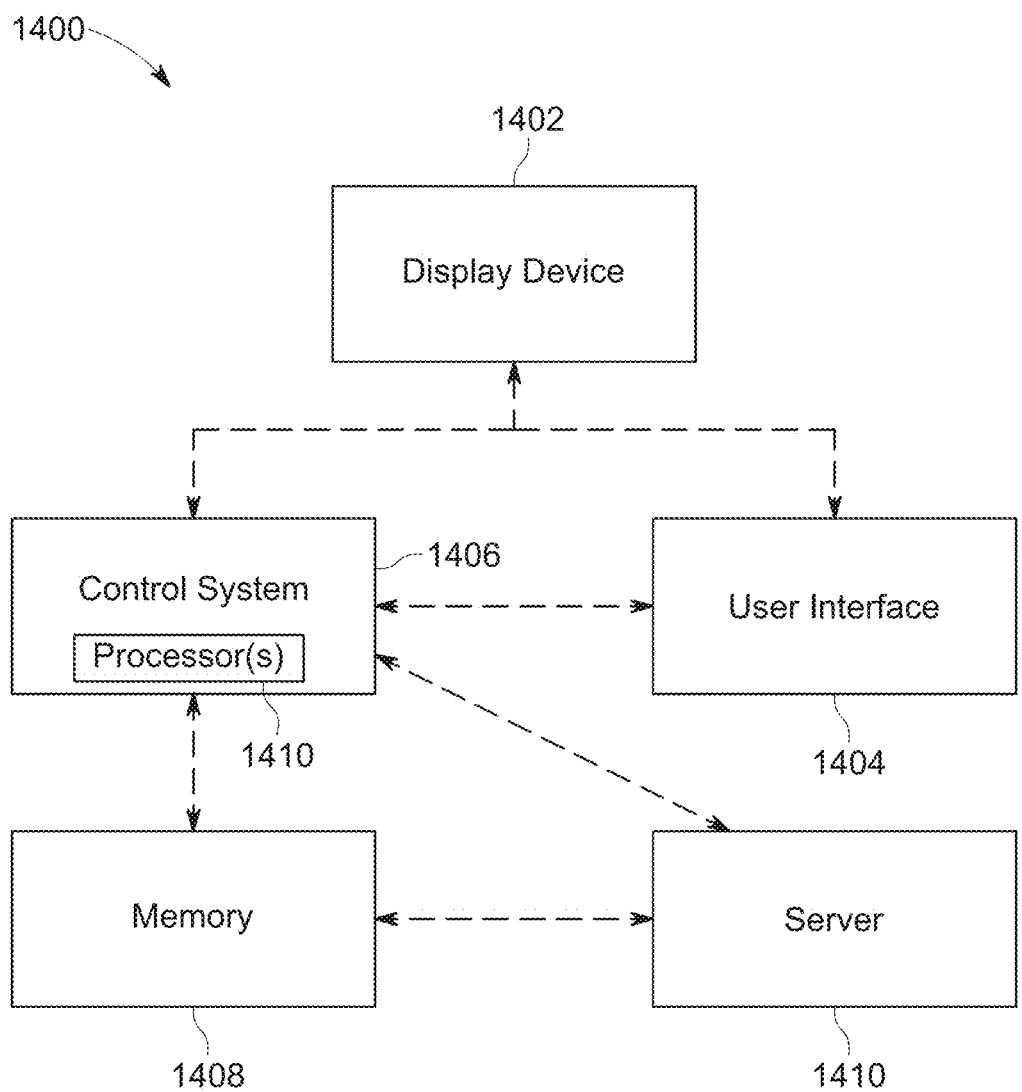
FIG. 14 illustrates an exemplary system for implementing various methodologies disclosed herein, according to some implementations of the present disclosure.

The present disclosure contemplates that a variety of systems can be used to perform various embodiments of the present disclosure. Referring now to FIG. 14, an exemplary system 1400 is shown, which can be configured to perform various methods of the present disclosure, including methods 1500 and 1600 of FIGS. 15 and 16, respectively. In particular, system 1400 includes a display 1402, a user interface 1404, a control system 1406, and a memory 1408. In some examples, the system 1400 further includes one or more servers 1410.

The user interface 1404 is configured to receive input from a user. For example, the user interface 1404 can be a keyboard, a touchscreen, a mobile device, or any other device for receiving input, as known in the art. The user enters data on the user interface 1404 in response to prompts on the display 1402. For example, the display 1402 outputs a series of mental health questions, and the user inputs an answer to each question on the user interface 1404. In some examples, the user interface 1404 directly displays the input on display 1402 and relays the data to the control system 1406. In some examples, the data is then stored in the memory 1408.

The display 1402 is configured to receive data from the control system 1406 and the user interface 1404. For example, the display 1402 displays input received from the user interface 1404; in some examples, the data is first sent to the control system 1406, which then processes the data and instructs the display 1402 according to the processed data. In other examples, the display 1402 displays data received from the control system 1406. Exemplary data from the control system 1406 includes questions from a mental health questionnaire, answer boxes, answer options, answer data, or a symptom severity indicator related data. In some examples, the display 1402 is on a smart phone.

The present disclosure also contemplates that more than one display 1402 can be used in system 1400, as would be readily contemplated by a person skilled in the art. For example, one display can be viewable by a patient, while additional displays are visible to researchers and not to the patient. The multiple displays can output identical or different information, according to instructions by the control system 1406.

The control system 1406 can be communicatively coupled to the display 1402, the user interface 1404, and the memory 1408. Further, the control system 1406 can be communicatively coupled to the server 1410. For example, the communication can be wired or wireless. The control system 1406 is configured to perform any methods as contemplated according to FIGS. 15-16 (discussed further below). The control system 1406 can process and/or store input from the display 1402, the user interface 1404, and the memory 1408. In some examples, the methodologies disclosed herein can be implemented, via the control system 1406, on the server 1410. It is also contemplated that the server 1410 includes a plurality of servers, and can be remote or local. Optionally, the control system and/or the memory 1408 may be incorporated into the server 1410.

In some examples, system 1400 can be a unitary device, for example, a smart phone, which includes a display 1402, a user interface 1404, a control system 1406, and a memory 1408.

Figure 15:
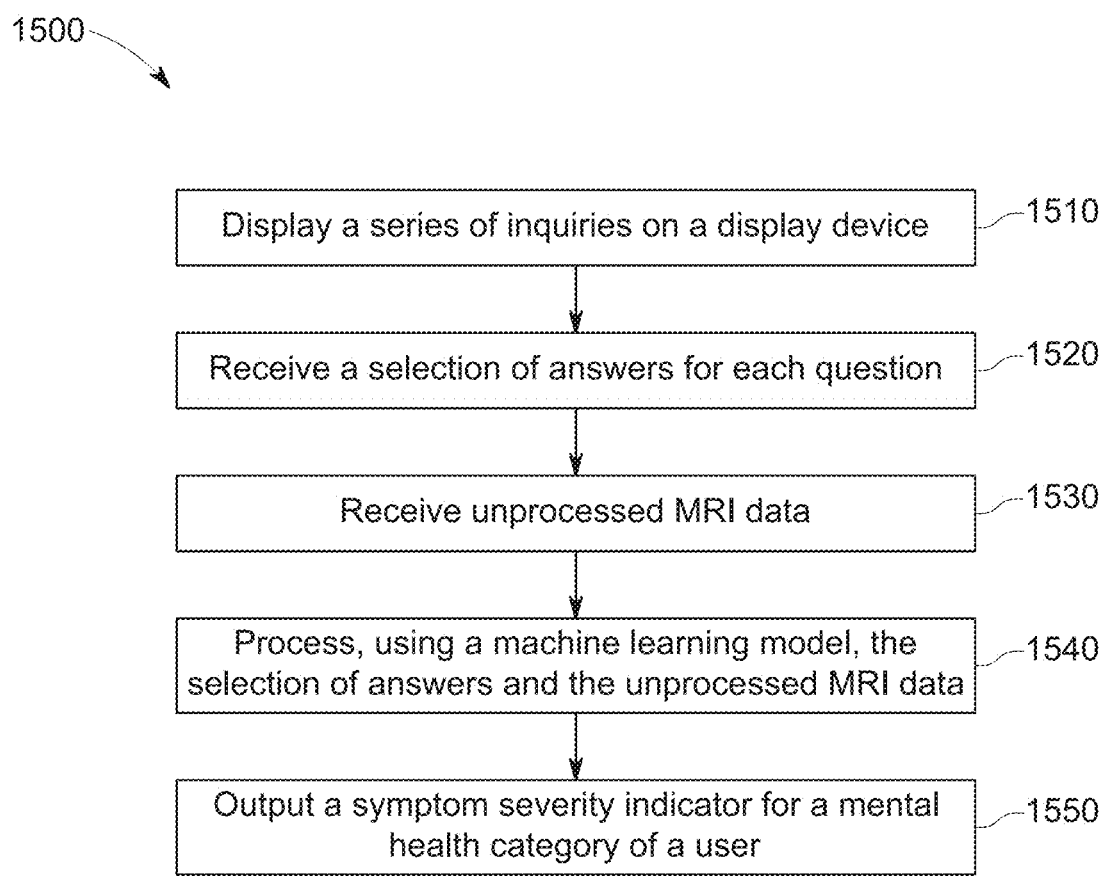
FIG. 15 illustrates an exemplary methodology for determining a symptom severity indicator for a patient, according to some implementations of the present disclosure.

Turning now to FIG. 15, an exemplary methodology 1500 is discussed for determining a symptom severity indicator for a patient. Additional details and alternate steps for methodology 1500 are discussed further with regards to FIGS. 1A-13 and the corresponding description.

Methodology 1500 begins at step 1510 which provides for displaying a series of questions. An exemplary series of questions includes questions from mental health questionnaires, and includes both text and answers for each question.

Methodology 1500 then provides for, at step 1520, receiving answers for each of the series of questions (the questions provided for in step 1510). In some examples, the answers are received at a user interface (e.g., user interface 1404 of FIG. 14). In some examples, the answers include selection of a multiple choice question, a textual response, or any other user input as contemplated by one skilled in the art. In some examples, the answers are retrieved from a record entry corresponding to one patient in a database of patient records. This database can be stored in memory 1408 of FIG. 14, for example. In some examples, the database can be stored in the sever 1410 of FIG. 14. In some examples, methodology 1500 begins directly at step 1520.

Step 1530 provides for receiving unprocessed MRI data. The unprocessed MRI data corresponds to a set of MRI images of a biological structure. In some examples, the MM data corresponds to MM data for a patient's brain (i.e., the same patient who provided answers at step 1520). The MRI data can include task-based fMRI data, rs-fMRI data, and/or sMRI data. In additional examples of step 1530, methodology 1500 can provide for receiving clinical scales data. In some examples of step 1530, methodology 1500 provides for receiving processed MRI data.

Step 1540 then provides for processing, using a machine learning model, the selection of answers from step 1520 and the data received at step 1530. In some examples of methodology 1500, the data received at step 1530 is preprocessed to identify a plurality of features.

At step 1550, methodology 1500 provides for outputting a symptom severity indicator for a mental health category of a user. In some examples of the present disclosure, step 1550 performs processing of the answers and the received data as discussed further below with respect to method 1600 of FIG. 16. The mental health category can include any of (1) depression, (2) anxiety, and (3) anhedonia. In some aspects, the symptom severity indicator for the mental health category is quantitative. For example, the symptom severity indicator includes a numerical scale (such as 1 to 5, 1 to 10, etc.), a color scale (green to yellow to red), an emoji scale, or the like, or in any combination thereof.

In some examples, the symptom severity indicators are scores across a scale. For example, the score can range from zero to forty (0-40); zero indicates no evidence of a symptom, and forty indicates that the patient is severely symptomatic. In some examples, each questionnaire to measure symptom severity can have a different scale. Any other symptom severity scale can be used as well, as would be readily apparent to one skilled in the art.

Figure 16:
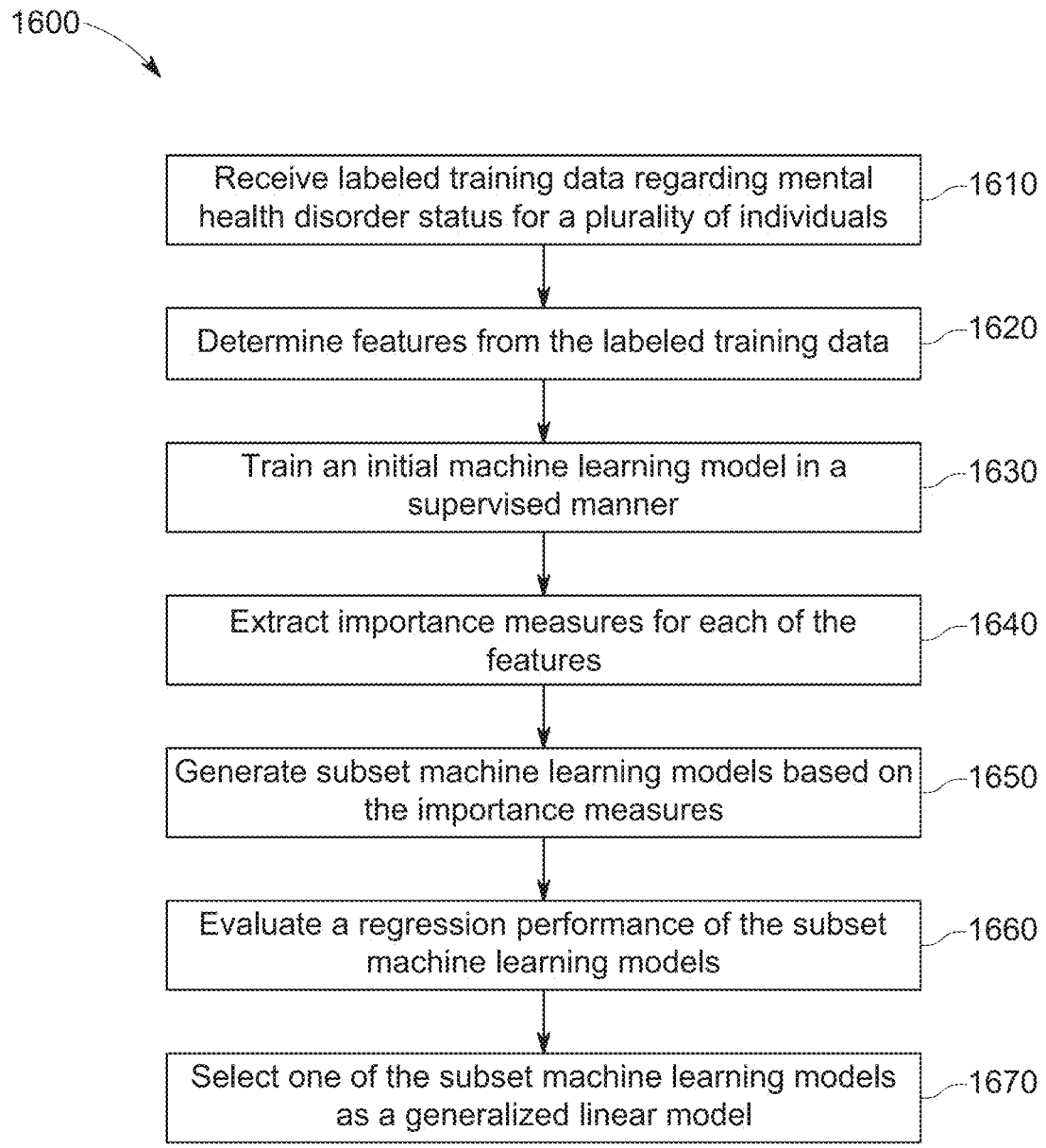
FIG. 16 illustrates an exemplary methodology for using a machine learning model to analyze input and output a symptom severity indicator, according to some implementations of the present disclosure.

Referring now to methodology 1600 of FIG. 16, an exemplary methodology is shown for using a machine learning model to analyze input and output a symptom severity indicator, according to various embodiments of the present disclosure. In some examples, the machine learning model is any of: a generalized linear model, a regression model, a supervised regression method, random forest model, LASSO model, and an elastic net model. In some examples, the machine learning model is any of the models and algorithms discussed further below. In one embodiment of method 1600, the present disclosure provides two regularized general linear model regression algorithms, LASSO and Elastic Net, and one non-linear regression model algorithm, Random Forest. Elastic Net in particular can be used when the number of predictor variables is much greater than the number of samples.

In step 1610, methodology 1600 provides for receiving labeled training data regarding mental health disorder status for a plurality of individuals. In some examples, the labeled training data identifies whether each of the individuals has one or more mental health disorders and the severity of their symptoms. The labeled training data includes, for each individual, a selection of answers to mental health questionnaires and includes MM data. The MRI data can be task-based fMRI data, sMRI data, and/or rs-fMRI data. In some examples, the labeled training data includes, for each individual, an indication of any of: whether the individual is healthy, whether the individual has a general mental health issue, whether the individual has one or more specific mental health disorders, whether the individual is at risk of developing a general mental health issue, or whether the individual is at risk of developing one or more specific mental health disorders. In some examples, the labeled training data includes another functional and/or physiological measurement dataset, as known in the art.

In step 1620, methodology 1600 provides for determining features from the labeled training data of step 1610. The features are determined according to any methods, as known in the art. In other examples, features will not be determined from the labeled training data and they will be input directly into the algorithm.

In step 1630, methodology 1600 provides for training an initial machine learning model in a supervised manner, based on the features determined in step 1620. In some examples, training this initial machine learning model includes using k-fold cross-validation with LASSO and Elastic Net regression.

In some examples, training this initial machine learning model in step 1630 includes training the model on clinical scales data corresponding to the plurality of individuals.

In some examples, training this initial machine learning model in step 1630 includes training the model on fMRI full connectivity data corresponding to the plurality of individuals.

In some examples, training this initial machine learning model in step 1630 includes training the model on sMRI data corresponding to a plurality of individuals, the sMRI data including cortical volume data, cortical thickness data, and cortical surface area data.

In some examples, training this initial machine learning model in step 1630 includes training the model on input data corresponding to the plurality of individuals, wherein, for each individual, the input data includes clinical scales data and fMRI data.

In some examples, training this initial machine learning model in step 1630 includes training the model on input data corresponding to the plurality of individuals, wherein, for each individual, the input data includes clinical scales data and sMRI data.

In some examples, training this initial machine learning model in step 1630 includes training the model on input data corresponding to the plurality of individuals, wherein, for each individual, the input data comprises fMRI data and sMRI data.

In some examples, training this initial machine learning model in step 1630 includes training the model on input data corresponding to the plurality of individuals, wherein, for each individual, the input data comprises fMRI data, clinical scales data, and sMRI data. This particular combination of input data provides a high $r^2$ metric (calculated on an untouched evaluation set data to avoid biasing and overfitting our models) when using Elastic Net across the different outcome variables.

In step 1640, methodology 1600 provides for extracting importance measures for each of the features. These importance measures are selected based on the trained initial machine learning model.

In step 1650, methodology 1600 provides for generating a plurality of subset machine learning models, based on the extracted importance measures of step 1640. In step 1660, methodology 1600 provides for evaluating a regression performance of the generated subset machine learning models from step 1650. In some examples, each of the subset machine learning models includes a different selection of features. In some examples, the subset machine learning models include only features with an importance measure above a threshold value. In some examples, the features are ranked based on the importance measure. In some examples, each of the subset machine learning models includes a sequentially lower number of features than a following subset machine learning model, wherein the features are selected for each subset machine learning model based on a highest importance measure.

In step 1670, methodology 1600 provides for selecting one of the subset machine learning models as a generalized linear learning model. The selection is based on the classification performances as evaluated in step 1660. The selected subset machine learning model includes a portion of the plurality of features determined from step 1620. The portion of features is selected from features with an importance measure (as determined in step 744) above a threshold value. In some examples, more than one subset machine learning model is selected.

In some examples of step 1670, the threshold value is set so that at least twenty features of the plurality of features determined in step 1620 have an importance measure above the threshold value. In some examples, the threshold value is set to select a portion of between ten and twenty features.

In some examples of step 1670, the features of the machine learning model are stored in a non-transitory processor-readable storage medium (e.g., memory 1408 of FIG. 14). The features can then be later used as a screening tool. In some examples, the screening tool can output a symptom severity indicator of a mental health condition. In some examples, the screening tool assesses intermediate and/or end-point outcomes in clinical trial testing for treatment responses.

Therefore, the selected machine learning model can then be used to process any of the input data as provided for in the present disclosure.

In other examples of steps 1660 and 1670, one hundred twenty-six (126) sets of models can be built to examine all permutations of seven feature set inputs, three modeling algorithms, and six outcome variables. The seven feature set inputs include: (1) clinical scales data; (2) fMRI full connectivity data; (2) sMRI cortical volume, cortical area, and cortical thickness data; (3) clinical scales data and fMRI data; (4) clinical scales data and sMRI data; (5) sMRI data and fMRI data; and (7) clinical scales data, fMRI data, and sMRI data. The three modeling algorithms include anxiety, depression, and anhedonia. The six outcome variables can be symptom severity scores, as discussed herein.

As discussed herein, conventional diagnostic biomarker approaches do not fully account for the heterogeneity of symptoms under the umbrella of a single diagnosis or the shared symptoms between multiple diagnoses. It must be noted that conventional clinical practice does not provide transdiagnostic, multimodal predictive models of symptom severity. Thus, based on the seven feature set input, such as the examples disclosed herein with regard to steps 1660 and 1670, various combinations of feature types are evaluated as inputs. For example, instead of only analyzing one type of biomarkers, the various combinations of input data include single and multimodal feature sets. The experimental data herein provides that the multimodal models perform better than those of single feature sets. Therefore, the models disclosed herein can be highly predictive based at least in part on their transdiagnostic and/or multimodal data input.

Example Application of the Disclosed Models

Figure 1B:
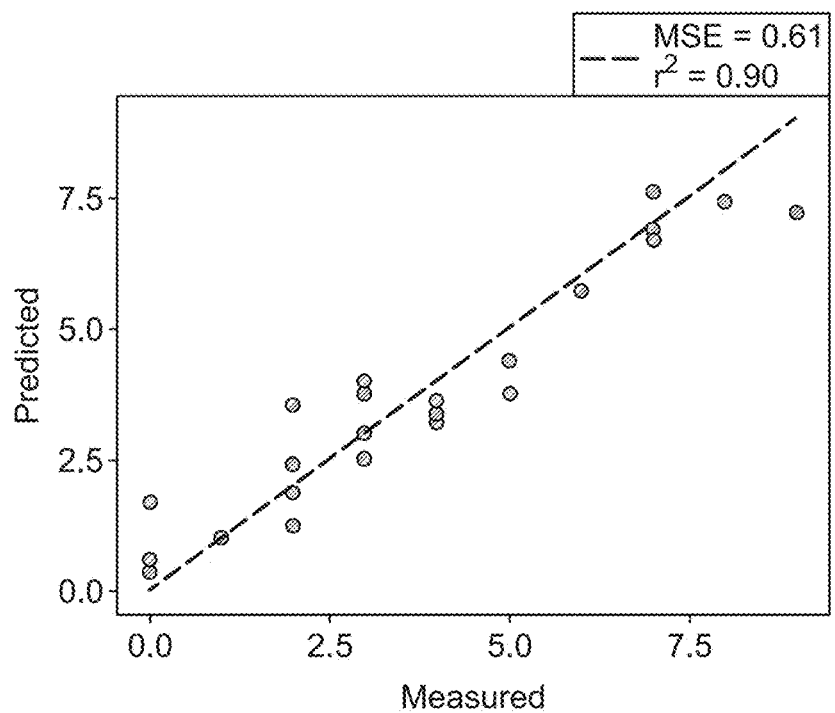
FIG. 1B illustrates a comparison of measured outcome scores and predicted outcome scores, according to some implementations of the present disclosure.

FIGS. 1A-1B show evaluations using the disclosed models (the models are discussed further with regard to FIGS. 14-16 and corresponding description) using candidate subsets according to a prespecified criterion to find an optimal model. FIG. 1A illustrates X-Y plots of number of features versus predicted outcome scores. FIG. 1A shows exemplary data predicting a total Mood_Bipolar score using Elastic Net and clinical scales data, sMRI data, and fMRI data as input. The median MSE and median $r^2$ are shown to vary with each feature subset (standard deviation bars are also shown). FIG. 1B compares measured outcome scores against predicted outcome scores; the data demonstrates how closely the model predictions are to actual outcome scores for individuals. The model predictions are trained on a portion of a dataset, while the measured outcome scores are reserved in a held-out sample, from the same dataset. Additional details of the methodology are discussed further with regards to the experimental methodology.

Figure 2A:
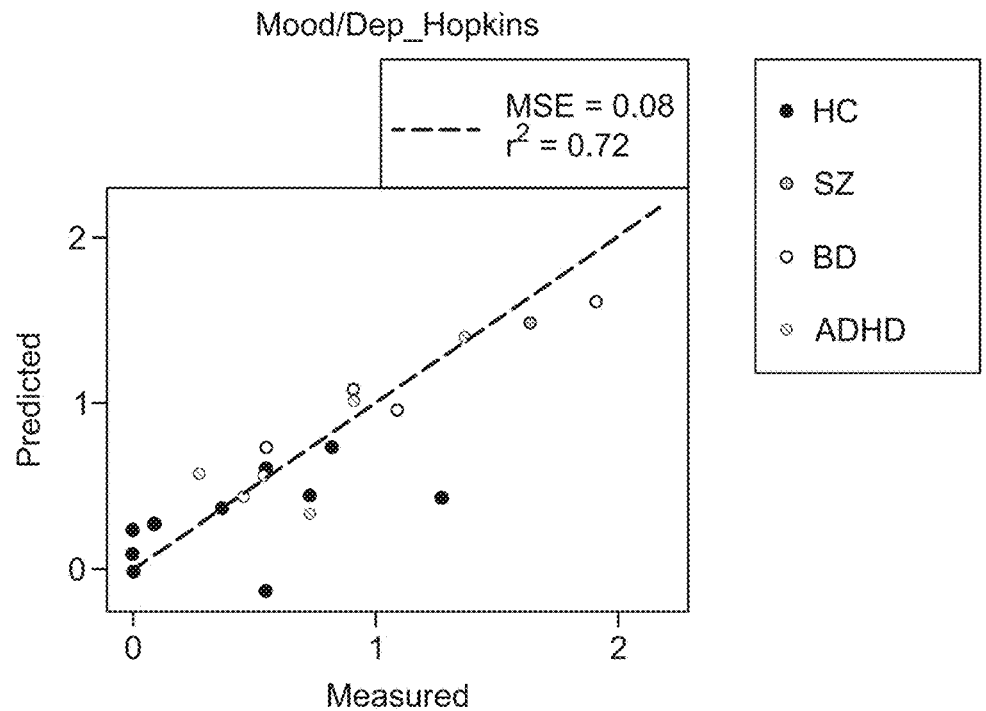
FIGS. 2A-2B illustrate comparisons of measured values and predicted values under dysregulated mood models, according to some implementations of the present disclosure.
Figure 2B:
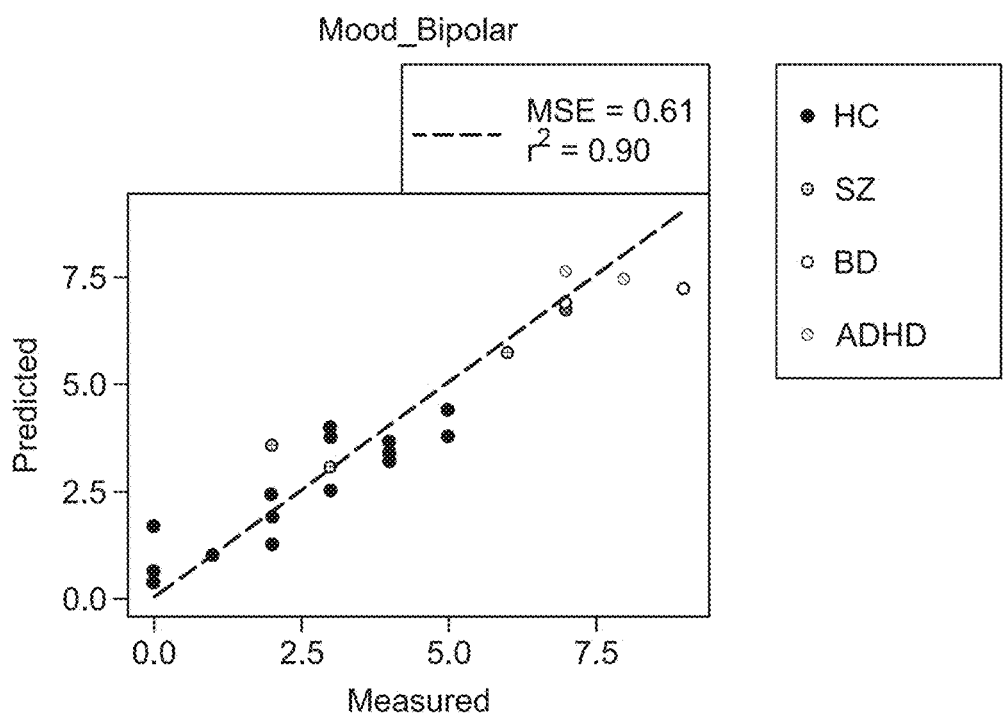
Figure 2C:
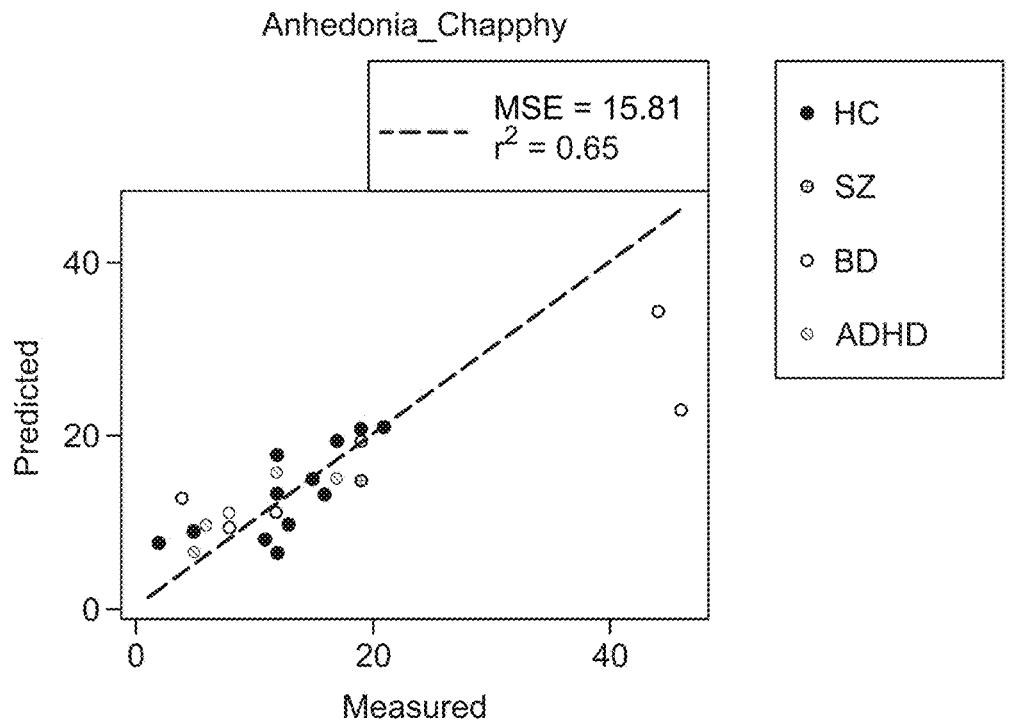
FIGS. 2C-2D illustrate comparisons of measured values and predicted values under anhedonia models, according to some implementations of the present disclosure.
Figure 2D:
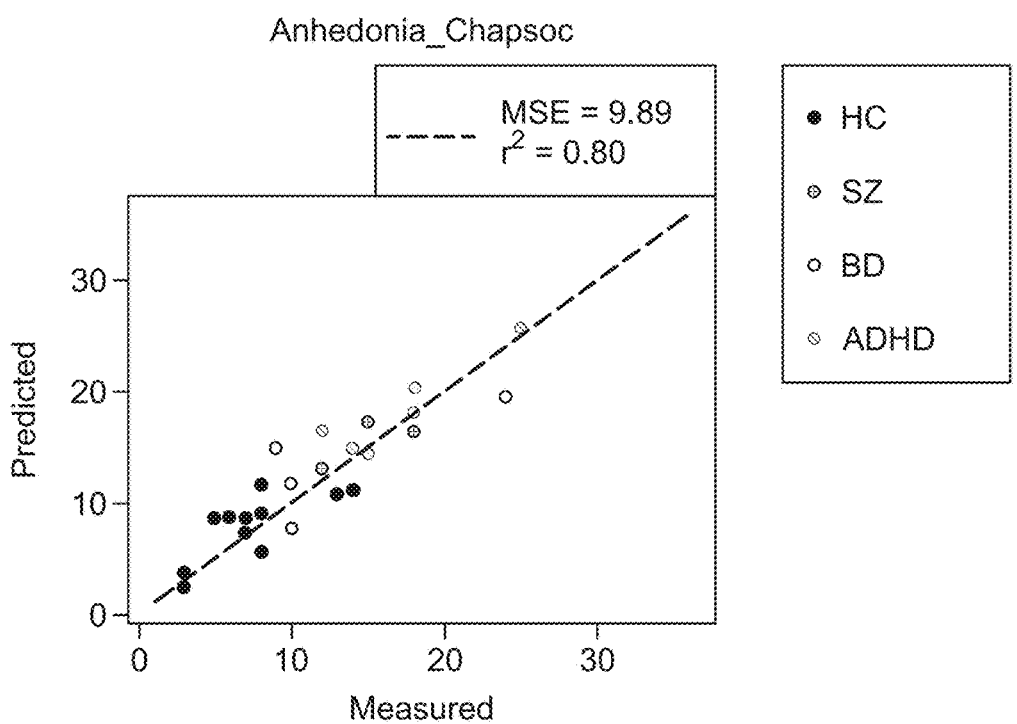
Figure 2E:
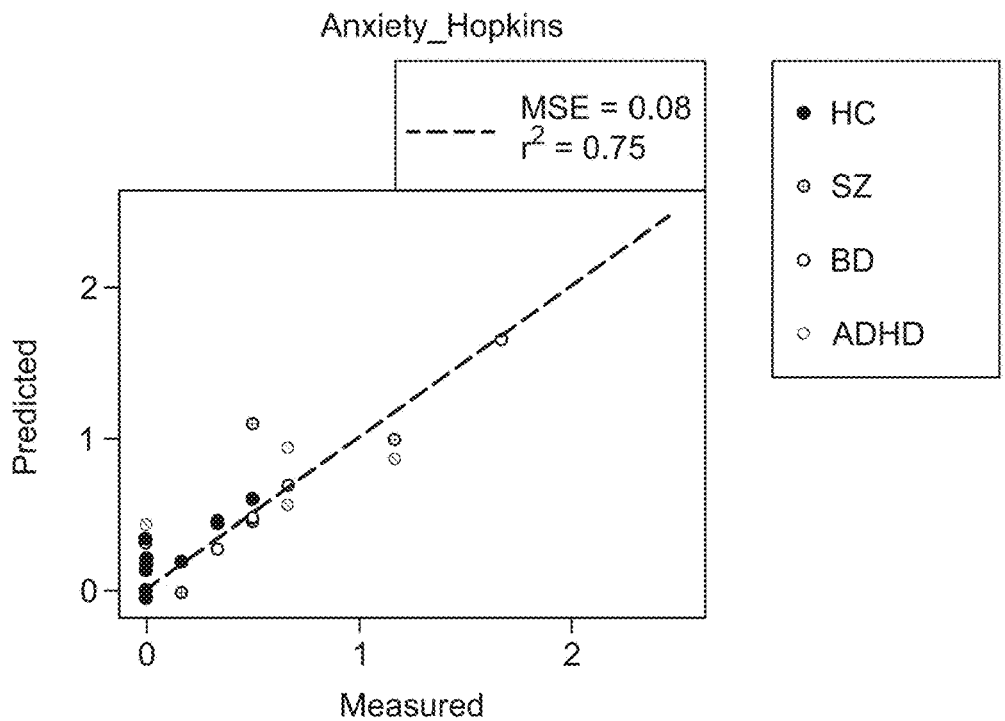
FIG. 2E-2F illustrate comparisons of measured values and predicted values under anxiety models, according to some implementations of the present disclosure.
Figure 2F:
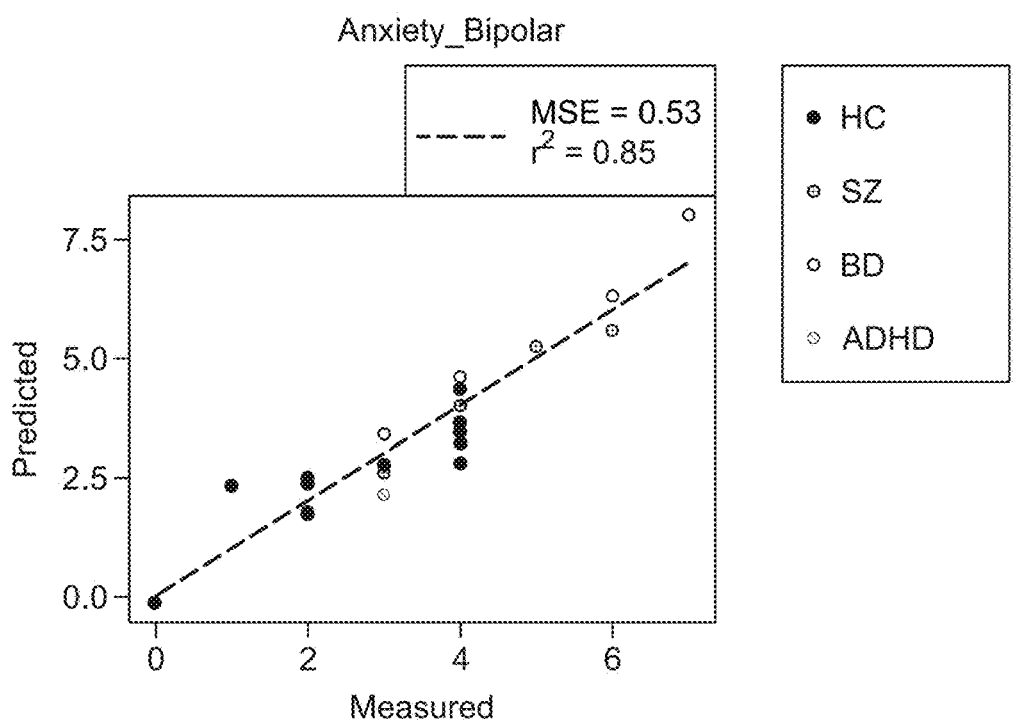

FIGS. 2A-2F compare measured and predicted values for best models for mood, anhedonia, and anxiety. For example: FIGS. 2A-2B illustrate comparisons of measured values and predicted values under dysregulated mood models; FIGS. 2C-2D illustrate comparisons of measured values and predicted values under anhedonia models; and FIG. 2E-2F illustrate comparisons of measured values and predicted values under anxiety models. Each dot in the scatter plot, marked by diagnosis (shown as dots with different hatching), represents a single participant from the held-out evaluation set. Their measured symptom severity score is along the x-axis, and their predicted symptom severity score is along the y-axis. The dashed diagonal line represents a perfect one-to-one linear relationship between measured and predicted values. FIGS. 2A-3C show how closely the model predictions are to actual outcome scores for individuals in the held-out samples for this set of models. In this example, there is no particular diagnostic group that is further from the measured/predicted line across all six models; this suggests that the models generalize across the multiple diagnoses. FIGS. 2A-2C also demonstrate that healthy control subjects are generally in the lower half of the symptom score ranges.

Figure 3A:
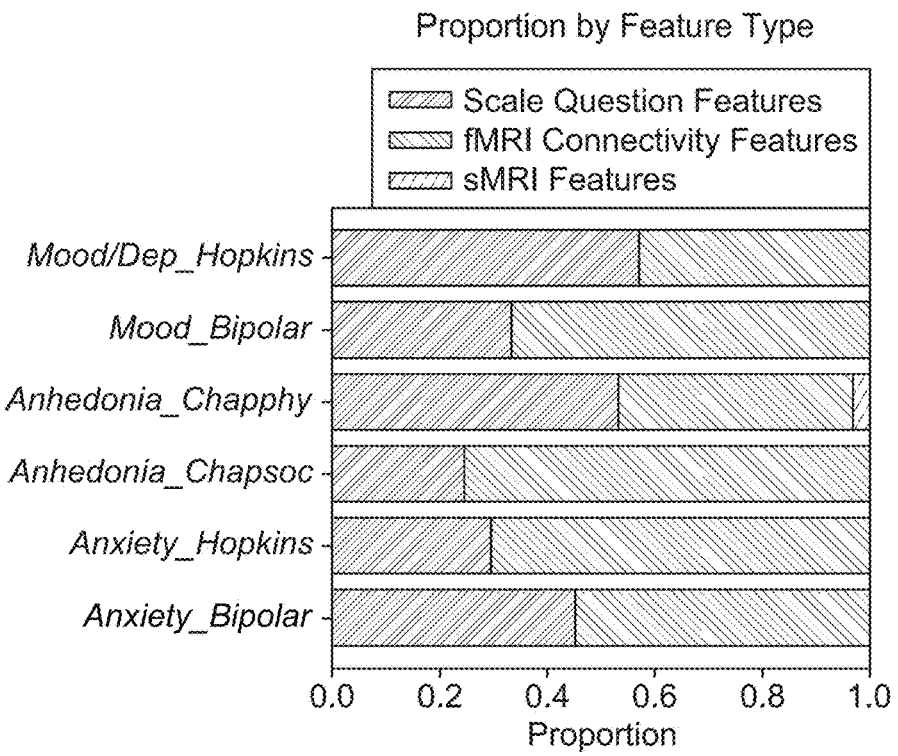
FIG. 3A illustrates exemplary proportions by feature types in some of the disclosed models, according to some implementations of the present disclosure.
Figure 3B:
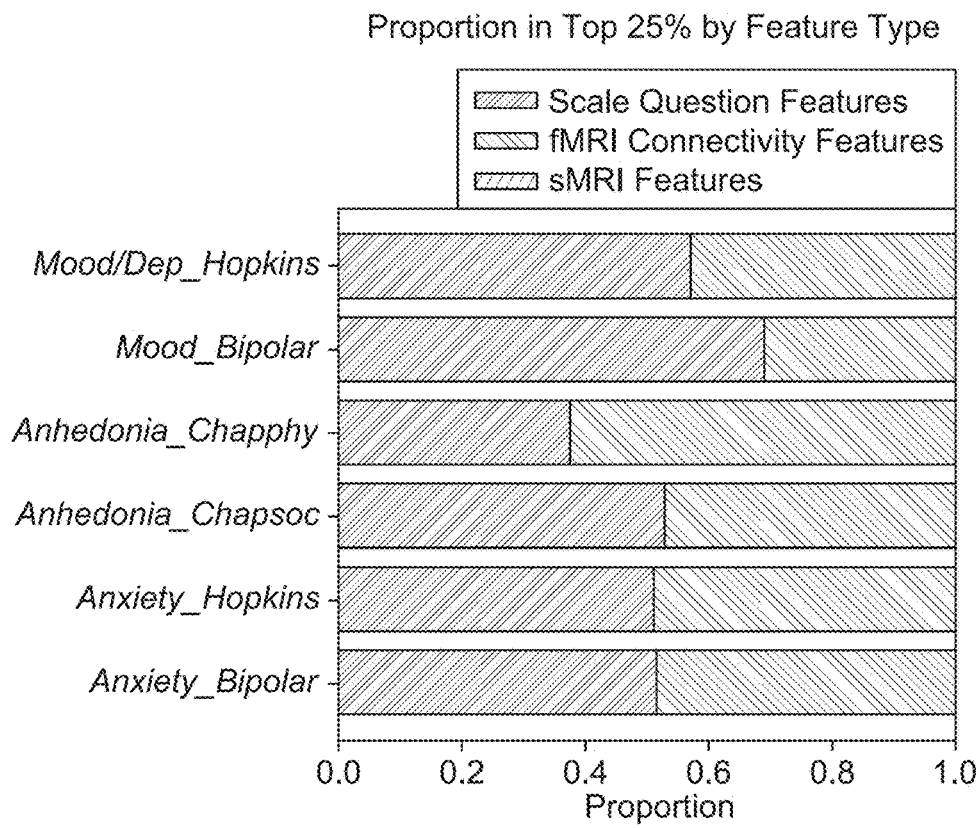
FIG. 3B illustrates exemplary proportions by the top 25% of the feature types in some of the disclosed models, according to some implementations of the present disclosure.

FIGS. 3A-3B show exemplary proportions of feature types in some of the disclosed models. FIG. 3A shows a proportion of all features returned by the model. The densest hatching represents the proportion of features from scales, the medium density hatching represents proportion from fMRI connectivity measures, and the least dense hatching represents proportion from sMRI measures. FIG. 3B shows a proportion of feature types in the top 25% of features returned by the model; this indicates that most of the disclosed models have equal or greater proportion of scale features than among all the non-zero features.

Figure 4A:
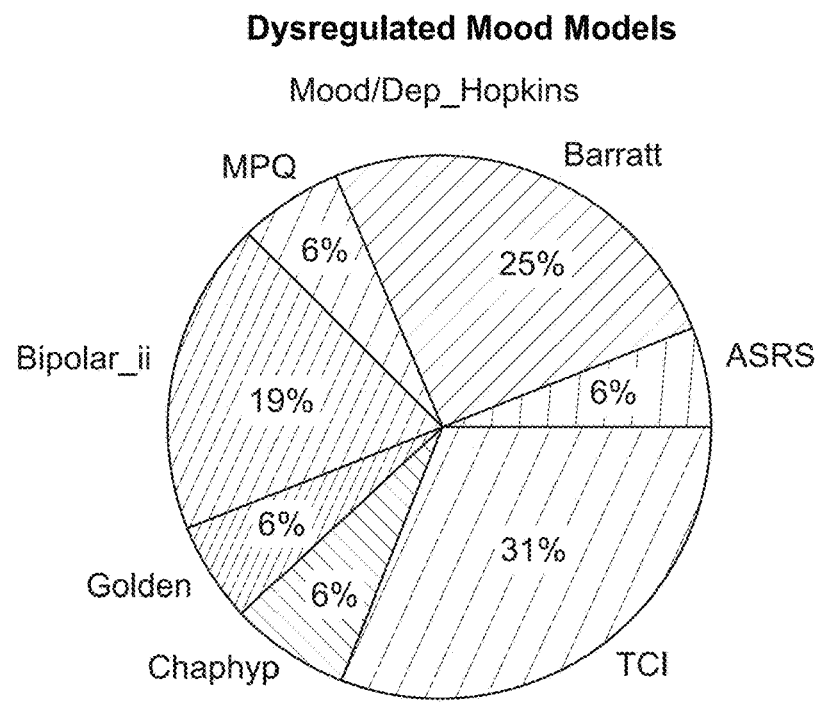
FIGS. 4A-4B illustrate pie charts of exemplary proportions of features from each scale under dysregulated mood models, according to some implementations of the present disclosures
Figure 4B:
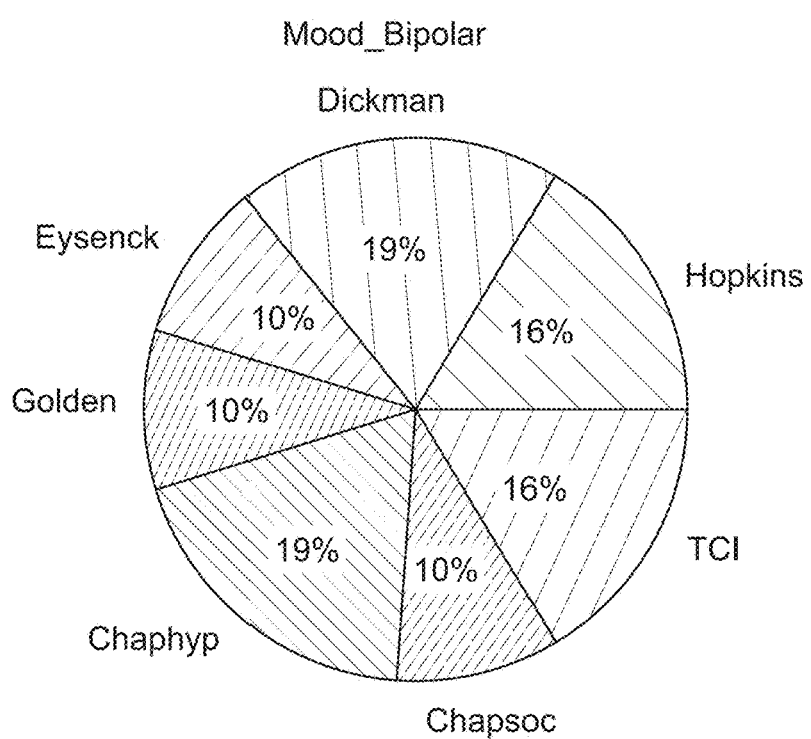
Figure 4C:
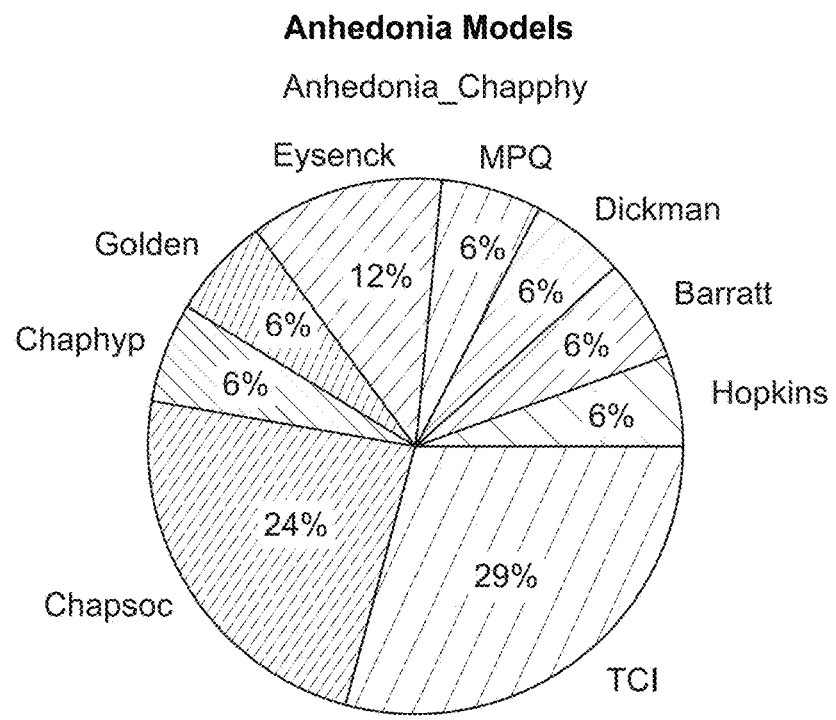
FIGS. 4C-4D illustrate pie charts of exemplary proportions of features from each scale under anhedonia models, according to some implementations of the present disclosure.
Figure 4D:
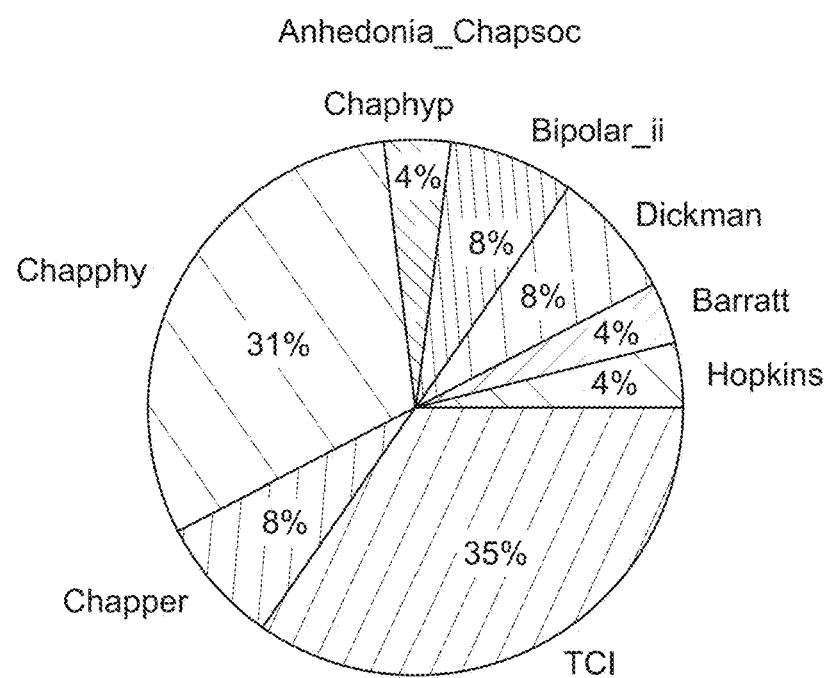
Figure 4E:
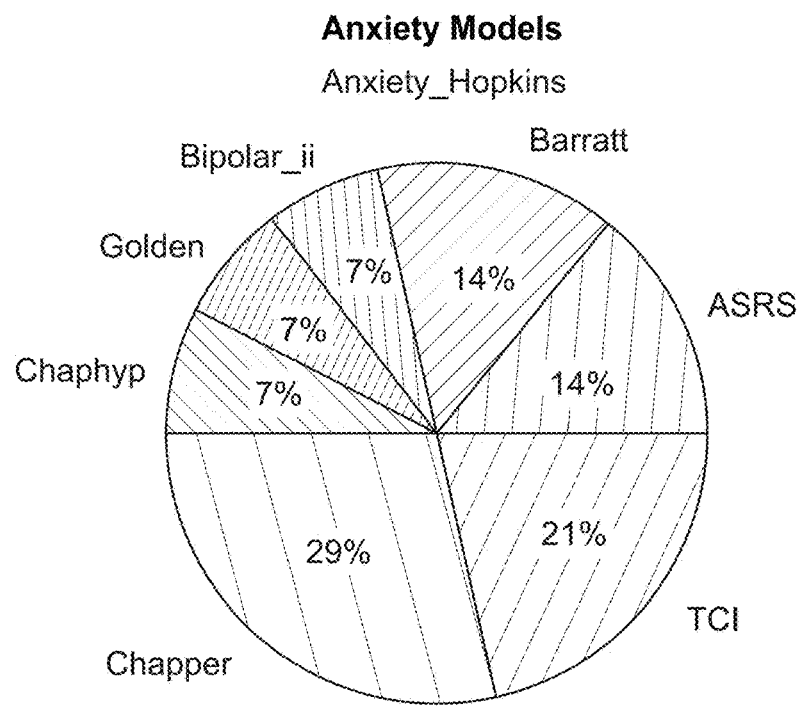
FIGS. 4E-4F illustrate pie charts of exemplary proportions of features from each scale under anxiety models, according to some implementations of the present disclosure.
Figure 4F:
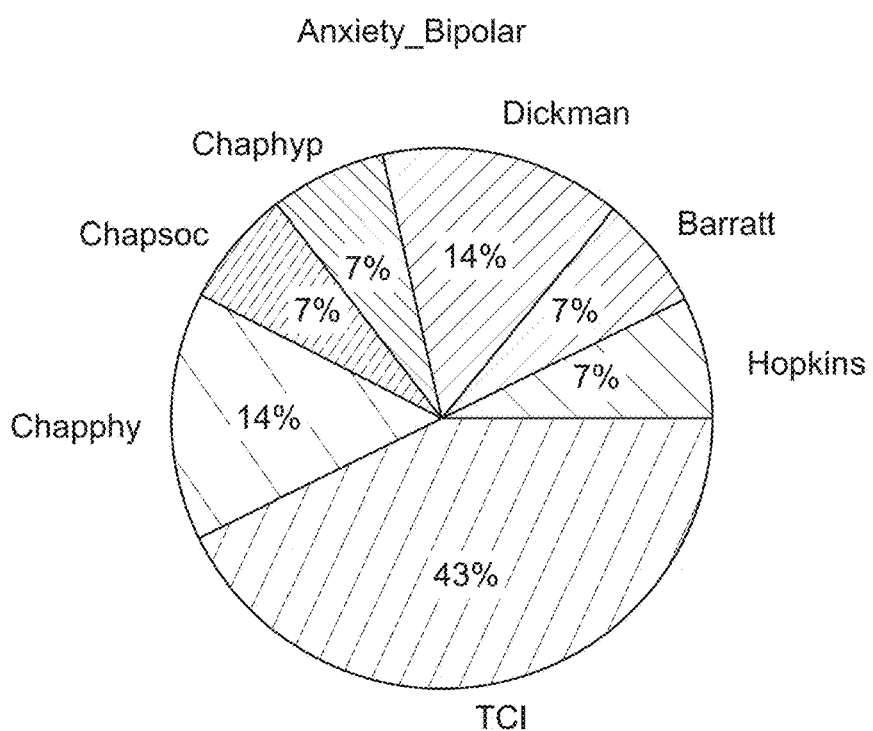
Figure 5A:
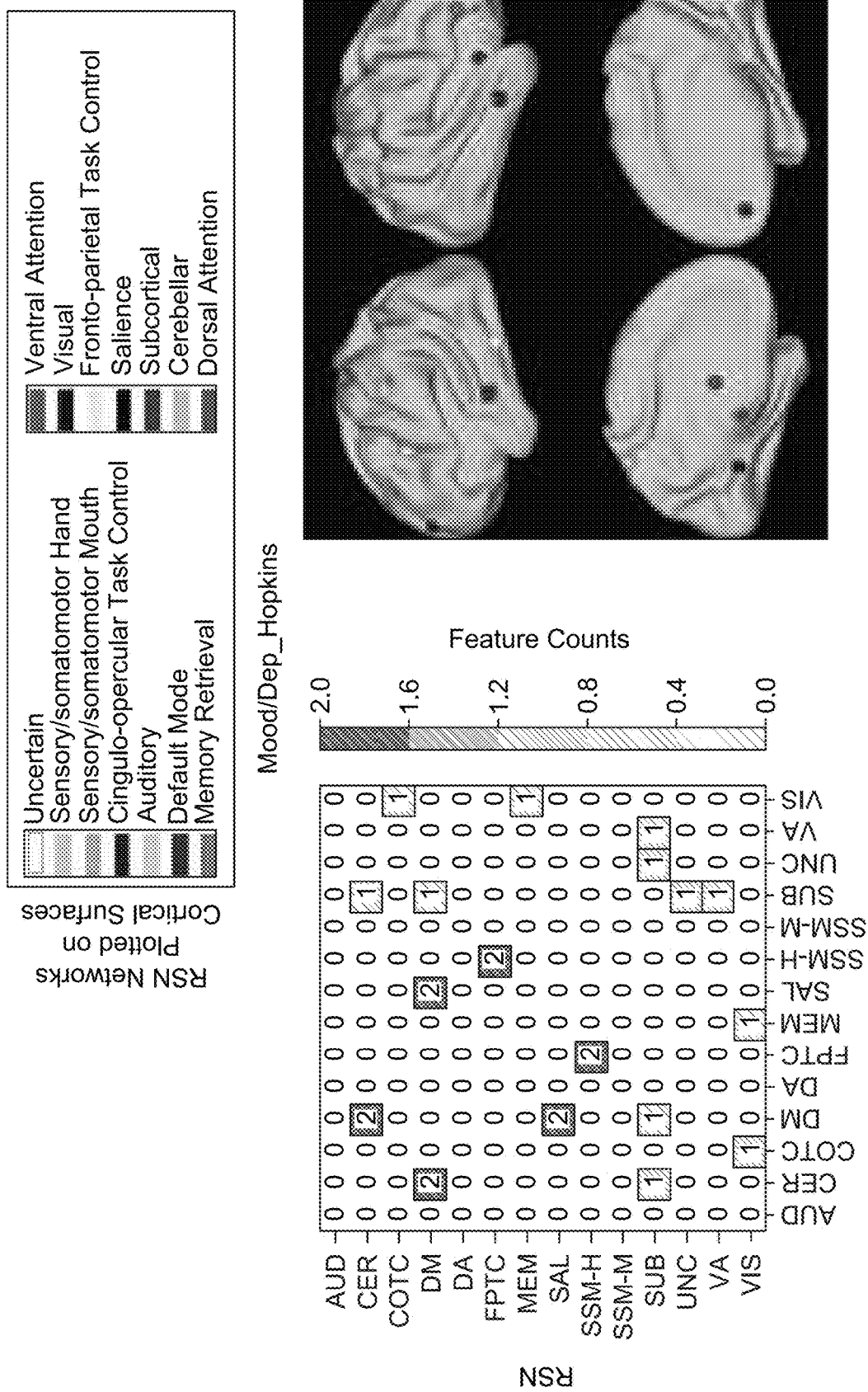
FIGS. 5A-5B illustrate connectivity matrices and region of interest (ROI) locations for fMRI connectivity features in some of the disclosed models predicting mood outcome variables, according to some implementations of the present disclosure.
Figure 5B:
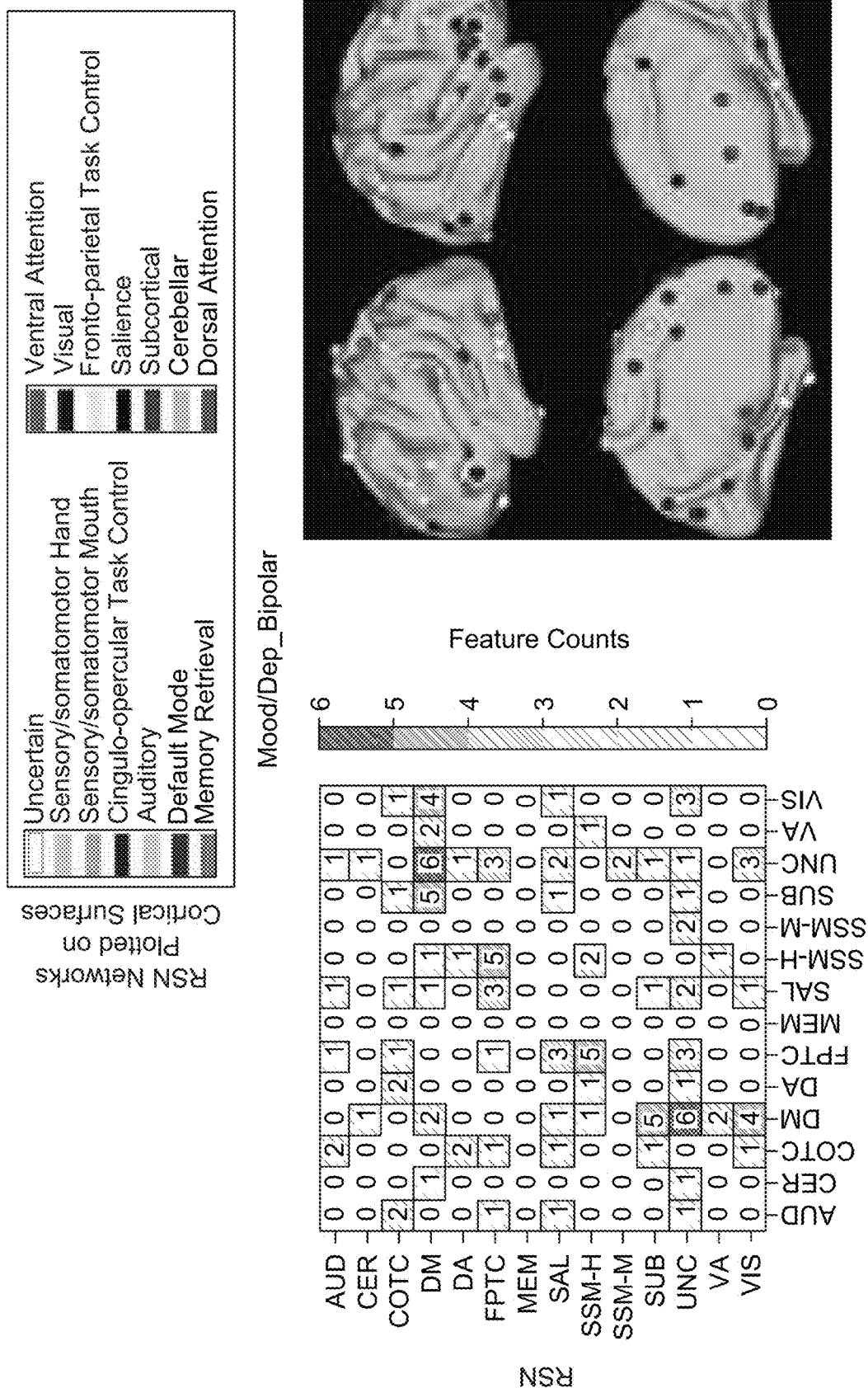
Figure 5C:
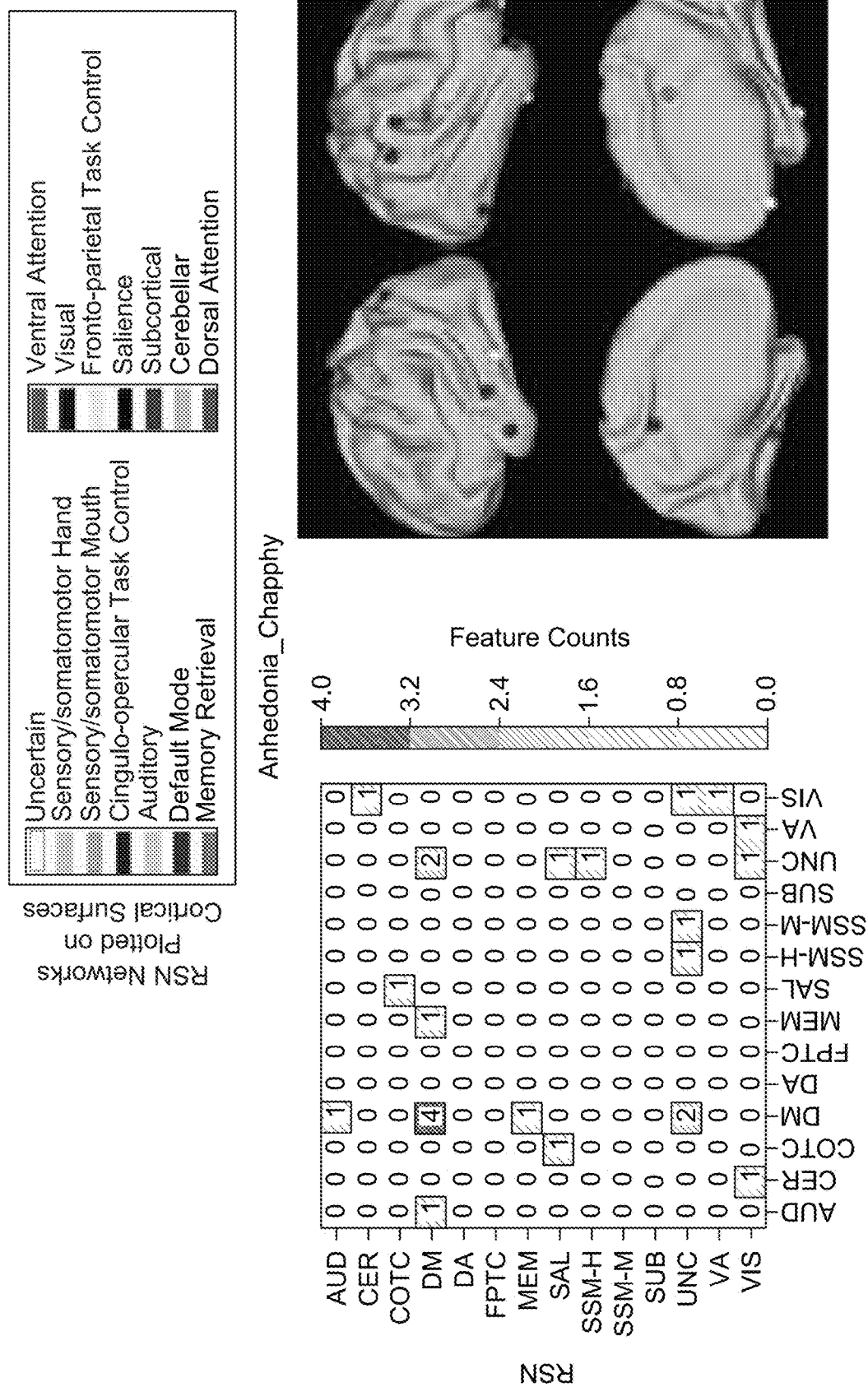
FIGS. 5C-5D illustrate connectivity matrices and ROI locations for fMRI connectivity features in some of the disclosed models predicting anhedonia outcome variables, according to some implementations of the present disclosure.
Figure 5D:
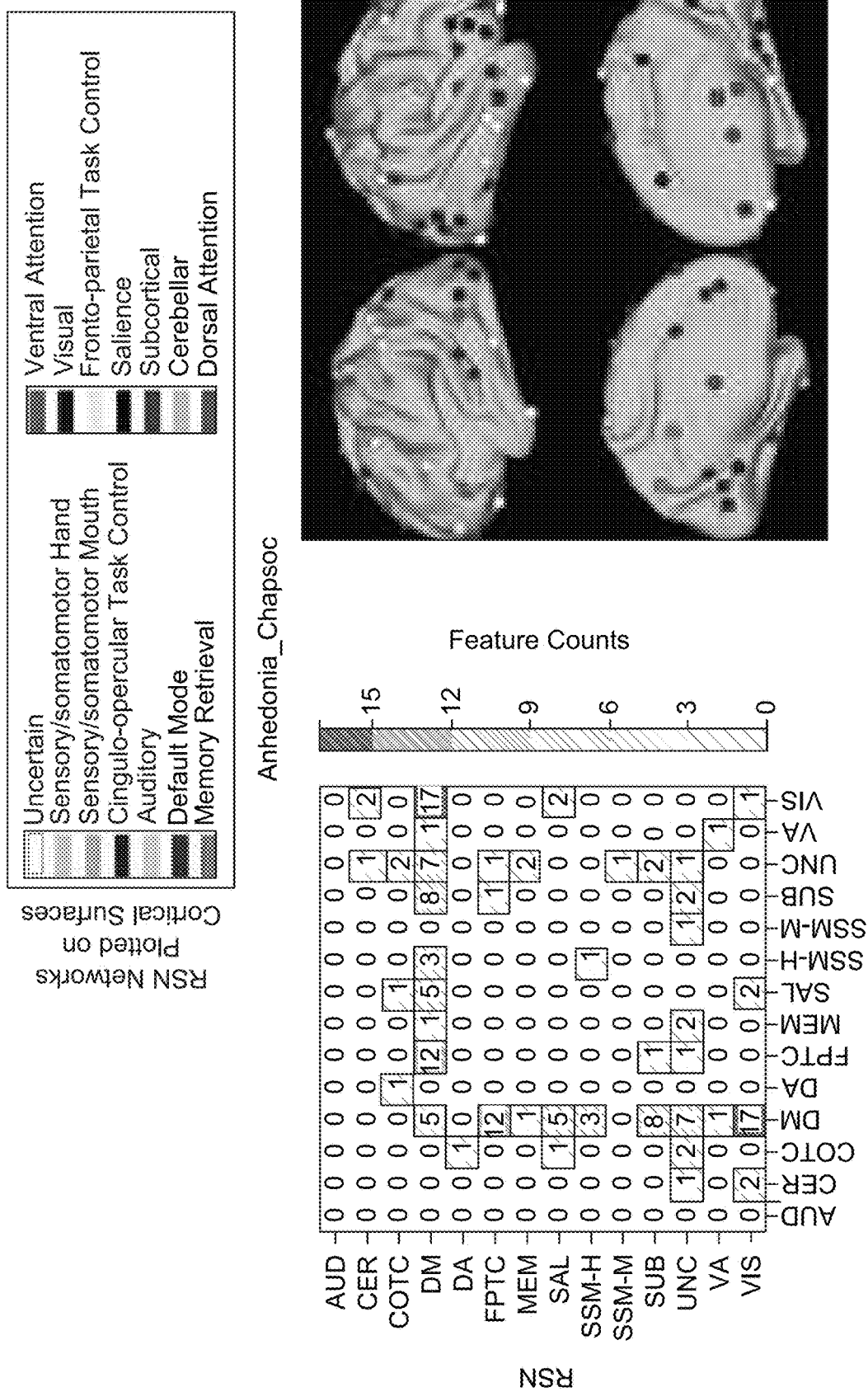
Figure 5E:
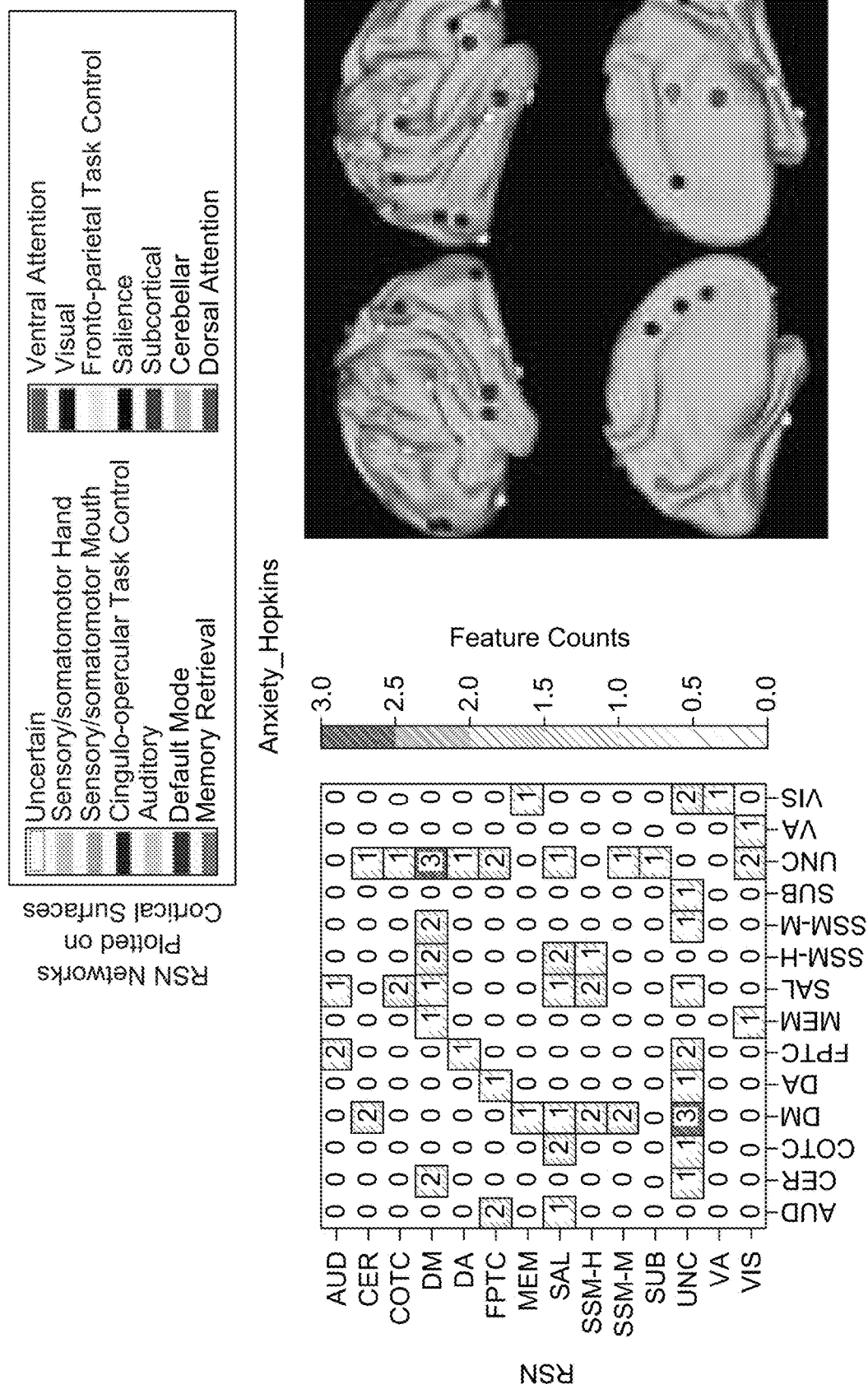
FIGS. 5E-5F illustrate connectivity matrices and ROI locations for fMRI connectivity features in some of the disclosed models predicting anxiety outcome variables, according to some implementations of the present disclosure.
Figure 5F:
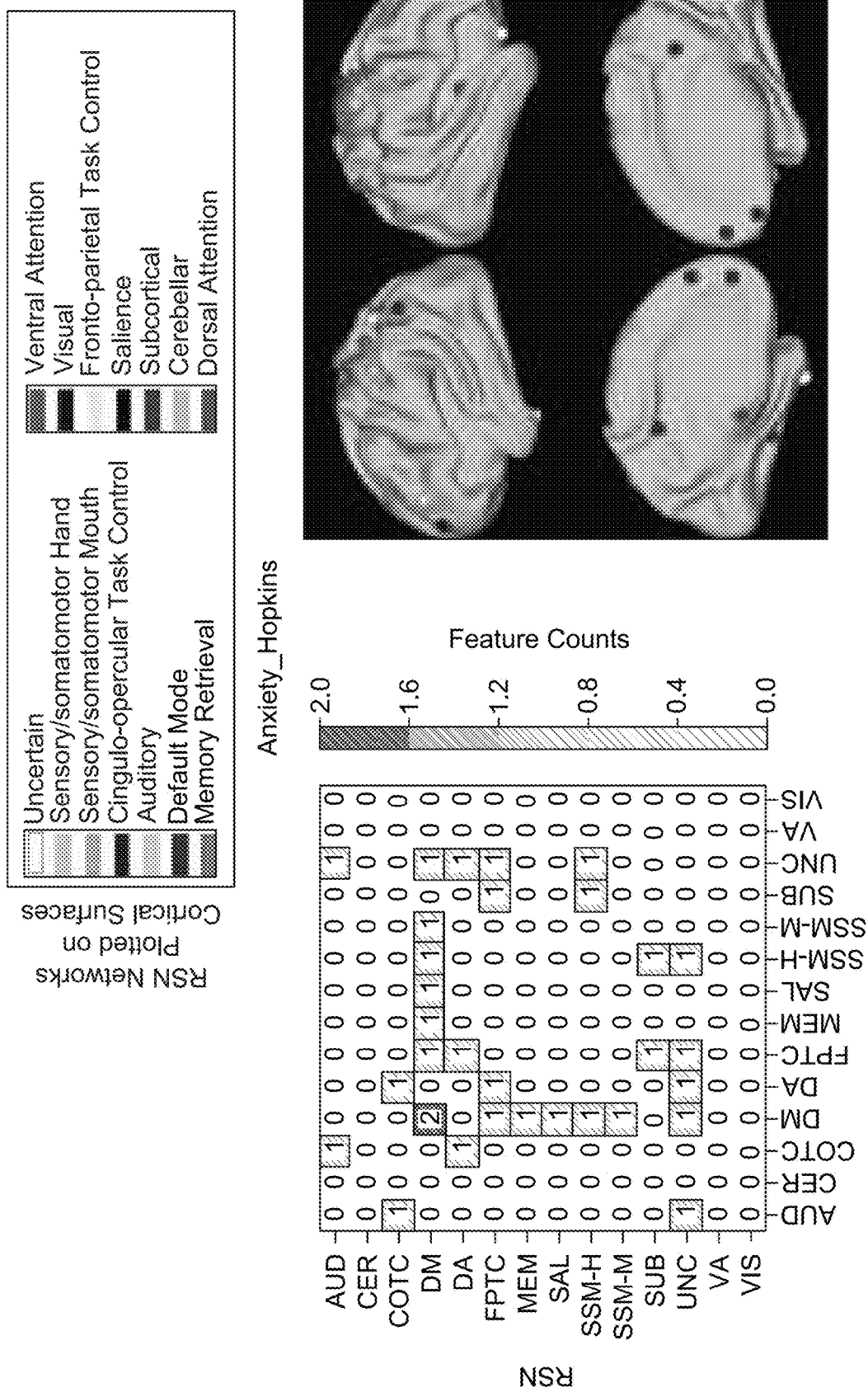

FIGS. 4A-4F show exemplary data for a proportion of features from each scale for the best model predicting mood, anhedonia, and anxiety. For example, FIGS. 4A-4B illustrate pie charts of exemplary proportions of features from each scale under dysregulated mood models; FIGS. 4C-4D illustrate pie charts of exemplary proportions of features from each scale under anhedonia models; and FIGS. 4E-4F illustrate pie charts of exemplary proportions of features from each scale under anxiety models. Of the features returned by the best model that were scale items, each pie chart shows the proportion of those items that were from the corresponding scales for the model for each outcome variable. For example, for the Mood/Dep_Hopkins model, 31% of the scale items were from the TCI scale, 6% from the Chaphyp scale, etc. This representation of features does not show the sign of the regression coefficient and whether predictive features indicate increasing or decreasing symptom severity.

FIGS. 5A-5F show connectivity matrices and ROI locations for fMRI connectivity features of best models predicting mood (FIGS. 5A-5B), anhedonia (FIGS. 5C-5D), and anxiety (FIGS. 5E-5F) outcome variables. For all non-zero fMRI connectivity features returned by the respective model, the number of individual edges between two nodes is plotted in the connectivity matrix (shown in the left plots of each of FIGS. 5A-5F) for that model. Each row and column represent a single resting-state network (RSN) from the Power atlas. Darker squares represent more features within or between the given networks with actual feature number superimposed numerically on each square. Connectivity matrices have the same RSNs listed on both axes, so upper and lower triangles show redundant information. Cortical surface plots (shown in the right plots of each of FIGS. 5A-5F) show the ROI locations marked by RSN membership for each model to display the breadth of networks with informative features for each model. Because only cortical surfaces are shown, no cerebellar nodes were plotted in the brain plots. Network labels are AUD: Auditory, CER: Cerebellar, COTC: Cingulo-opercular Task Control, DM: Default Mode, DA: Dorsal Attention, FPTC: Fronto-parietal Task Control, MEM: Memory Retrieval, SAL: Salience, SSM-H: Sensory/somatomotor Hand, SSM-M: Sensory/somatomotor Mouth, SUB: Subcortical, UNC: Uncertain (i.e., miscellaneous regions not assigned to a specific RSN), VA: Ventral Attention, VIS: Visual.

Figure 6A:
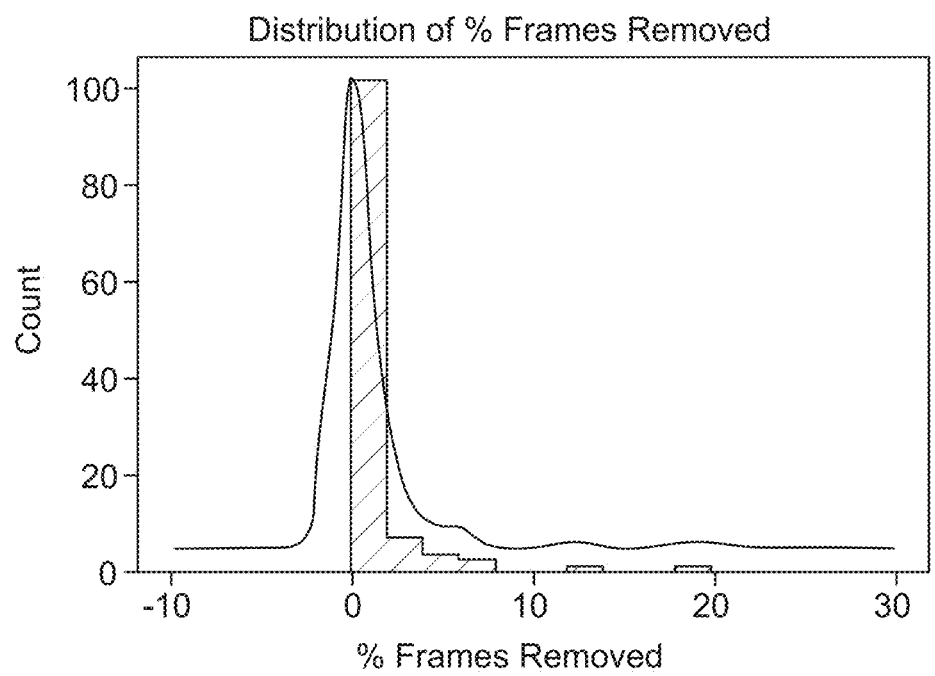
FIGS. 6A-6I illustrate distributions of in-scanner motion measurements, having scales data, sMRI data, and fMRI data as input, according to some implementations of the present disclosure.
Figure 6B:
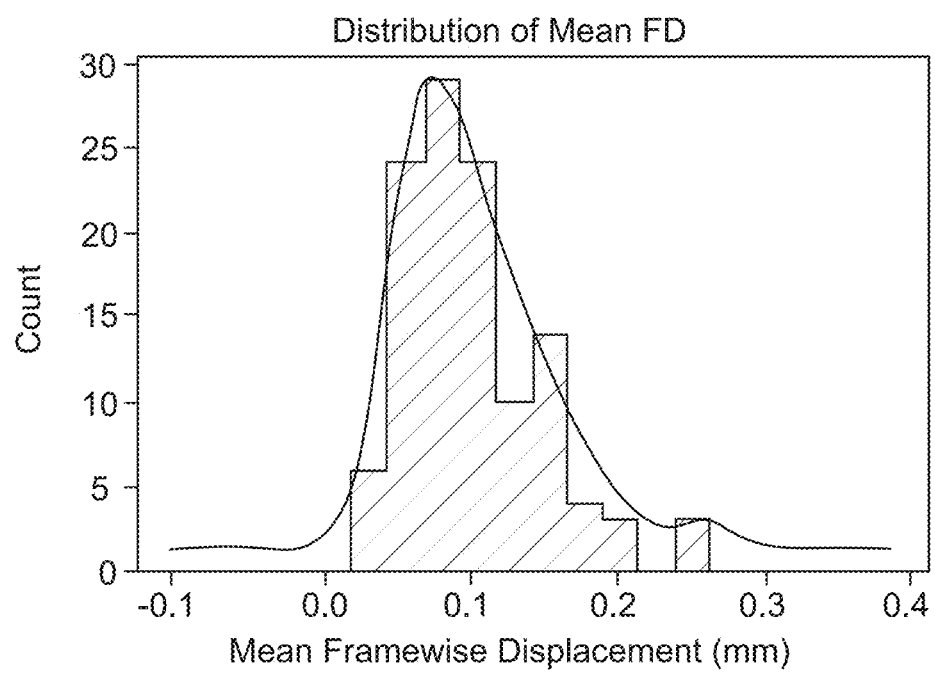
Figure 6C:
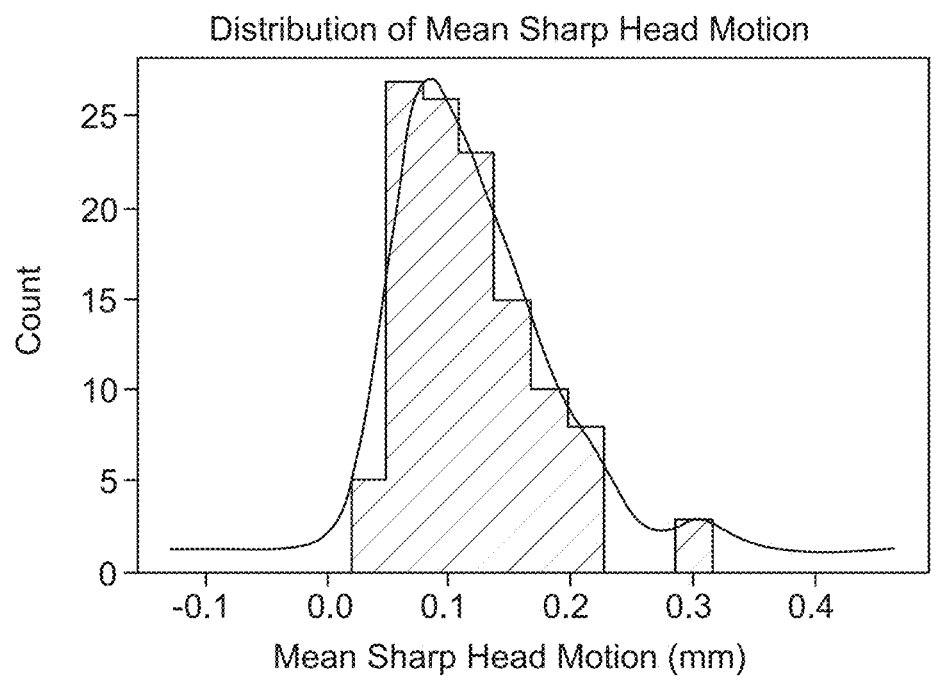
Figure 6D:
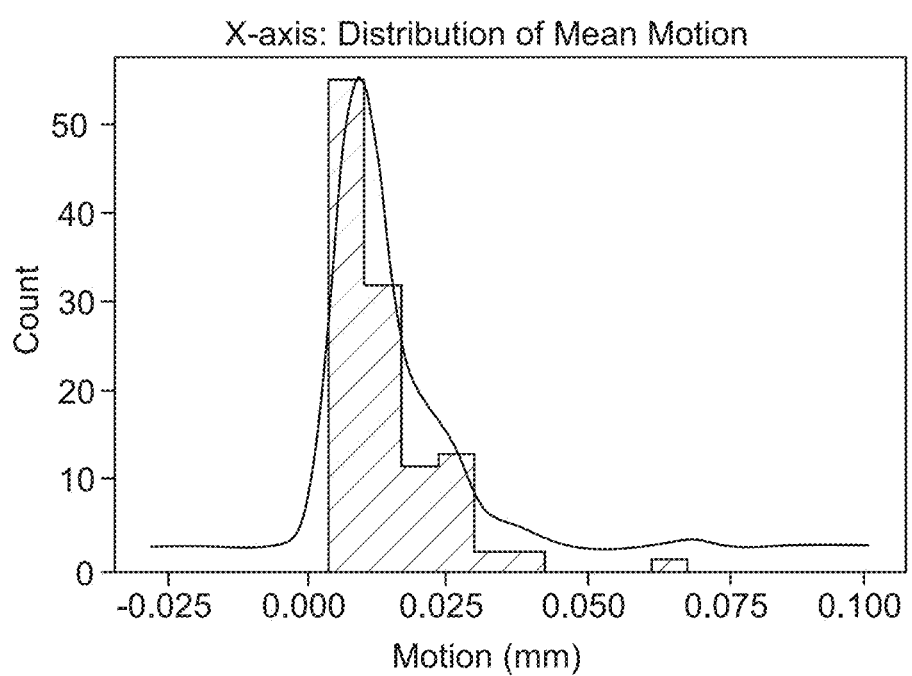
Figure 6E:
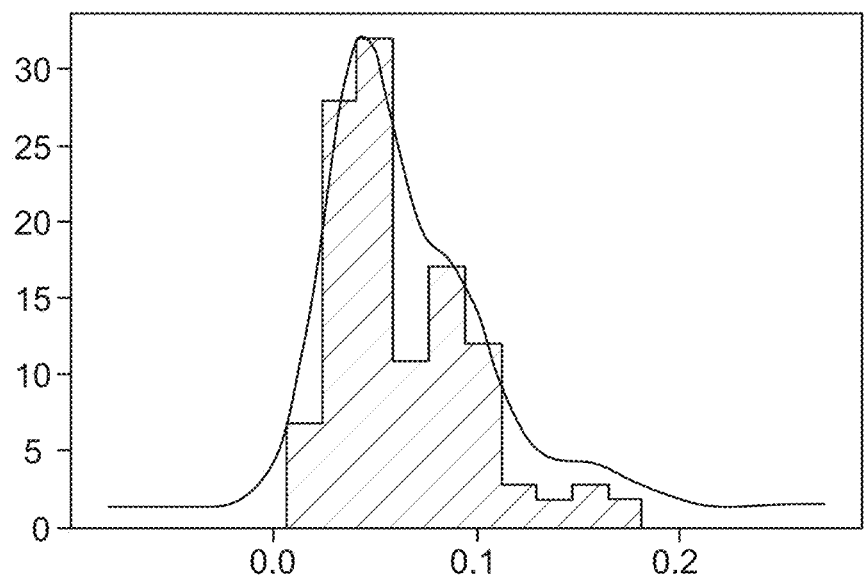
Figure 6F:
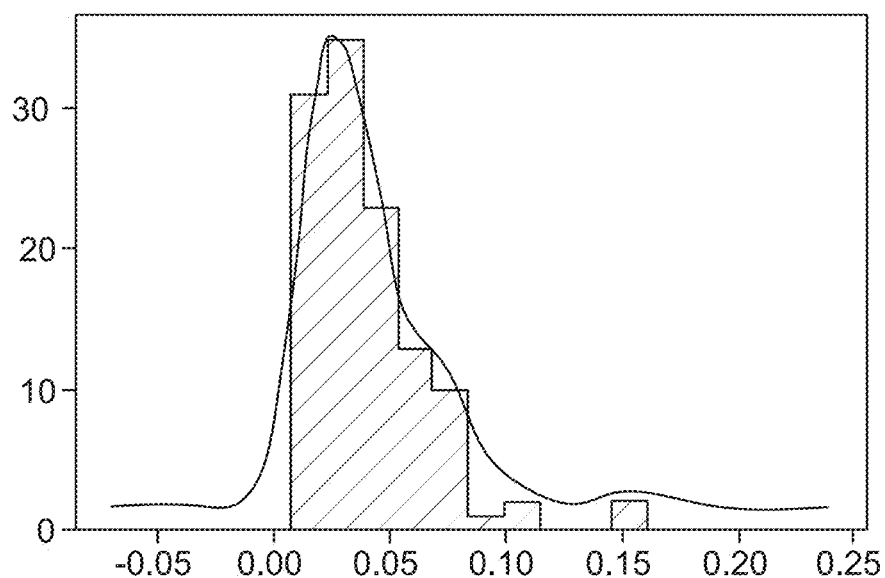
Figure 6G:
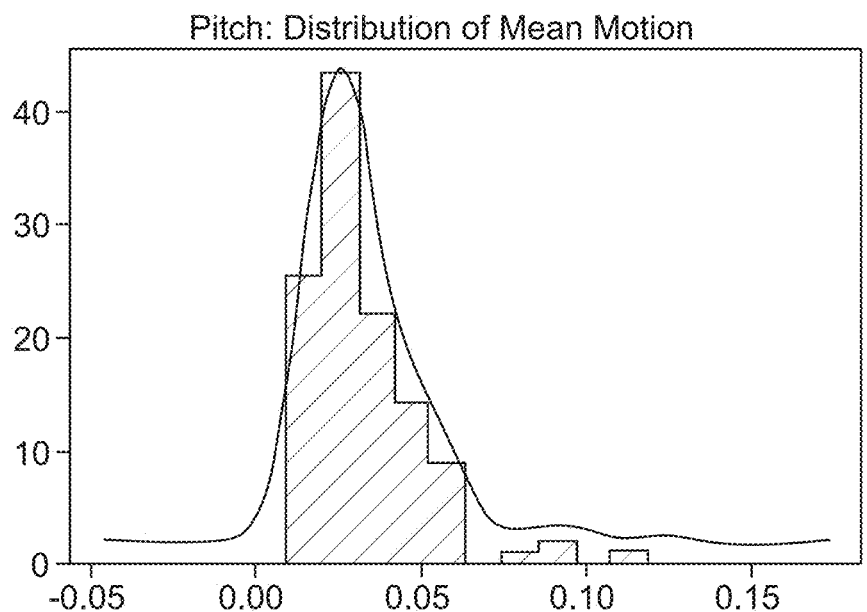
Figure 6H:
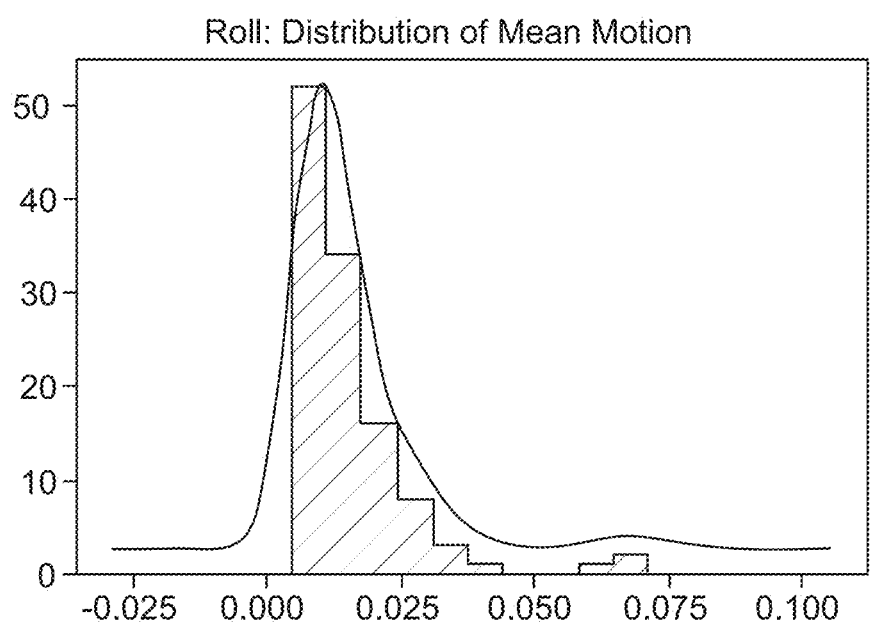
Figure 6I:
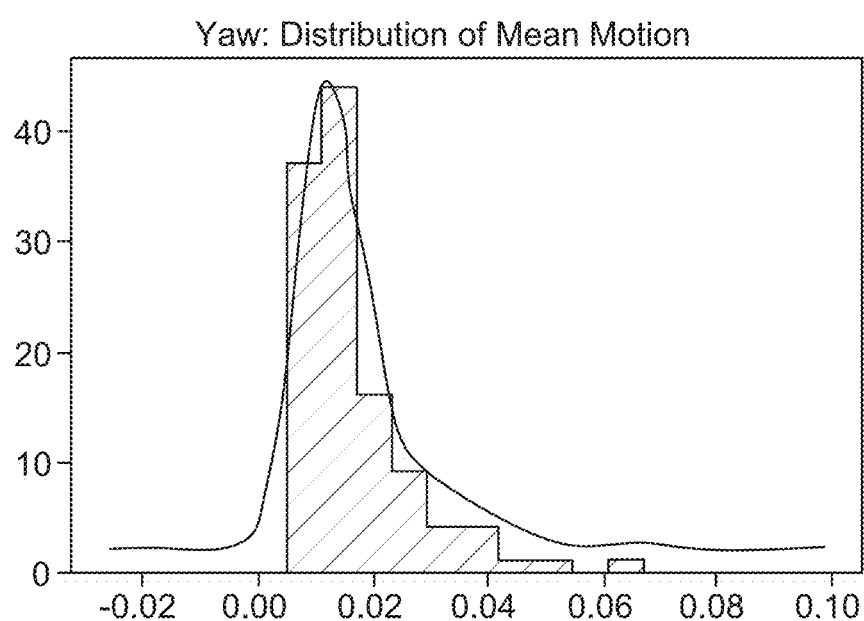

The models with the least complexity are scales-only models shown in FIGS. 6A-6I. FIGS. 6A-6I shows distributions of the scales+sMRI+fMRI cohort's in-scanner motion measurements. FIG. 6A shows percentage of frames that exceeded 0.5 mm. FIG. 6B shows mean framewise displacement (FD). FIG. 6C mean sharp head motion. FIGS. 6D-6I show mean of motion for each of six motion parameters—x-direction, y-direction, z-direction, pitch, roll, and yaw. Each plot displays the histogram with a Gaussian kernel density estimated distribution superimposed.

Figure 7A:
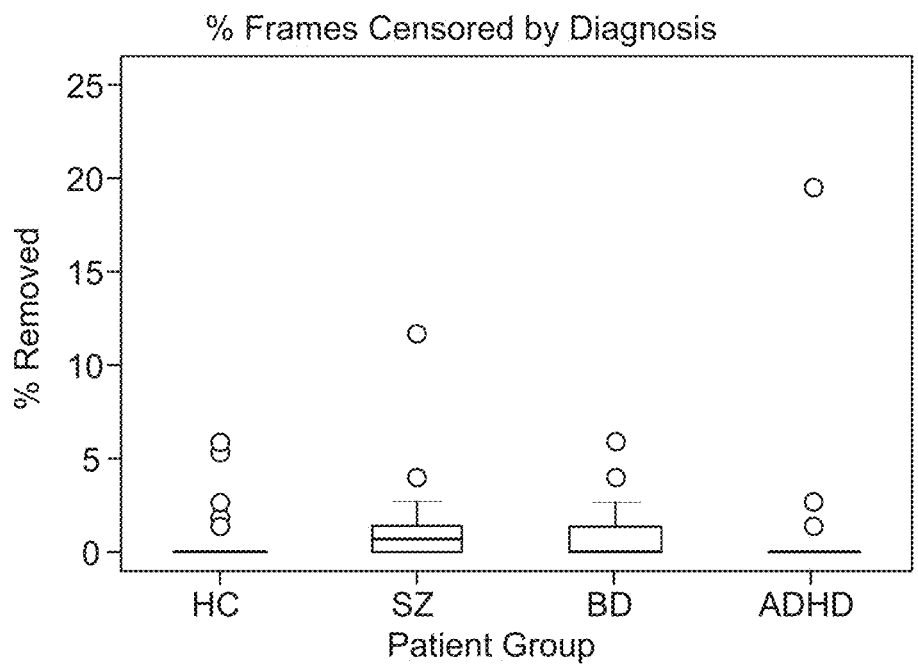
FIGS. 7A-7I illustrate comparisons of in-scanner motion measurements, having scales data, sMRI data, and fMRI data as input, and grouped by diagnoses, according to some implementations of the present disclosure.
Figure 7B:
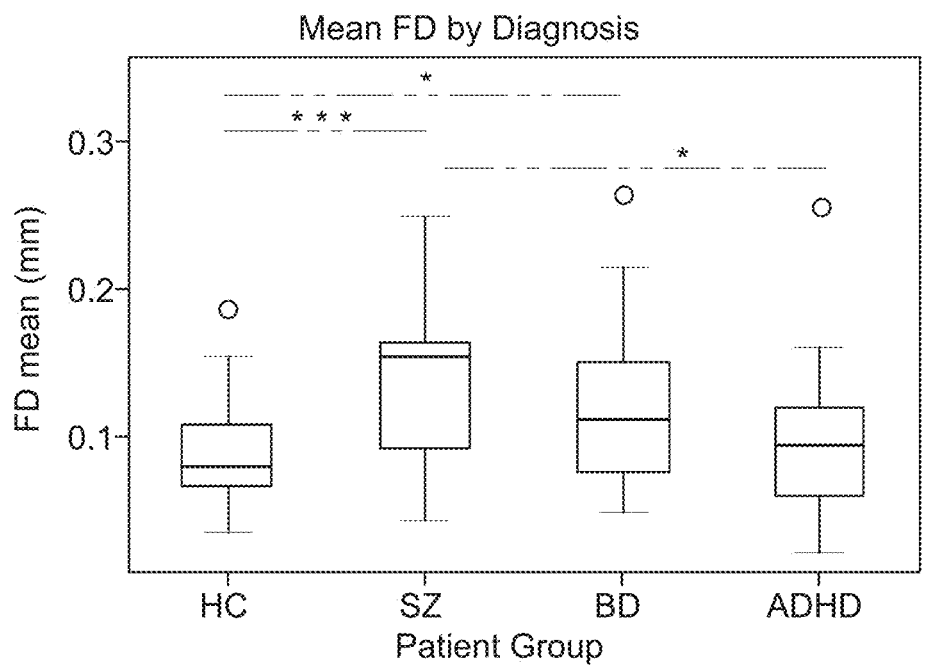
Figure 7C:
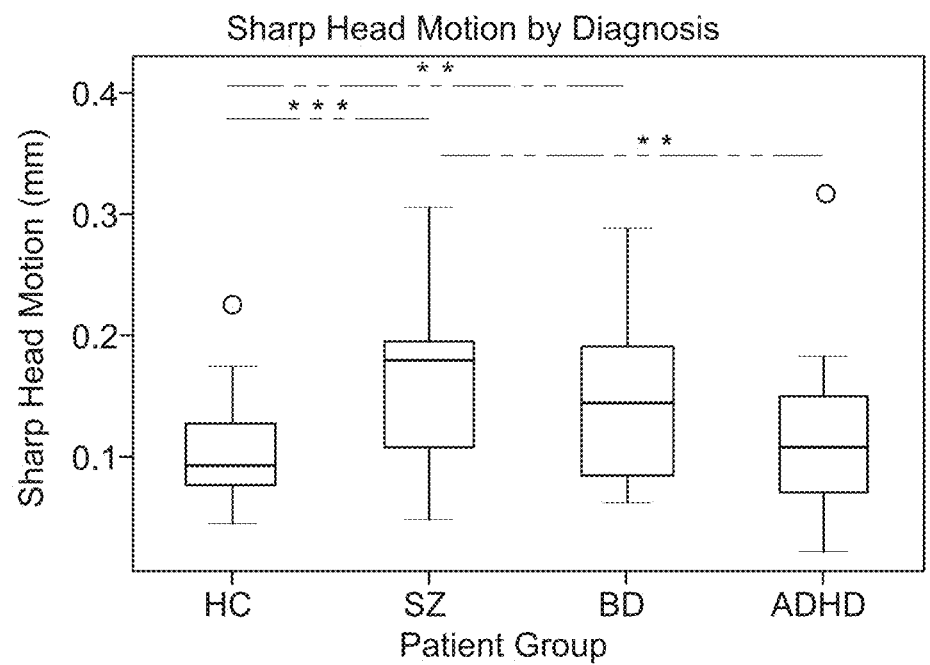
Figure 7D:
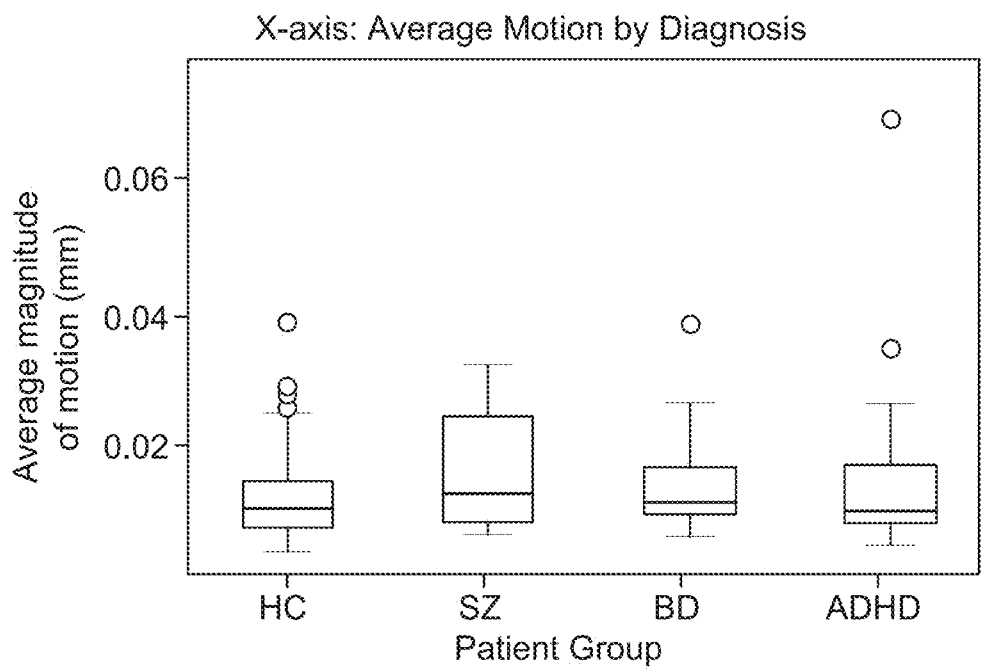
Figure 7E:
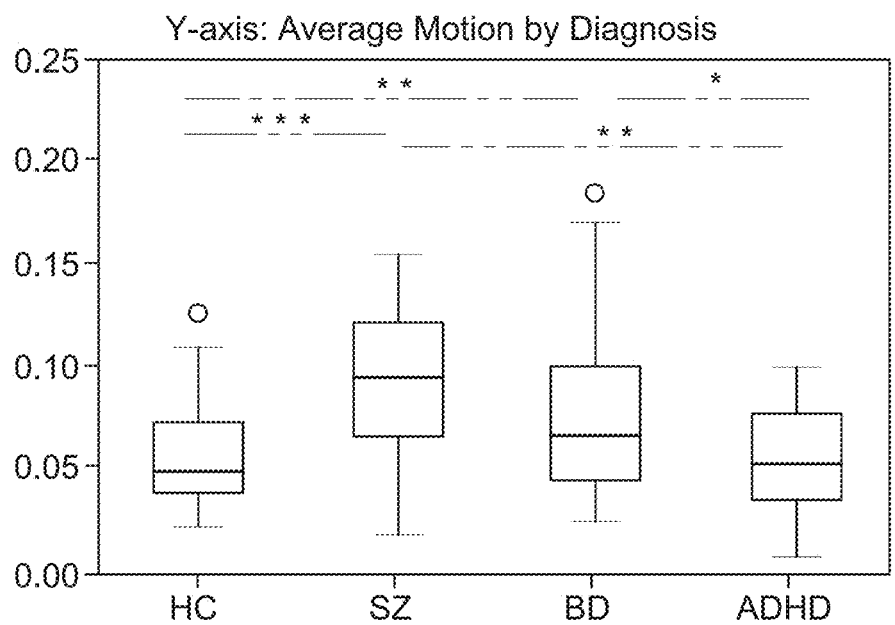
Figure 7F:
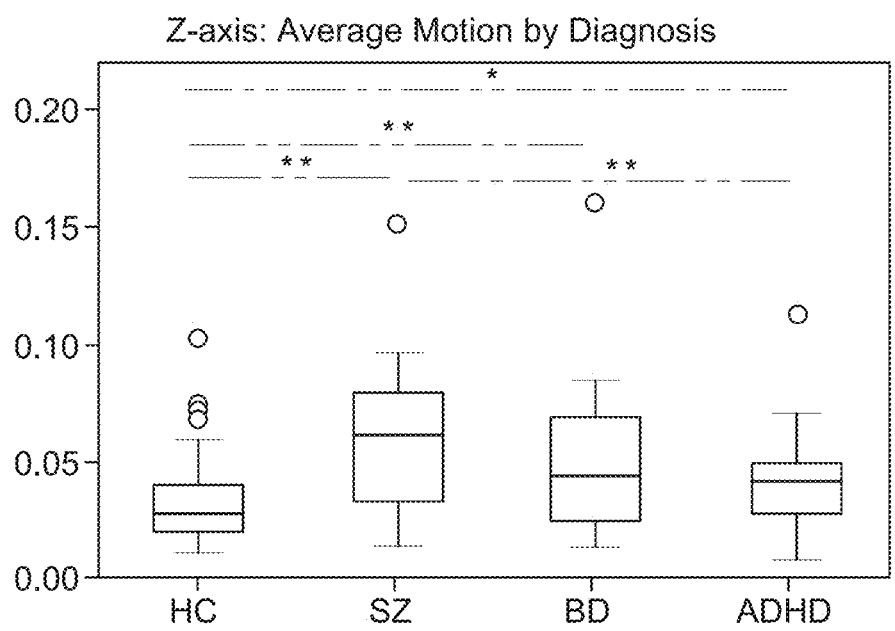
Figure 7G:
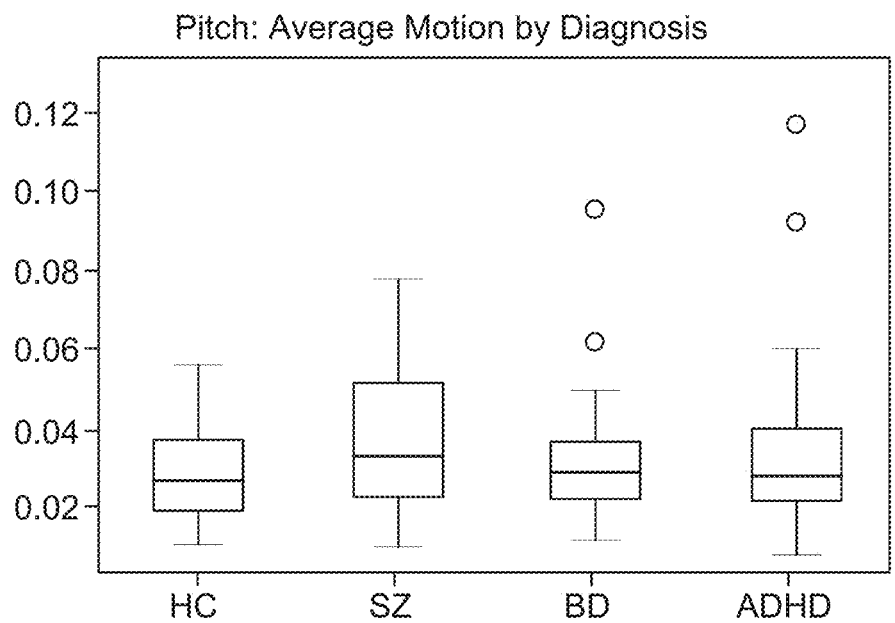
Figure 7H:
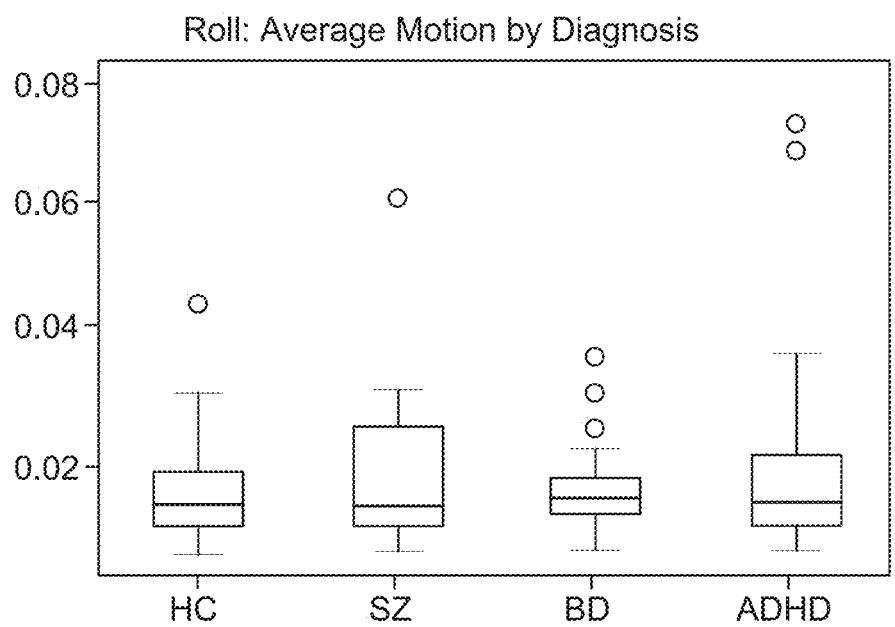
Figure 7I:
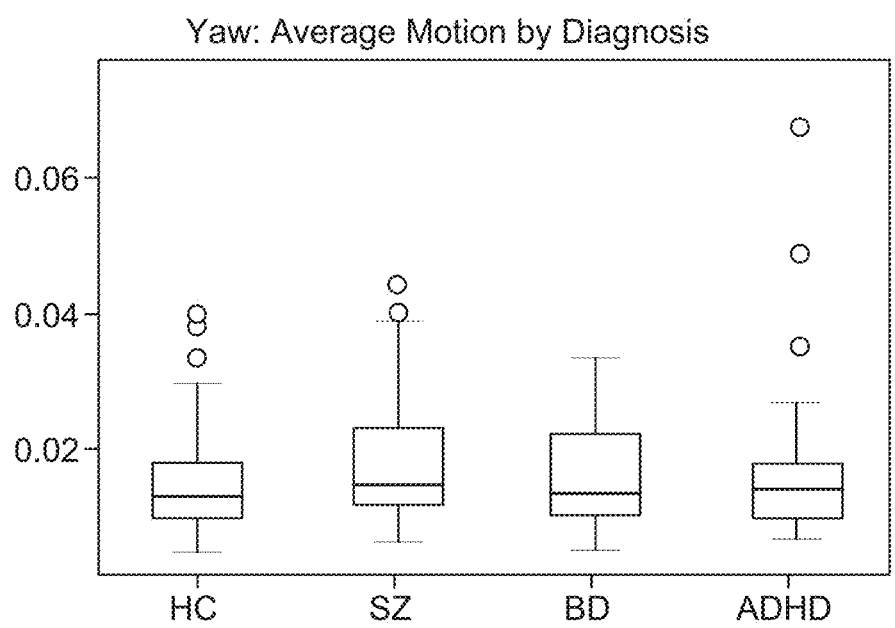

FIGS. 7A-7I shows comparisons of in-scanner motion measurements for the scales data, sMRI data, and fMRI data as input, grouped by diagnosis, according to an exemplary methodology of the present disclosure. FIG. 7A shows box plots of percentage of frames that exceeded 0.5 mm. FIG. 7B shows mean framewise displacement (FD). FIG. 7C shows mean sharp head motion. FIGS. 7D-7I show mean of motion for each of six motion parameters—x-direction, y-direction, z-direction, pitch, roll, and yaw. For those group comparisons that yielded significant differences on Kruskal Wallis tests (see Supplementary text), post hoc pairwise Wilcoxon rank-sum tests were performed and indicated with stars. Significantly different comparisons are indicated with * for $p<0.05$,  for $p<0.01$, and * for $p<0.001$.

Figure 8A:
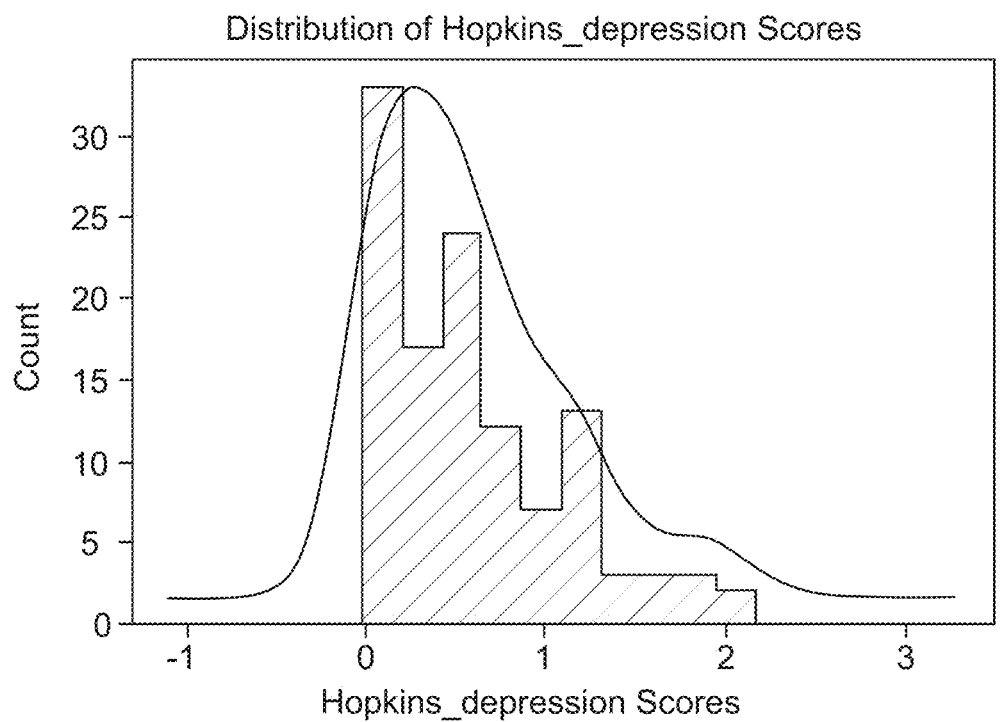
FIGS. 8A-8C illustrate distributions of outcome measures, having scales data, sMRI data, and fMRI data as input, according to some implementations of the present disclosure.
Figure 8A:
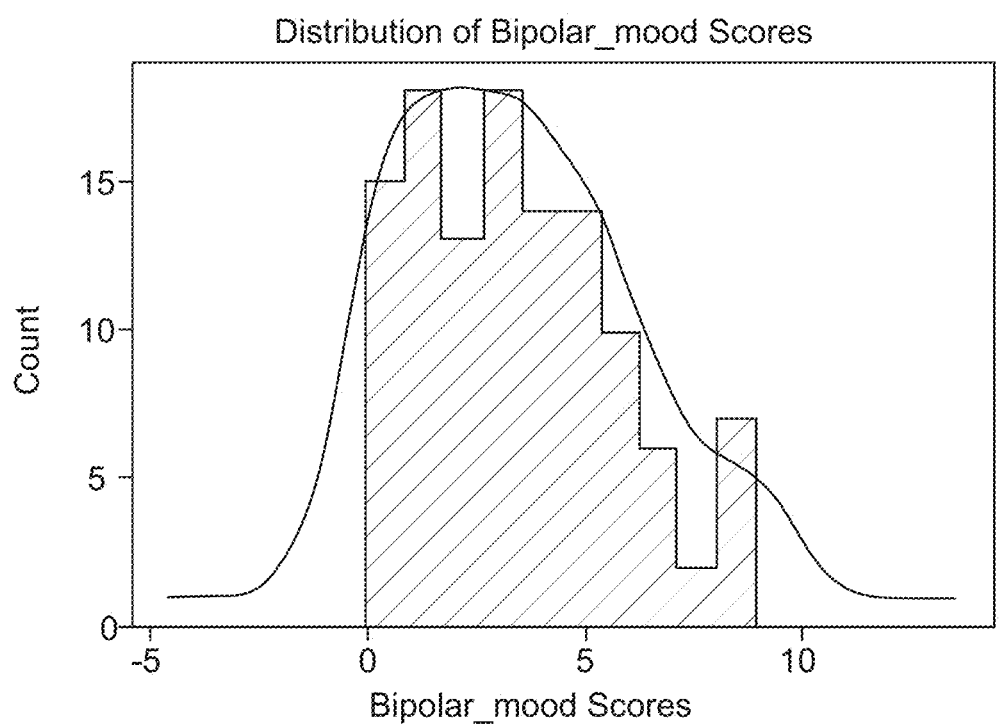
Figure 8B:
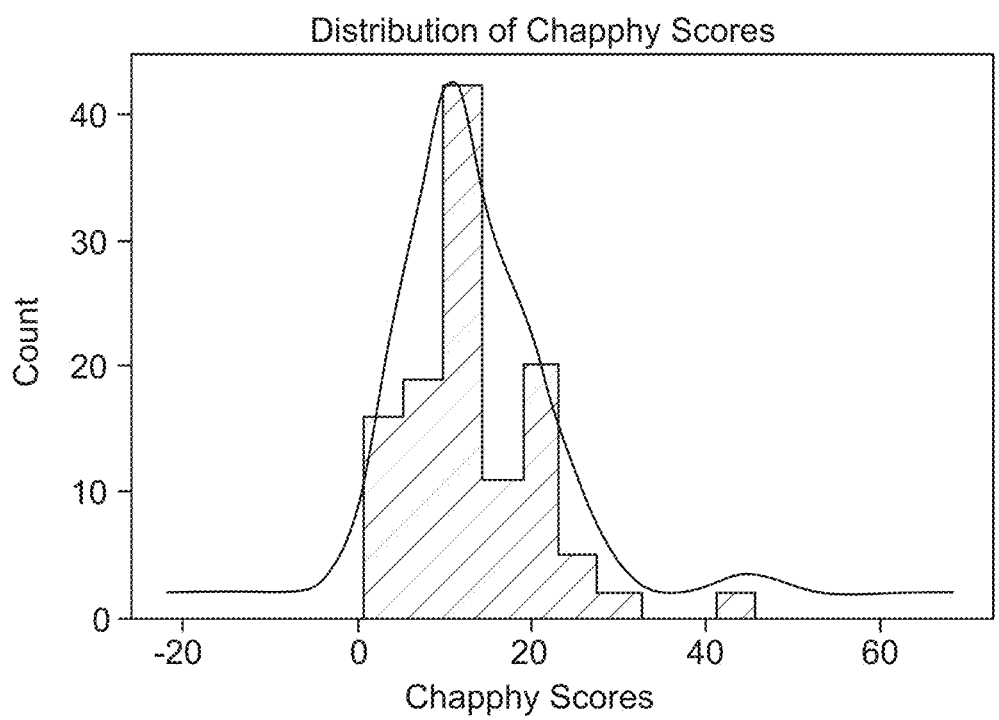
Figure 8B:
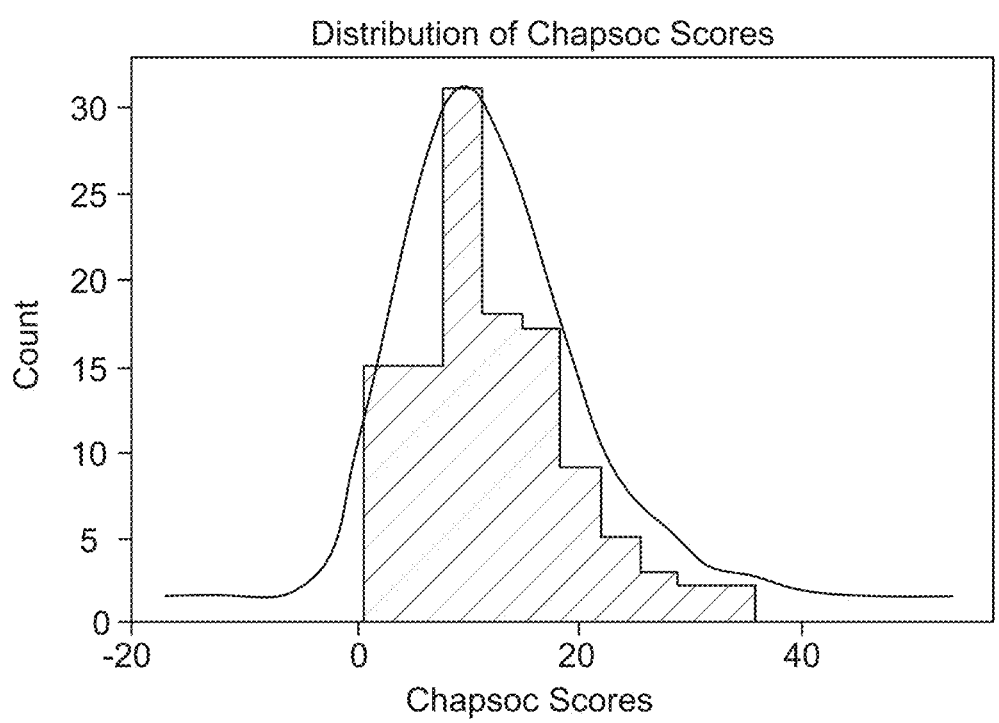
Figure 8C:
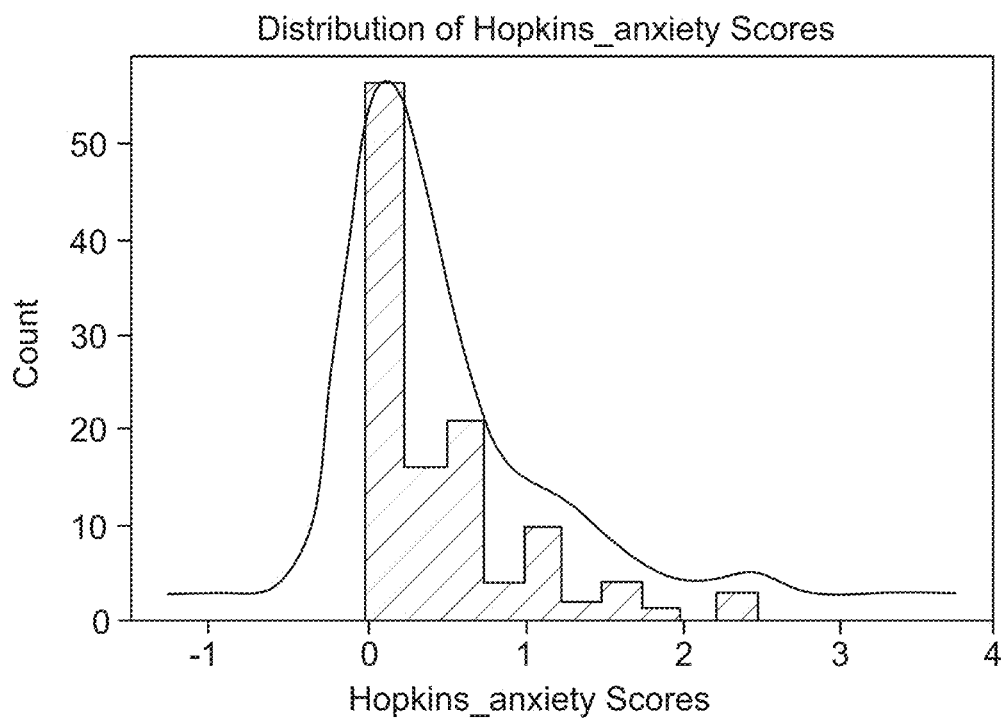
Figure 8C:
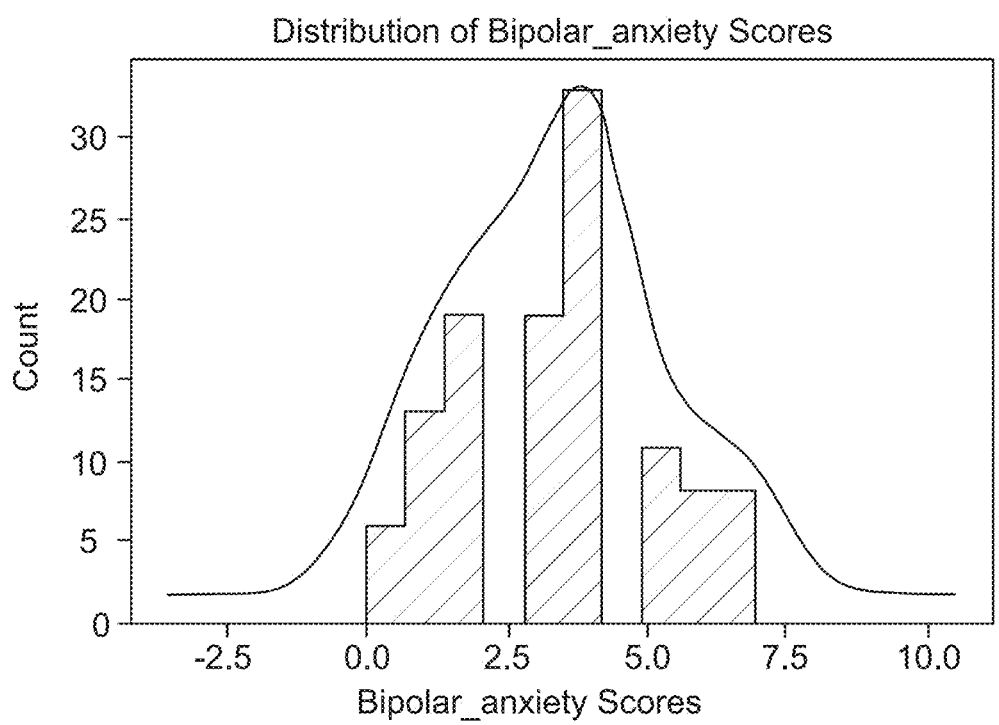

FIGS. 8A-8C show distributions of outcome measures for scales data, sMRI data, and fMRI data as input. FIG. 8A shows dysregulated mood models, Hopkins_depression and Bipolar_mood scores. FIG. 8B shows anhedonia models, Anhedonia_Chapphy and Anhedonia_Chapsoc scores. FIG. 8C shows anxiety models, Hopkins_anxiety and Bipolar_anxiety scores. Each plot displays the histogram with a Gaussian kernel density estimated distribution superimposed.

Figure 10A:
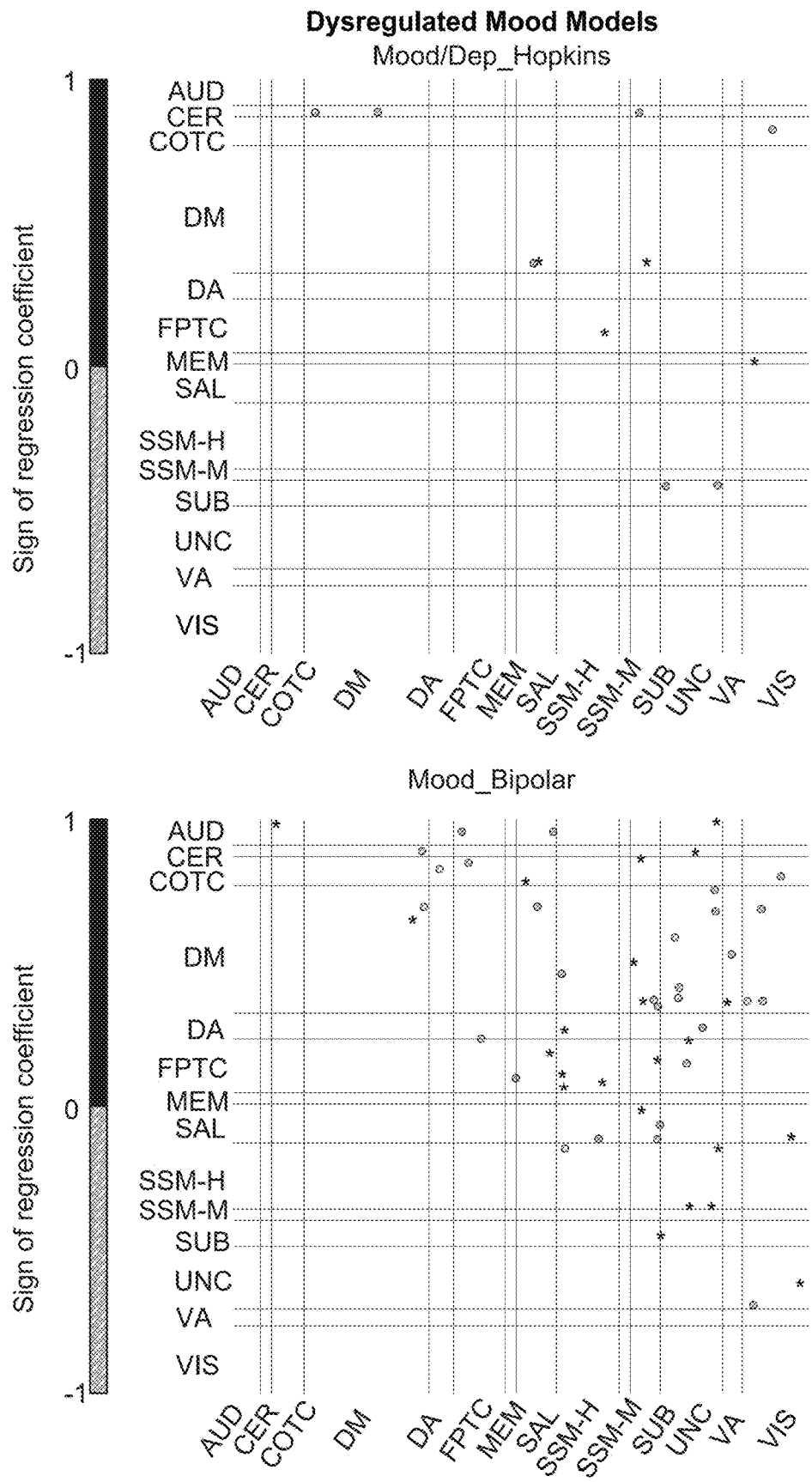
FIG. 10A illustrates binary heat maps for fMRI connectivity features under dysregulated mood models, according to some implementations of the present disclosure.
Figure 10B:
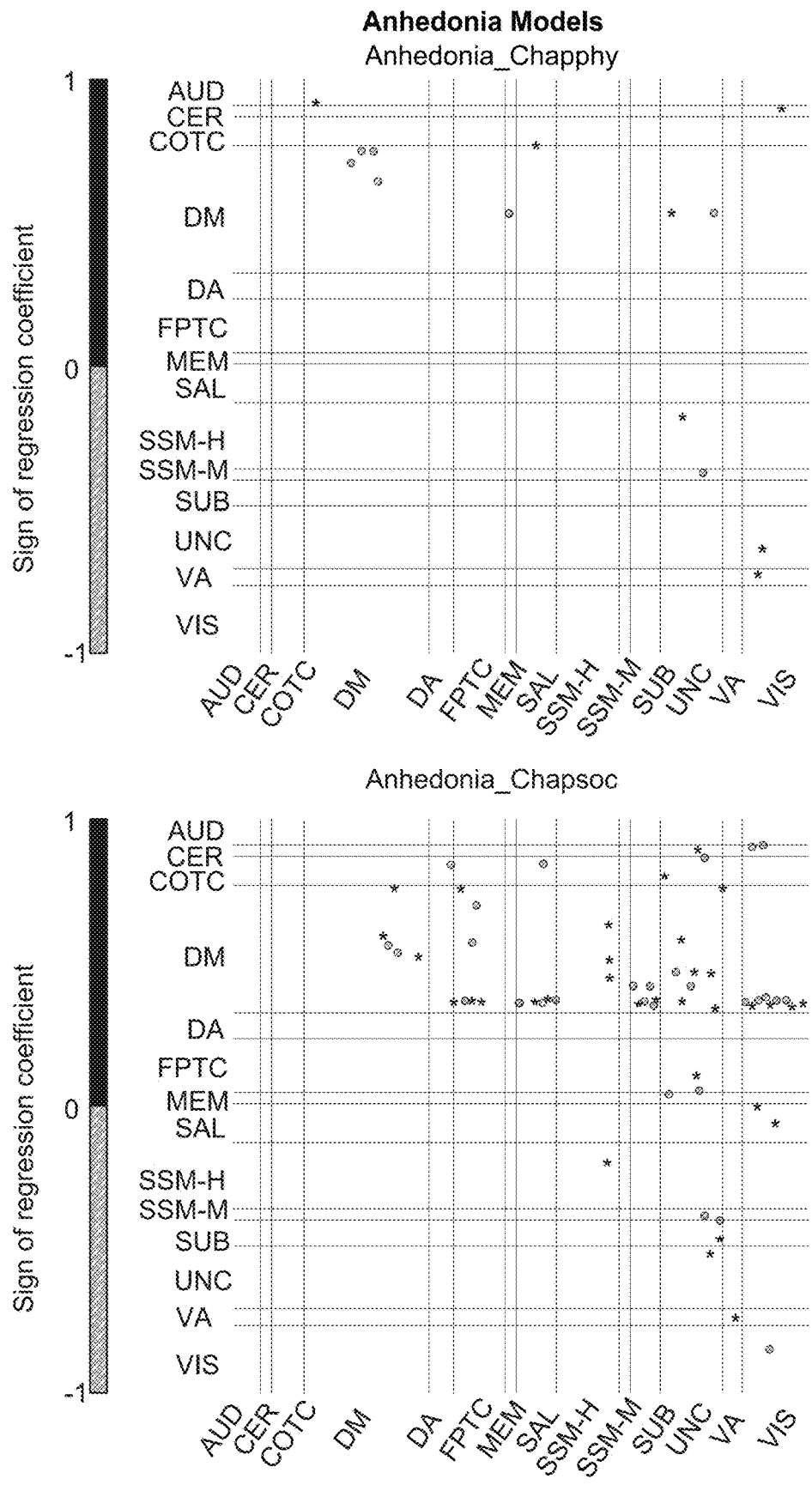
FIG. 10B illustrates binary heat maps for fMRI connectivity features under anhedonia models, according to some implementations of the present disclosure.
Figure 10C:
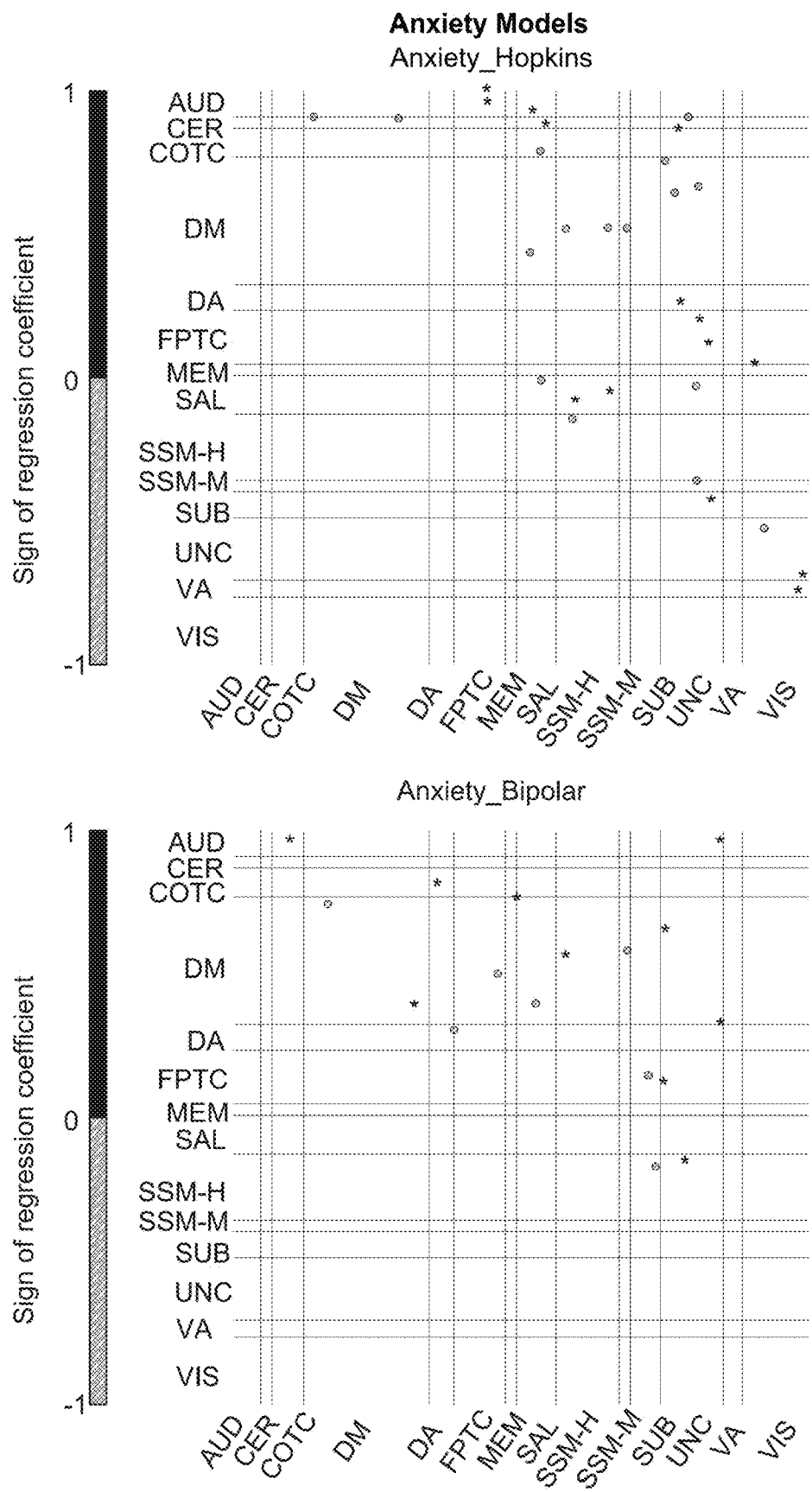
FIG. 10C illustrates binary heat maps for fMRI connectivity features under anxiety models, according to some implementations of the present disclosure.

Referring now to FIGS. 10A-10C, binary heat maps for fMRI connectivity features of a best model, are shown. For example, FIG. 10A illustrates binary heat maps for fMRI connectivity features under dysregulated mood models; FIG. 10B illustrates binary heat maps for fMRI connectivity features under anhedonia models; and FIG. 10C illustrates binary heat maps for fMRI connectivity features under anxiety models. For all non-zero fMRI connectivity features returned by the respective model, the regression coefficients for each individual edge between two nodes is plotted in the connectivity matrix for that model. Each row and column represents a single ROI from the Power atlas, ordered consistently in both directions. Coefficients have been binarized (positive plotted as stars, negative as dots) for easier viewing of sparse matrices. Upper and lower triangles show redundant information, so only upper triangles are plotted. Lines delineate intrinsic resting state networks for easier visualization of network category for each feature. Network labels are AUD: Auditory, CER: Cerebellar, COTC: Cingulo-opercular Task Control, DM: Default Mode, DA: Dorsal Attention, FPTC: Fronto-parietal Task Control, MEM: Memory Retrieval, SAL: Salience, SSM-H: Sensory/somatomotor Hand, SSM-M: Sensory/somatomotor Mouth, SUB: Subcortical, UNC: Uncertain (i.e., miscellaneous regions not assigned to a specific RSN), VA: Ventral Attention, VIS: Visual.

Figure 11A:
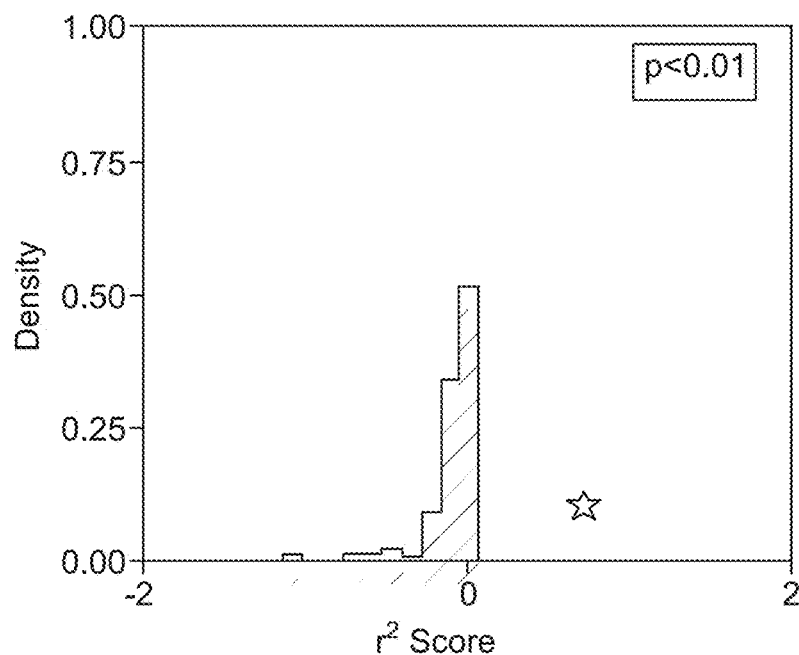
FIGS. 11A-11B illustrate results of permutation tests under dysregulated mood models, according to some implementations of the present disclosure.
Figure 11B:
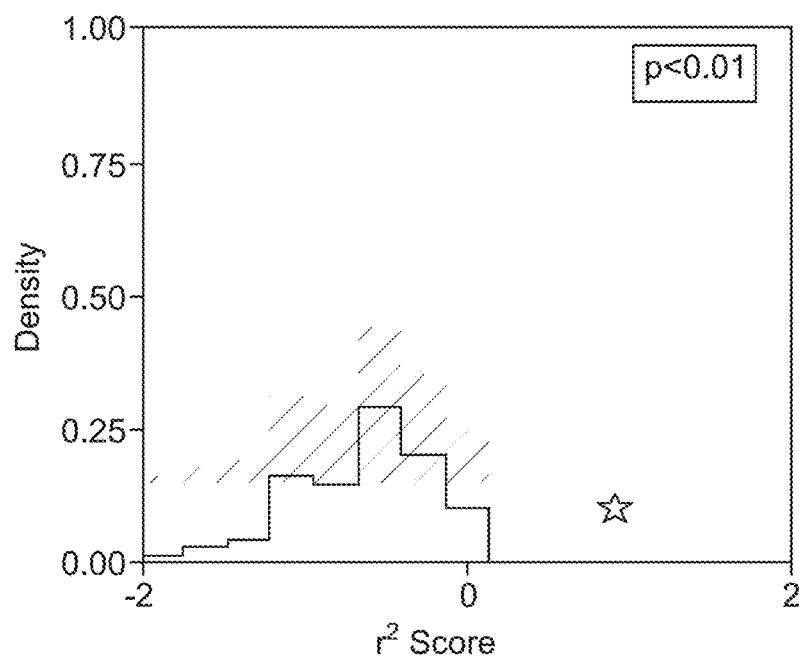
Figure 11C:
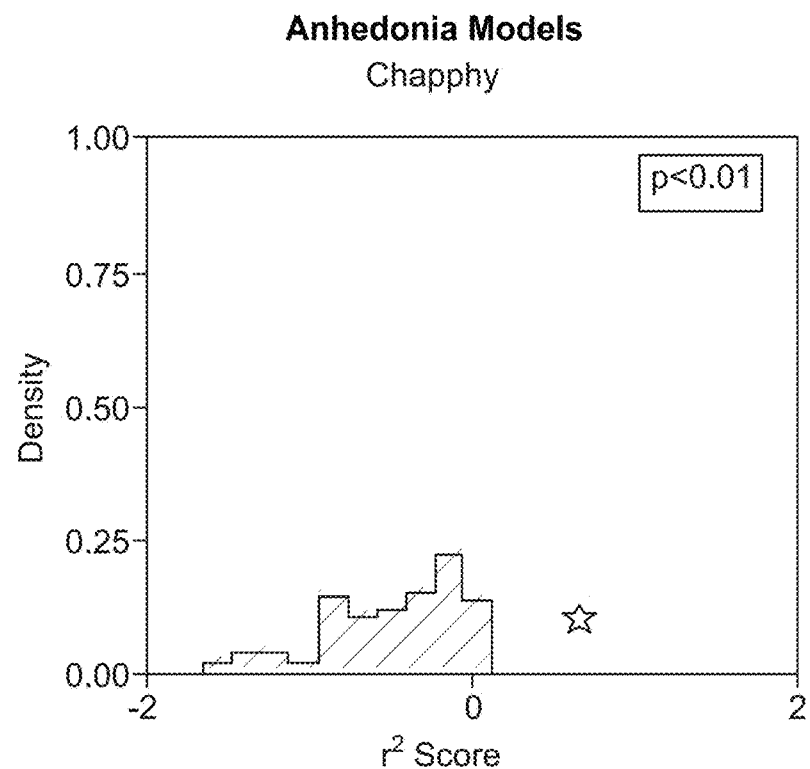
FIGS. 11C-11D illustrate results of permutation tests under anhedonia models, according to some implementations of the present disclosure.
Figure 11D:
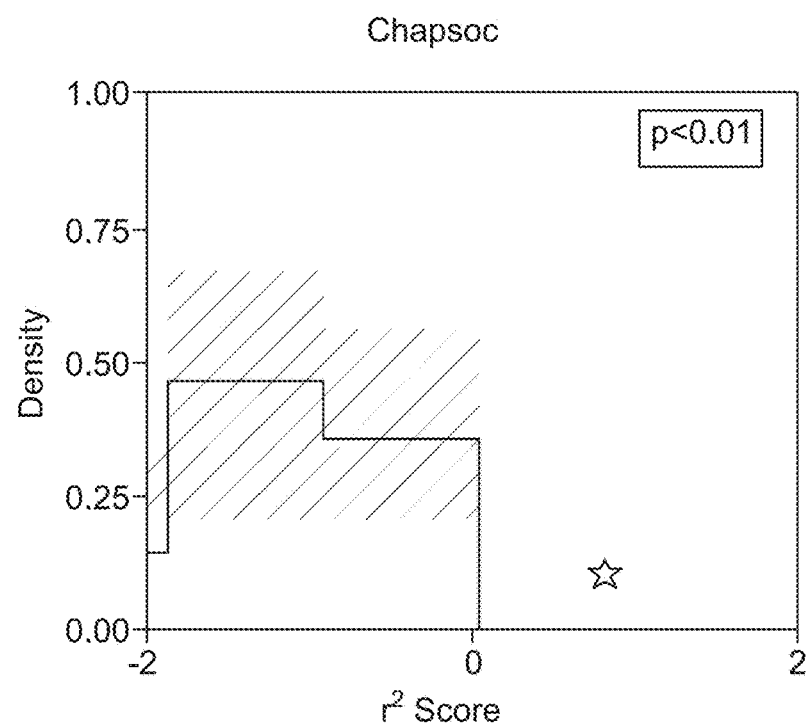
Figure 11E:
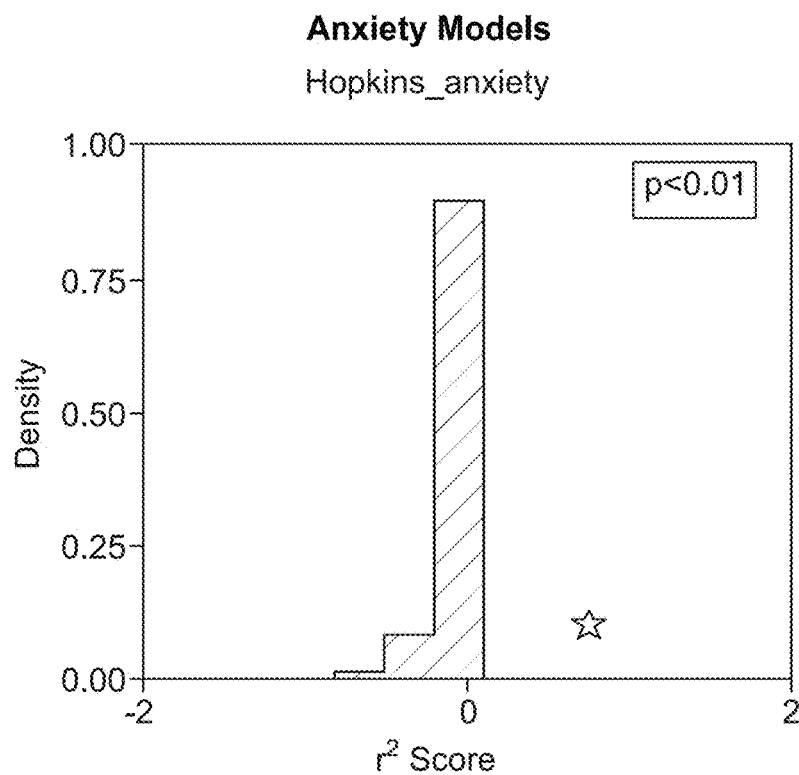
FIGS. 11E-11F illustrate results of permutation tests under anxiety models, according to some implementations of the present disclosure.
Figure 11F:
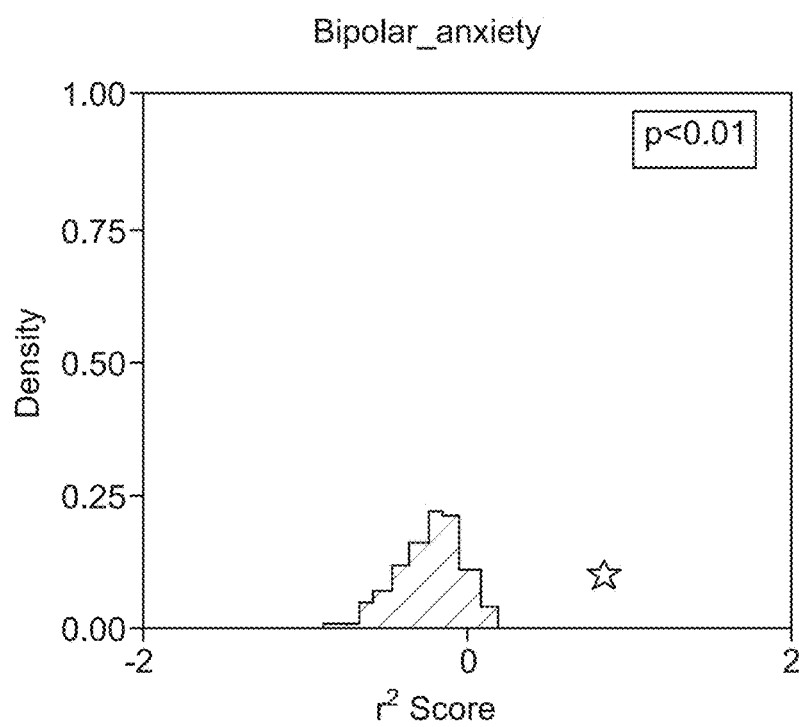

FIGS. 11A-11F show results of permutation tests of the alternative hypothesis that the best model results were significantly greater than the baseline model results (where the outcome variable scores were permuted across subjects). For example, FIGS. 11A-11B illustrate results of permutation tests under dysregulated mood models; FIGS. 11C-11D illustrate results of permutation tests under anhedonia models; and FIGS. 11E-11F illustrate results of permutation tests under anxiety models. One hundred (100) permuted models were used to generate the empirical distribution of $r^2$ values, and the $r^2$ value of the best model is shown with the star. Distributions extended below negative two (−2) $r^2$ in some models, but all models are shown on the same x- and y-scales for ease of comparison. All six models had p<0.01.

Figure 12A:
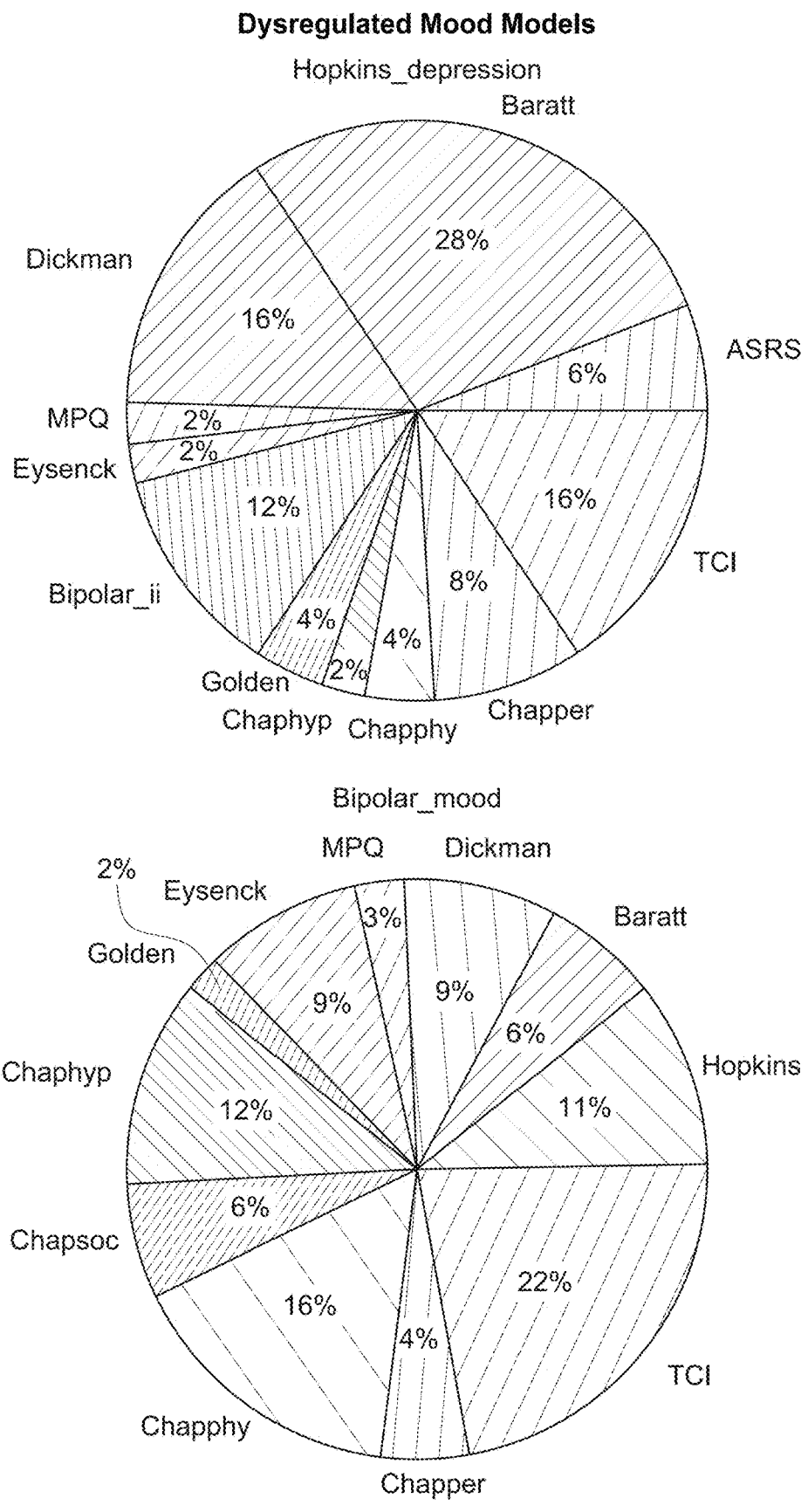
FIG. 12A illustrates proportions of features from each scale having clinical scales data only as input under dysregulated mood models, according to some implementations of the present disclosure.
Figure 12B:
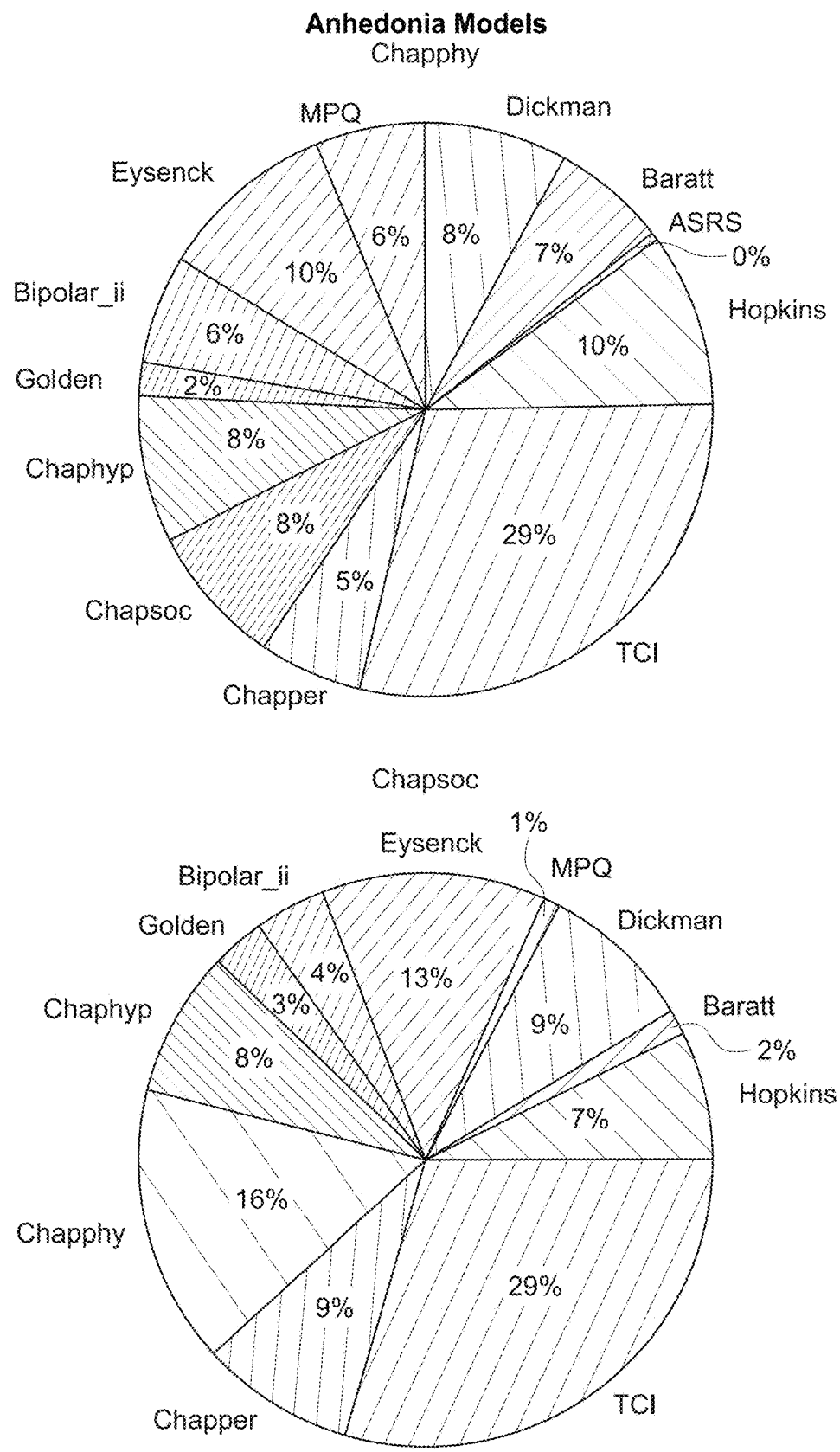
FIG. 12B illustrates proportions of features from each scale having clinical scales data only as input under anhedonia models, according to some implementations of the present disclosure.
Figure 12C:
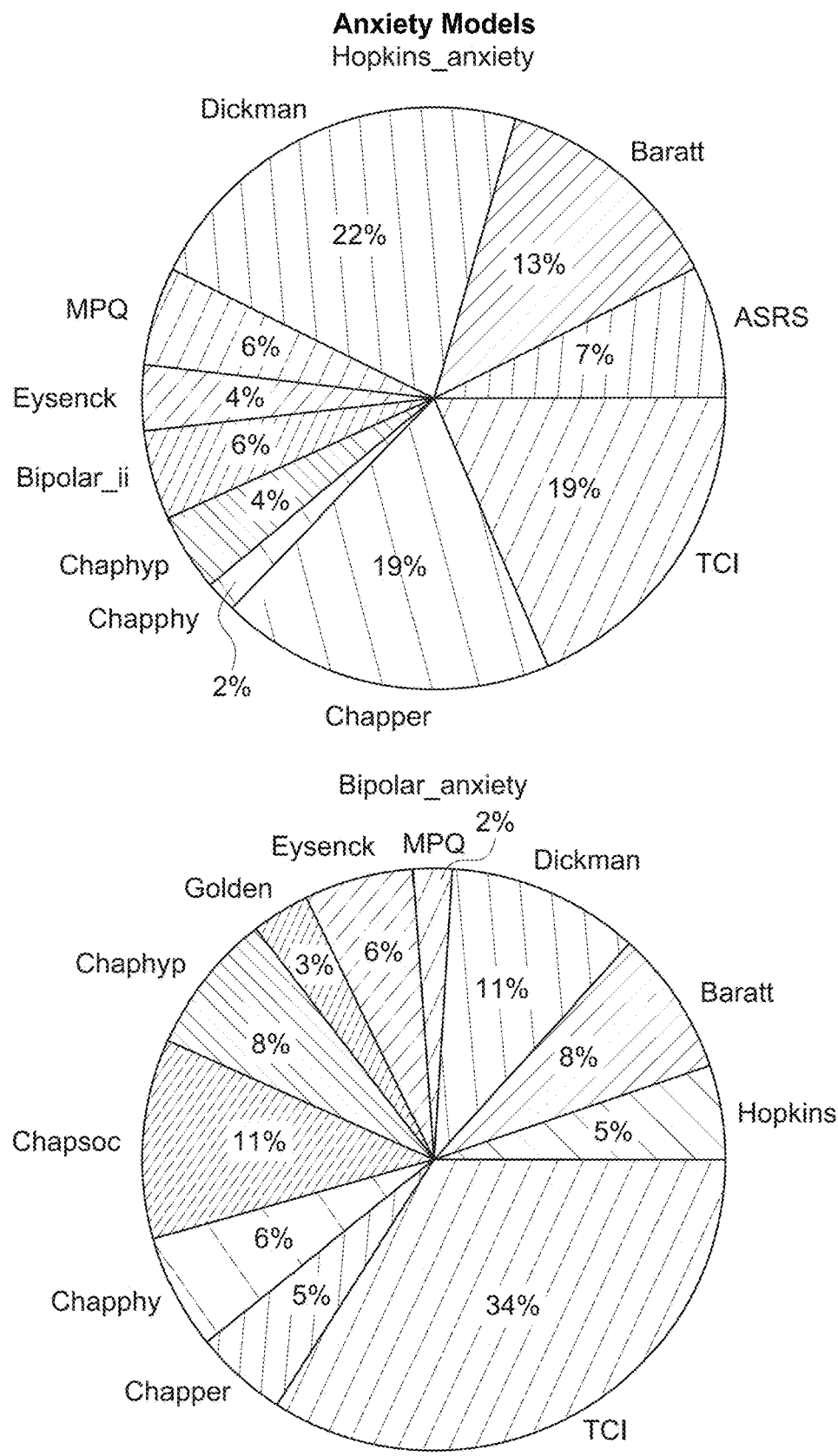
FIG. 12C illustrates proportions of features from each scale having clinical scales data only as input under anxiety models, according to some implementations of the present disclosure.

FIGS. 12A-12C show the proportion of features from each scale for the clinical scales data only as input, according to an exemplary methodology of the present disclosure. For example, FIG. 12A illustrates proportions of features from each scale having clinical scales data only as input under dysregulated mood models; FIG. 12B illustrates proportions of features from each scale having clinical scales data only as input under anhedonia models; and FIG. 12C illustrates proportions of features from each scale having clinical scales data only as input under anxiety models. The model displayed in FIGS. 12A-12C used Elastic Net with the median $r^2$ value.

Figure 13:
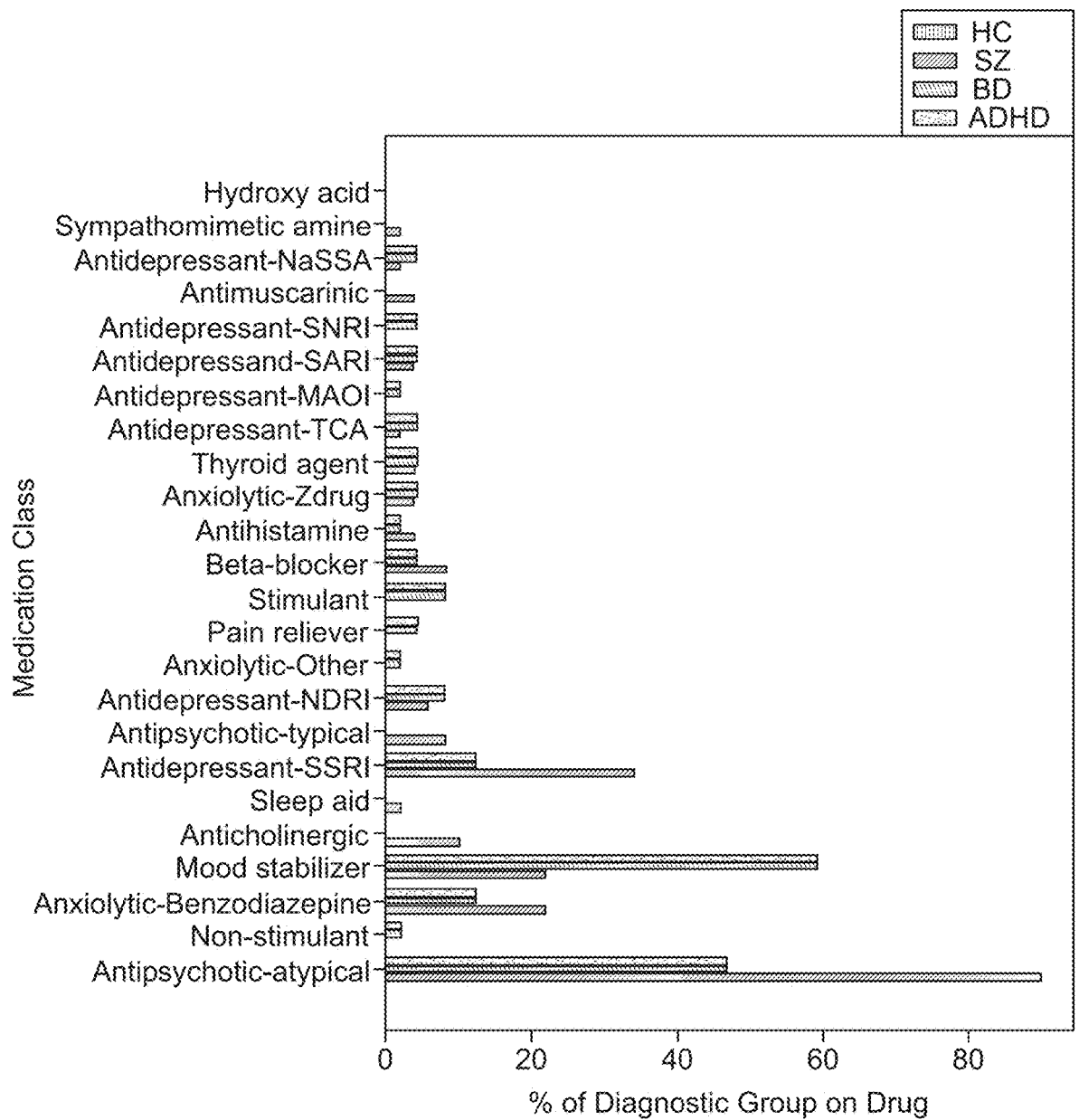
FIG. 13 illustrates current medication usage status, grouped by medication class, for groups of participants, according to some implementations of the present disclosure.

FIG. 13 shows current medication usage status, grouped by medication class, for groups of participants, according to an exemplary methodology of the present disclosure. Each bar represents the percent of a diagnostic group that was using a stable medication of that particular class. Some diagnostic groups did not have any subjects using medications from a particular class. No healthy control (HC) subjects were on psychiatric medications per enrollment criteria.

Contributions of Scale Assessments and fMRI Connectivity Features to Models

In some examples of the present disclosure, rs-fMRI features can be grouped according to intrinsic RSN membership. These networks partially overlap with a proposed taxonomy of symptom-related networks in a focused set of brain regions as known in the prior art. By contrast to conventional research, the systems and methods of the present disclosure identify that these highly-predictive features are distributed across elements of many networks. The wide set of RSNs reflects the relatively wide nature of scale-based symptom constructs in contrast to the targeting allowed by finely-tuned behavioral tasks. It may also reflect a compilation of different mechanisms across theoretical subgroups of patients with differing brain dysregulation. Ultimately, the present disclosure provides systems and methods indicating that whole-brain connectivity between individual nodes is useful when creating models; this whole-brain connectivity is different from relying solely upon summary metrics of networks such as graph theory metrics, independent components, or more circumscribed ROI approaches to connectivity (these approaches are commonly used in the prior art). Specifically, anhedonia models of the present disclosure found not only elements of a reward circuit but also multiple nodes in the DM, Salience (SAL), Cingulo-Opercular Task Control (COTC), Fronto-Parietal Task Control (FPTC), and Visual (VIS) networks among others.

The disclosed anxiety models also retained features across a widespread set of networks including high representation in the DM network and sparser representation across executive networks (FPTC, COTC, Dorsal Attention (DA)), SAL network, and sensory networks. Though conventional research links anxiety to a set of networks including a threat circuit, the SAL, DM, and Attention networks, the models of the present disclosure indicate that the dysfunction is related to the DM, SAL, and Sensory/Somatomotor networks, the FPTC network, in addition to COTC and Visual Attention (VA) networks. The disclosed models indicate that the underlying elements of anxiety—difficulties regulating emotion in fearful situations, detecting and controlling conflict, increased attention to emotional stimuli—have relationships to this set of networks.

The disclosed depression and mood models predicted outcome variables that were not as narrowly focused on a single symptom. The Mood/Dep_Hopkins sub score contained depressed mood questions but also ones about guilt, suicide, loss of interest, and somatic concerns, while Mood_Bipolar contained questions about both depressed and manic moods, states which the brain may reflect differently. Both models relied on a broad set of networks beyond the negative affective circuit (ACC, mPFC, insula, and amygdala) previously proposed in the prior art. Both anterior and posterior nodes of the DM network were informative to the disclosed model as well as FPTC, COTC, Attention, SAL, and Sensory networks. Cognitive Control networks, Salience, and Attention, and Affective networks were involved in depressed mood while a central node, the subgenual cingulate, is involved in mood and connected within the DM network.

The clinical scale feature categories, as used in the present disclosure, include items from the TCI, Hopkins Symptom Checklist, and the Chapman scales across nearly all six symptom models. The TCI is a consistently predictive scale, as used in the present disclosure, as assessed by a number of questions contributed for all six models of mood, anhedonia, and anxiety. This scale measures temperaments such as harm avoidance and novelty seeking, which have previously been associated with depression and anxiety. In addition, the disclosed models picked out questions from TCI that pertained to social situations as predictive of the social anhedonia severity. Therefore, the consistent representation of TCI across the models suggests its potential utility when screening patients for multiple symptom domains.

The relative contributions of the different feature types as provided for by method 1600 above indicate that both scale items and fMRI connectivity are highly important to model predictability. While scale features tended to be more highly represented in the top 25% of features. Thus, their relative importance may be higher than fMRI features, though the multimodal models performed better than scales-only models, suggesting that both scale and fMRI components contain unique information. Such a comparison of different feature types in transdiagnostic or community-based psychiatric symptom severity biomarker studies is not common in the prior art. Therefore, the present disclosure provides a valuable step when multiple data types are available for creating predictive models; each data type has benefits and drawbacks in ease of collection, measurement stability, resources required for processing, etc. Different data types can be used according to these benefits and drawbacks.

Conventional research suggests that (1) sMRI regularly underperforms at Major Depressive Disorder (MDD) diagnostic classification in comparison to fMRI for MDD patients and (2) the lack of studies reporting sMRI abnormalities in SZ, BD, and ADHD reflects the lack of predictability or need for larger sample sizes in detecting effects in this modality.

The present disclosure further examines the categorical origins of the fMRI features and clinical scale features for the disclosed models. Specifically, anhedonia models found not only elements of a reward circuit but also multiple nodes in the DM, Salience (SAL), Cingulo-Opercular Task Control (COTC), Fronto-Parietal Task Control (FPTC), and Visual (VIS) networks among others. Connectivity changes tied to rewarding contexts in this wider set of networks have been observed in conventional research, while a meta-analysis of task-based reward processing in MDD demonstrated dysfunctional activation in a broad set of regions including frontal, striatal, cerebellar, visual, and inferior temporal cortex. As nodes within the DM network are activated both during self-referential processing and social and emotional processing, symptoms that decrease socially pleasurable experiences could have bases in this network. Moreover, coordination between several of these networks are necessary for healthy function, but patients with disruptions to the Salience network may have trouble switching between DM and executive control networks, which may underlie rumination or impaired reward processing. Indeed, subcortical nodes of the Salience network are located in mesocorticolimbic emotional and reward processing centers of the brain, so disruption of these functions may propagate to cortical salience regions and beyond.

The Mood_Bipolar outcome score contained questions about both depressed and manic moods, states which the brain may reflect differently. Conventional research found (1) increased amygdala-sensory connectivity and abnormal prefrontal-parietal connectivity during manic states, and extensive orbitofrontal to subcortical and cortical connectivity in depressed states and (2) the ratio of DM to sensorymotor network activity was greater in a depressed state of BD and less in manic states in BD. The results of the disclosed models provide that a wide set of regions and networks is linked to depressed and elevated mood; additionally, there may be some dissociation between the two with more DM in depressed mood and sensory involvement in elevated mood. The Mood_Bipolar model includes multiple nodes from both sets of RSNs as important features.

Regarding the MRI features that may be indexing neurobiological mechanisms, the disclosed transdiagnostic regression approach is agnostic to the question of same/different mechanisms underlying these symptoms. It is likely that multiple mechanisms exist for each of these symptoms, but the modeled symptom constructs are based on sum scores that likely cannot differentiate different mechanisms (like anticipatory v. consummatory anhedonia). In theory, differing mechanisms may even span diagnoses rather than differ between diagnoses. Regularized regression modeling identifies all predictive features from a sample, and thus multiple possible mechanistic features, features reported as important for each model might not be related to a single underlying mechanism; rather, the reported features may be related to multiple underlying mechanisms. Models that incorporate multiple mechanisms can be applicable to a wider population.

Experimental Method and Additional Details

An experimental methodology is disclosed further herein which provides additional examples of methodologies 1500 and 1600, as would be readily apparent to one skilled in the art. The experimental methodology includes experimental results which verify additional aspects of the disclosed systems and methods; the experimental results further verify additional benefits of the present disclosure as compared against conventional systems and methods.

Four groups of participants were included in the sample data, the participants drawn from adults aged 21-50 years: healthy controls (HC, n=130), individuals with schizophrenia (SZ, n=50), Bipolar Disorder (BD, n=49), or Attention Deficit and Hyperactivity Disorder (ADHD, n=43). This full set of participants is outlined below in Table 1.

TABLE 1

| Demographic information for full set of participants | | | | |
|---|---|---|---|---|
|  | HC | SCZ | BD | ADHD |
| No. of participants | 130 | 50 | 49 | 43 |
| Age |  |  |  |  |
| Mean age | 31.26 | 36.46 | 35.15 | 33.09 |
| SD age | 8.74 | 8.88 | 9.07 | 10.76 |
| Range age | 21-50 | 22-49 | 21-50 | 21-50 |
| Gender |  |  |  |  |
| No. of female participants | 62 | 12 | 21 | 22 |
| Percent female participants | 47.69% | 24.00% | 42.86% | 51.16% |
| Race |  |  |  |  |
| American Indian or Alaskan Native | 19.23% | 22.00% | 6.25% | 0% |
| Asian | 15.38% | 2.00% | 0% | 2.33% |
| Black/African American | 0.77% | 4.00% | 2.08% | 2.33% |
| White | 78.46% | 66.00% | 77.08% | 88.37% |
| More than one race | 0% | 2.00% | 14.58% | 6.98% |
| Education |  |  |  |  |
| No high school | 1.54% | 18.00% | 2.08% | 0% |
| High school | 12.31% | 44.00% | 29.17% | 23.26% |
| Some college | 20.77% | 18.00% | 25.00% | 30.23% |
| Associate's degree | 7.69% | 4.00% | 6.25% | 6.98% |
| Bachelor's degree | 50.00% | 10.00% | 29.17% | 32.56% |
| Graduate degree | 6.92% | 0% | 4.17% | 2.33% |
| Other | 0.77% | 4.00% | 4.17% | 4.65% |
| MRI Scanner |  |  |  |  |
| No. of participants on scanner 1 | 106 | 25 | 26 | 23 |
| No. of participants on scanner 2 | 24 | 25 | 23 | 20 |

Comorbid diagnoses were allowed and identified for 81% of patients. For the three patient groups, stable medications were permitted. Diagnoses were based on the Structured Clinical Interview for DSM-IV (SCID) and supplemented with the Adult ADHD Interview. After examining subjects for missing data and performing quality control on the data (as detailed herein), the subject pool was reduced. Referring momentarily to FIG. 13, current medication usage status, grouped by medication class, is identified for each group. Each bar represents the percent of a diagnostic group that was using a stable medication of that particular class. Some diagnostic groups did not have any subjects using medications from a particular class. No HC subjects were on psychiatric medications per enrollment criteria.

CNP Dataset

The CNP dataset (release 1.0.5), retrieved from the OpenNeuro platform, contains demographic, behavioral, clinical, and imaging data (no genetic data is included). Of the extensive behavioral testing that participants underwent, the present disclosure provides analysis from tests of participant self-reported symptoms and traits (clinician-administered instruments were only given to subsets of participants). The self-reported scales used in our analysis include the Chapman social anhedonia scale (denoted Chapsoc), Chapman physical anhedonia scale (Chapphy), Chapman perceptual aberrations scale (Chapper), Chapman hypomanic personality scale, Hopkins symptom checklist (Hopkins), Temperament and Character Inventory (TCI), adult ADHD self-report scale v1.1 screener (ASRS), Barratt Impulsiveness Scale (Barratt), Dickman functional and dysfunctional impulsivity scale (Dickman), multidimensional personality questionnaire—control subscale (MPQ), Eysenck's impulsiveness, venturesomeness, and empathy scale (Eysenck), scale for traits that increase risk for bipolar II disorder (Bipolar_ii), and Golden and Meehl's Seven MMPI items selected by taxonomic method (Golden).

MRI Data Acquisition

The MM data acquired according to the experiments of the present disclosure were provided on 3T Siemens Trio scanners. Exemplary sMRI data was T1-weighted and acquired using a magnetization-prepared rapid gradient-echo (MPRAGE) sequence with the following acquisition parameters: TR=1.9 s, TE=2.26 ms, FOV=250 mm, matrix=256×256, 176 1-mm thick slices oriented along the sagittal plane. The resting-state fMRI scan was a single run lasting 304 s. The scan was acquired using a T2*-weighted echoplanar imaging (EPI) sequence using the following parameters: 34 oblique slices, slice thickness=4 mm, TR=2 s, TE=30 ms, flip angle=90°, matrix size 64×64, FOV=192 mm. During the resting-state scan, subjects remained still and relaxed inside the scanner and kept their eyes open. No specific stimulus or task was presented to them.

Preprocessing Data into Features

Experiments conducted according to the present disclosure used responses to individual questions from the thirteen (13) self-report scales as input features for a total of five hundred seventy-eight (578) questions. One participant had incomplete clinical scale data and was not included in subsequent analyses. Outcome variables for modeling dysregulated mood, anhedonia, and anxiety were also selected from the clinical scales. Mood dysregulations included both depressed mood and mania.

Preprocessing of sMRI was performed using the recon-all processing pipeline from the FreeSurfer software package. The T1-weighted structural image from each participant was intensity-normalized and skull-stripped. The subcortical structures, white matter, and ventricles were segmented and labeled. The pial and white matter surfaces were then extracted and tessellated, and cortical parcellation was obtained on the surfaces according to a gyral-based anatomical atlas which partitions each hemisphere into thirty-four (34) regions. The structural features from bilateral aparc.stats and aseg.stats files were extracted via the aparcstats2table and asegstats2table functions in FreeSurfer, and this included cortical and subcortical regional volumes, cortical surface area, and cortical thickness estimates. Ten subjects had missing sMRI scans and were not included in subsequent analyses.

Preprocessing of rs-fMRI was performed using the AFNI software package. Preprocessing of each participant's echo planar image (EPI) data included: removal of the first three volumes (before the scanner reached equilibrium magnetization), de-spiking, registration of all volumes to the now first volume, spatial smoothing with a 6 mm full-width half-maximum Gaussian filter, and normalization of all EPI volumes by the mean signal to represent data as percent signal change. Anatomical data also underwent several steps: deobliquing of the T1 data, uniformization of the T1 to remove shading artifacts, skull-stripping of the T1, spatial alignment of the T1 and FreeSurfer-segmented and -parceled anatomy to the first volume of the EPI data, and resampling of the FreeSurfer anatomy to the resolution of the EPI data. Subsequently, the ANATICOR procedure was used for nuisance tissue regression. White matter and ventricle masks were created and used to extract the blood-oxygen-level-dependent (BOLD) signals (before spatially-smoothing the BOLD signal). A 25 mm-radius sphere at each voxel of the white matter mask was used to get averaged local white matter signal estimates while the average ventricle signal was calculated from the whole ventricle mask. Time series for the motion estimates, and the BOLD signals in the ventricles and white matter were detrended with a fourth-order polynomial. To clean the BOLD signal, the experimental methodology provided for regressing out the nuisance tissue regressors and the six motion estimate parameters. Cleaned data residuals were used for all subsequent analysis. Both the preprocessed T1 scan and the cleaned residuals of the EPI scan were warped to MNI space and resampled to 2 mm isotropic voxels. The time series of the cleaned residual data was extracted from each of two hundred sixty-four (264) ROIs as delineated by the Power atlas. At each ROI, the signals from the voxels within a 5 mm radius sphere were averaged. Pearson's correlations were then calculated between the averaged time series from all ROIs yielding 34,716 unique edges in the functional connectivity graph (upper triangle of the full correlation matrix). Ten additional subjects (beyond the ten with missing sMRI data) did not have fMRI scans and were thus excluded from subsequent analysis.

Quality control (QC) for MRI preprocessing was performed individually on the whole dataset by two authors (MM, YL) who had 85% and 89% agreement between them regarding rejection decisions for each participant's sMRI and rs-fMRI data, respectively. Specifically, participants were excluded if they had misregistration between fMRI and sMRI scans, >3 mm head motion in the fMRI scan (to correspond with edge length of a voxel in functional scan), headphone artifacts that overlapped with brain tissue in the sMRI scan, incorrect FreeSurfer-automated grey/white segmentation and anatomical parcellation in the sMRI scan, and aliasing or field of view artifacts in either scan. Discrepancies were resolved between the two authors in order to create a final rejection list of participants. The disclosed methodology used two hundred seventy (270) sMRI features from FreeSurfer-calculated cortical and subcortical regional volumes, cortical surface area, and cortical thickness estimates, and 34,716 AFNI-processed fMRI connectivity features calculated from pairwise Pearson's correlations between two hundred sixty-four (264) ROIs of the Power atlas. Subsets of these input features were used as predictor variables in subsequent modeling as explained below.

Output variables that were modeled included those which indexed depression, anxiety, anhedonia, or other negative symptoms. A mix of total scores, sub-scale sum or average scores, and individual question scores were predicted as each has their advantages. These scores include the twenty-eight (28)-question versions of the total HAMD score ('hamd'), the HAMD subscore for questions 1, 7, and 8 ('hamd178', indexes a melancholic-type of symptom), the HAMD item score for question 7 ('hamd7', indexes lack of interest or anhedonia), the Chapman Social Anhedonia total score ('chapsoc'), the Chapman Physical Anhedonia total score ('chapphy'), BPRS negative subscore ('bprs_negative', the average of negative symptom questions 13, 16, 17, and 18), BPRS depression-anxiety subscore ('bprs_depanx', the average of depression and anxiety symptom questions 2, 3, 4, and 5), Hopkins anxiety score ('hopkins_anxiety', the average of anxiety symptom questions 2, 17, 23, 33, 39, and 50), Hopkins depression score ('hopkins_depression', the average of depression symptom questions 5, 15, 19, 20, 22, 26, 29, 30, 31, 32, and 54), Bipolar ii mood score ('bipolarii_mood', the sum of mood questions 1-9), Bipolar ii anxiety score ('bipolar_anxiety', the sum of anxiety questions 24-31), SANS anhedonia factor score ('sans_factor_anhedonia', the average of anhedonia questions 17, 18, 19, and 20), SANS anhedonia global score ('sans_global_anhedonia', questions 21 which is the clinician's overall anhedonia assessment score), SANS avolition factor score ('sans_factor_avolition', the average of avolition items 12, 13, 14, and 15), SANS avolition global score ('sans_global_s_avolition', question 16 which is the clinician's overall avolition assessment score), SANS blunt affect factor score ('sans_factor_bluntaffecct', the average of affective flattening items 1, 2, 3, 4, 5, and 6), SANS blunt affect global score ('sans_global_bluntaffect', question 7 which is the clinician's overall blunt affect assessment score), SANS alogia factor score ('sans_factor_alogia', the average of alogia items 8, 9, and 10), SANS alogia global score ('sans_global_alogia', question 11 which is the clinician's overall alogia assessment score), SANS attention factor score ('sans_factor_attention', the average of attention items 22 and 23), and SANS attention global score ('sans_global_attention', question 24 which is the clinician's overall attention assessment score).

Sum scores are commonly accepted by the FDA regarding positive efficacy results, but using only sum scores may obfuscate brain-behavior relationships at more fine-grained levels of symptoms. Subjects with missing values ("n/a") for any input or output variables or who did not pass MRI QC were removed from the input set. As different input feature sets were used, different models had different sample sizes. The availability of clinical scores for particular clinical scales taken only by certain subsets of patients also affected the final sample size for each model. See the samples sizes resulting from these factors in Table 2.

TABLE 2

Sample Sizes Resulting from Select Factors

| Predicted Scores | Scales | sMRI | fMRI | Scales_sMRI | sMRI_fMRI | Scales_fMRI | Scales_sMRI_fMRI |
|---|---|---|---|---|---|---|---|
| Chapman Social Anhedonia | 271 | 206 | 147 | 205 | 117 | 146 | 116 |
| Chapman Physical Anhedonia | 271 | 206 | 147 | 205 | 117 | 146 | 116 |
| HAMD, total score | 141 | 108 | 82 | 107 | 63 | 81 | 62 |
| HAMD, q1, 7, 8 sum score | 140 | 108 | 82 | 107 | 63 | 81 | 62 |
| HAMD, q7 | 140 | 108 | 82 | 107 | 63 | 81 | 62 |
| BPRS, negative score | 141 | 108 | 82 | 107 | 63 | 81 | 62 |
| BPRS, depression-anxiety score | 141 | 108 | 82 | 107 | 63 | 81 | 62 |
| Hopkins, anxiety score | 271 | 206 | 147 | 205 | 117 | 146 | 116 |
| Hopkins, depression score | 271 | 206 | 147 | 205 | 117 | 146 | 116 |
| Bipolar II, depression score | 271 | 206 | 147 | 205 | 117 | 146 | 116 |
| Bipolar II, anxiety score | 271 | 206 | 147 | 205 | 117 | 146 | 116 |
| SANS, anhedonia factor | 99 | 75 | 54 | 74 | 40 | 53 | 39 |
| SANS, avolition factor score | 99 | 75 | 54 | 74 | 40 | 53 | 39 |
| SANS, blunt affect factor score | 99 | 75 | 54 | 74 | 40 | 53 | 39 |
| SANS, alogia factor score | 99 | 75 | 54 | 74 | 40 | 53 | 39 |
| SANS, attention factor score | 99 | 75 | 54 | 74 | 40 | 53 | 39 |
| SANS, anhedonia global score | 87 | 74 | 83 | 73 | 39 | 52 | 38 |
| SANS, avolition global score | 99 | 75 | 54 | 74 | 40 | 53 | 39 |
| SANS, blunt affect global score | 99 | 75 | 54 | 74 | 40 | 53 | 39 |
| SANS, alogia global score | 99 | 75 | 54 | 74 | 40 | 53 | 39 |
| SANS, attention global score | 99 | 75 | 54 | 74 | 40 | 53 | 39 |

Regression Modeling

All regression modeling was performed with a combination of Python language code and the Python language toolbox scikit-learn (http://scikit-learn.org/stable/index.html). The disclosed experiment modeled six different symptom severity scores across the clinical scales, two each for mood, anhedonia, and anxiety. All outcome measures were precalculated in the CNP dataset. For mood, the average of the Hopkins scale depression symptom questions was used (further referenced as Mood/Dep_Hopkins) and the sum of mood questions from the Bipolar_ii inventory (Mood_Bipolar). The two anhedonia variables were derived from total scores on the Chapman Social Anhedonia scale (Anhedonia_Chapsoc) and the Chapman Physical Anhedonia scale (Anhedonia_Chapphy). Anxiety was indexed from the sum of Bipolar_ii anxiety questions (Anxiety_Bipolar) and average of anxiety symptom questions (Anxiety_Hopkins).

The experimental methodology built one hundred twenty-six (126)—(6 outcome variables×7 predictor variable sets×3 model algorithms)—sets of models. For each of these sets of models, hyperparameters were tuned using 5-fold cross-validated grid-search on a training set of data (80% of data), and the model using the selected hyperparameters was tested on a separate evaluation set of data (20% held-out sample). This train/evaluation split was performed twenty-five (25) times for a version of nested cross-validation where the outer loop was repeated random sub-sampling validation. Critically, this nested cross-validation approach means that models are trained on a training set that is completely separate from an evaluation set used to generate evaluation metrics reported as final results. For each of the 126 sets of models, the experimental methodology took an importance-weighted, forward selection approach to regression modeling, involving three main steps: first, an initial rank-ordering step for ordering features by importance; second, a forward-selection search step for building a series of models utilizing growing subsets of ordered features (i.e., the best features) selected from the first step; and third, an evaluation step to choose the best model and subset of features according to a prespecified criterion to find the optimal model.

The twenty-five (25) iterations of training/evaluation set splits for modeling and validation as explained above allowed generation of descriptive statistics for each feature subset to calculate median and standard deviation metric scores. The metrics chosen for the final step of evaluation were mean squared error (MSE) and $r^2$ calculated on the held-out evaluation sets. The median $r^2$ and standard deviation of $r^2$ were found for each subset. And the "best model" overall was selected by finding the maximum median $r^2$ value over all feature subsets and selecting the model that corresponded to that max median $r^2$ value (FIGS. 1A-1B). To find which input feature set and which model type led to the best biomarkers, subsequent comparisons were also made based on the $r^2$ of the best models.

Thus, further examination of features focused on this set of models. An initial comparison between models that used the full feature sets (up to 35,564 features) and those that used the optimal set of truncated features (ordered subsets of the full feature sets identified through the forward modeling approach) demonstrated vastly different performances between the modeling approaches. The modeling results for Elastic Net using the full feature sets on average explained 22% of the variance while truncated sets explained an average of 78% for the clinical scales data, sMRI data and fMRI data input models (metrics for full features sets are presented in below in Table 3).

TABLE 3

Comparison of all Elastic Net Models using Full Feature Sets.
Full Features Sets

| Outcome Variables | Metric | Scales | sMRI | fMRI | Scales_ sMRI | sMRI_ fMRI | Scales_ fMRI | Scales_ sMRI_ fMRI |
|---|---|---|---|---|---|---|---|---|
| Mood/Dep_ Hopkins | median MSE | 0.196 | 0.310 | 0.276 | 0.208 | 0.349 | 0.224 | 0.103 |
|  | median $r^2$ | 0.373 | 0.019 | −0.595 | 0.229 | −0.157 | 0.290 | 0.238 |
| Mood_ Bipolar | median MSE | 2.172 | 11.538 | 7.683 | 1.809 | 6.379 | 2.426 | 2.099 |
|  | median $r^2$ | 0.670 | −0.282 | −0.140 | 0.676 | −0.255 | 0.579 | 0.658 |
| Anhedonia_ Chapphy | median MSE | 48.835 | 69.992 | 64.141 | 36.425 | 65.951 | 25.679 | 59.355 |
|  | median $r^2$ | 0.249 | −1.046 | −0.156 | 0.052 | −0.537 | 0.435 | 0.247 |
| Anhedonia_ Chapsoc | median MSE | 23.597 | 118.983 | 60.536 | 21.494 | 39.454 | 25.938 | 25.641 |
|  | median $r^2$ | 0.539 | −0.941 | −0.255 | 0.597 | −0.443 | 0.565 | 0.293 |
| Anxiety_ Hopkins | median MSE | 0.105 | 0.328 | 0.343 | 0.130 | 0.261 | 0.253 | 0.213 |
|  | median $r^2$ | 0.324 | −0.028 | −0.110 | 0.322 | 0.031 | −0.097 | −0.510 |
| Anxiety_ Bipolar | median MSE | 1.831 | 3.432 | 3.634 | 1.815 | 2.762 | 1.200 | 1.108 |
|  | median $r^2$ | 0.183 | −0.115 | 0.003 | 0.624 | −0.072 | 0.473 | 0.387 |

For the six models using Elastic Net with the clinical scales data, sMRI data, and fMRI data input feature set, model performance was evaluated on the held-out evaluation set with measured v. predicted plots (FIGS. 2A-2C) and $r^2$ values across models for different outcome variables (see Table 4 below, last column). All six models were highly predictive with the variance explained ranging from 65-90% and number of non-zero features p ranging from 28-106 (Mood/Dep_Hopkins $r^2=0.72$, p=28; Mood_Bipolar $r^2=0.90$, p=93; Anhedonia_Chapphy $r^2=0.65$, p=32; Anhedonia_Chapsoc $r^2=0.80$, p=106; Anxiety_Hopkins $r^2=0.75$, p=47; Anxiety_Bipolar $r^2=0.85$ p=31).

TABLE 4

Comparison of all Elastic Net Models using Truncated Feature Sets Returned by Forward Selection Approach
Truncated Features Sets

| Outcome Variables | Metric | Feature Set | | | | | | |
|---|---|---|---|---|---|---|---|---|
| | | Scales | sMRI | fMRI | Scales_ sMRI | sMRI_ fMRI | Scales_ fMRI | Scales_ sMRI_ fMRI |
| Mood/DEP_ Hopkins | median MSE | 0.148 | 0.299 | 0.159 | 0.106 | 0.138 | 0.110 | 0.076 |
| | median $r^2$ | 0.530 | 0.019 | 0.450 | 0.677 | 0.415 | 0.610 | 0.721 |
| | p | 50 | 3 | 29 | 102 | 16 | 26 | 28 |
| Mood_Bipolar | median MSE | 1.183 | 6.408 | 2.530 | 1.021 | 1.867 | 0.814 | 0.614 |
| | median $r^2$ | 0.836 | 0.123 | 0.625 | 0.864 | 0.719 | 0.874 | 0.904 |
| | p | 112 | 22 | 255 | 114 | 241 | 236 | 93 |
| Anhedonia_ Chapphy | median MSE | 19.670 | 42.835 | 21.406 | 15.178 | 14.419 | 9.648 | 15.814 |
| | median $r^2$ | 0.642 | 0.158 | 0.656 | 0.690 | 0.740 | 0.841 | 0.652 |
| | p | 240 | 61 | 358 | 123 | 211 | 211 | 32 |
| Anhedonia_ Chapsoc | median MSE | 12.510 | 43.893 | 13.246 | 10.847 | 14.682 | 8.627 | 9.886 |
| | median $r^2$ | 0.782 | 0.065 | 0.732 | 0.796 | 0.677 | 0.829 | 0.804 |
| | p | 126 | 32 | 345 | 63 | 559 | 31 | 106 |
| Anxiety_ Hopkins | median MSE | 0.134 | 0.260 | 0.110 | 0.145 | 0.098 | 0.095 | 0.077 |
| | median $r^2$ | 0.525 | 0.042 | 0.653 | 0.471 | 0.650 | 0.704 | 0.751 |
| | p | 54 | 6 | 85 | 49 | 29 | 127 | 47 |
| Anxiety_ Bipolar | median MSE | 1.252 | 2.865 | 0.988 | 0.798 | 0.703 | 0.589 | 0.535 |
| | median $r^2$ | 0.616 | 0.121 | 0.644 | 0.735 | 0.789 | 0.825 | 0.847 |
| | p | 62 | 16 | 153 | 58 | 161 | 32 | 31 |

Next, the proportions of features derived from clinical scale data, fMRI data, and sMRI data feature sets were compared for the best model for each outcome variable both among the whole feature set and the top 25% of features (FIGS. 3A-3B). The best models for Mood/Dep_Hopkins, Anhedonia_Chapphy, and Anxiety_Bipolar had a roughly equal number of clinical scale and fMRI features while Anxiety_Hopkins, Anhedonia_Chapsoc, and Mood_Bipolar models had a bias towards fMRI features (FIG. 3A). FIG. 3B shows, however, that for many outcome variables there was a disproportionate number of scale features in the top features. Notably, there was a paucity of sMRI features in both these models as only Anhedonia_Chapphy had any sMRI features selected by the models.

The disclosed experimental methodology modeled six different symptom severity scores across the clinical scales, two each for mood, anhedonia, and anxiety. First, the methodology provides for predicting a mix of total scores and sub-scale sum or average scores from scales that were given to all three patient groups and HCs to retain the largest number of participants possible in the models. Each of these scores was already calculated and included in the CNP dataset. For mood, the average of depression symptom questions 5, 15, 19, 20, 22, 26, 29, 30, 31, 32, and 54 from the Hopkins inventory (precalculated "Hopkins_depression" score, further referenced as Mood/Dep_Hopkins in this study) and the sum of mood questions 1-9 from the Bipolar_ii inventory (precalculated "Bipolar_mood" score, further referenced as Mood_Bipolar in this study) was used. The two anhedonia variables were derived from total scores on the Chapman Social Anhedonia scale (precalculated "Chapsoc" score, further referenced as Anhedonia_Chapsoc in this study) and the Chapman Physical Anhedonia scale (precalculated "Chapphy" score, further referenced as Anhedonia_Chapphy in this study). And anxiety was indexed from the sum of Bipolar_ii anxiety questions 24-31 (precalculated "Bipolar_anxiety" score, further referenced as Anxiety_Bipolar in this study) and average of anxiety symptom questions 2, 17, 23, 33, 39, and 50 from the Hopkins anxiety score (precalculated "Hopkins_anxiety" score, further referenced as Anxiety_Hopkins in this study).

For each of the six models (Mood/Dep_Hopkins, Mood_Bipolar, Anhedonia_Chapsoc, Anhedonia_Chapphy, Anxiety_Bipolar, Anxiety_Hopkins), seven combinations of feature types were used as inputs to be able to evaluate the performance of single and multimodal feature sets. These included (1) clinical scales data only, (2) sMRI data only, (3) fMRI data only, (4) clinical scales data and sMRI data, (5) clinical scales data and fMRI data, (6) sMRI data and fMRI data, and (7) clinical scales data, sMRI data, and fMRI data. As different input feature sets were used, different models had different sample sizes. The samples sizes resulting from this factor were n=271 for the clinical scales only models, n=206 for sMRI only models, n=147 for fMRI only models, n=205 for clinical scales data and sMRI data models, n=117 for sMRI data and fMRI models, n=146 for clinical scales data and fMRI data models, and n=116 for clinical scales data, sMRI data, and fMRI data models (see Table 5 below. As input features varied in their mean values and regularized models require normally distributed data, each input feature was scaled separately to have zero mean and unit variance. This approach of using clinical scales, sMRI, and fMRI features as inputs reflect multiple goals of the disclosed methodology: (1) finding the feature set that maximizes predictability, and (2) exploring ways to reduce the dimensionality of feature sets. For example, in the case of using clinical self-report measures to predict clinical scale measures, reducing the dimensionality is useful in removing redundancy and finding a compact, optimized set of questions which could reduce time and/or cost of administration and which could potentially better map onto neural circuitry.

TABLE 5

Sample size for each model

| Outcome Variables | Number of Subjects | | | | | | |
|---|---|---|---|---|---|---|---|
| | Scales | sMRI | fMRI | Scales_ sMRI | sMRI_ fMRI | Scales_ fMRI | Scales_ sMRI_ fMRI |
| Mood/Dep_ Hopkins | 271 | 206 | 147 | 205 | 117 | 146 | 116 |

TABLE 5-continued

Sample size for each model

Number of Subjects

| Outcome Variables | Scales | sMRI | fMRI | Scales_ sMRI | sMRI_ fMRI | Scales_ fMRI | Scales_ sMRI_ fMRI |
|---|---|---|---|---|---|---|---|
| Mood_Bipolar | 271 | 206 | 147 | 205 | 117 | 146 | 116 |
| Anhedonia_Chapphy | 271 | 206 | 147 | 205 | 117 | 146 | 116 |
| Anhedonia_Chapsoc | 271 | 206 | 147 | 205 | 117 | 146 | 116 |
| Anxiety_Hopkins | 271 | 206 | 147 | 205 | 117 | 146 | 116 |
| Anxiety_Bipolar | 271 | 206 | 147 | 205 | 117 | 146 | 116 |

In order to probe performance with a variety of modeling algorithms, for each scale output and feature set input, two regularized general linear model regression algorithms, LASSO and Elastic Net, and one non-linear regression model algorithm, Random Forest, were used for the modeling. These methods improved prediction accuracy and interpretability over regular regression methods using ordinary least squares. LASSO uses regularization by imposing an L1-penalty parameter to force some coefficients to zero; this step introduces model parsimony that benefits interpretability and predictive performance while guarding against overfitting. If predictor variables are correlated, however, the LASSO approach arbitrarily forces only a subset of the variables to zero, which makes interpretation of specific features more difficult. The Elastic Net algorithm uses both L1- and L2-penalty parameters to better retain groups of correlated predictor variables; this improves interpretability as highly predictive features will not randomly be set to zero (thereby diminishing their importance to the model). It is also better suited in cases when the number of predictor variables is much greater than the number of samples ($p \gg n$). The non-linear regression algorithm Random Forest was also chosen for comparison purposes.

In the one hundred twenty-six (126) sets of models built according to the present disclosure, hyperparameters were tuned using 5-fold cross-validated grid-search on a training set of data (80% of data), and selected hyperparameters were used on a separate evaluation set of data (20% held-out sample). This train/evaluation split was performed twenty-five times (25x) for a version of nested cross-validation (inner loop is 5-fold for hyperparameter optimization and model fitting, and outer loop is repeated random sub-sampling validation twenty-five times (25x) for model evaluation). This nested cross-validation approach means that models are trained on a training set that is completely separate from an evaluation set used to generate evaluation metrics reported as final results. The approaches of nested cross-validation and of splitting data between training and evaluation data is one way to minimize overfitting in addition with permutation testing (which can also be performed). The hyperparameter range for LASSO was alpha equal to 0.01, 0.03, and 0.1 (three samples through the log space between 0.01 and 0.1) which is the coefficient of the L1 term. Hyperparameter ranges for Elastic Net were alpha equal to 0.01, 0.03, and 0.1, and l1 ratio equal to 0.1, 0.5, and 0.9 which is the mixing parameter used to calculate both L1 and L2 terms. Hyperparameter ranges for Random Forest included the number of estimators equal to 10 or 100 and the minimum samples at a leaf equal to 1, 5, and 10. The best hyperparameters were chosen from the model that maximized an interim $r^2$ score (coefficient of determination) across the 5-fold cross-validation procedure in the training set and applied to the model of the never-seen evaluation set.

For each of the one hundred twenty-six (126) sets of models, an importance-weighted, forward selection approach to regression modeling (a variation of forward-stepwise selection) was applied as a data-driven way to identify the optimal feature subset to include in regression modeling. Finding an optimal subset helps in high-dimensional cases where the number of features is greater than the number of samples to avoid overfitting of the models. It also reduces nuisances from uninformative input variables without requiring the modeler to decide a priori whether a variable is signal or noise. This approach involves three main steps: (1) an initial rank-ordering step for ordering features by importance; (2) a forward-selection search step for building a series of models utilizing growing subsets of ordered features (i.e., the best features) selected from the first step; and (3) an evaluation step to choose the best model and subset of features according to a prespecified criterion to find the optimal model. This approach thus integrates feature selection into modeling using a multivariate embedded method that can take variable interactions into account to potentially construct more accurate models. Within each step, each new model utilized the training/evaluation set split and grid-search procedure to optimize hyperparameters as explained above. First, the feature rank-ordering step uses the full feature set (either clinical scales data only, sMRI data only, etc.) as the input to the model algorithms which returns not only predicted values for the evaluation dataset but also the importance of each feature for the resulting model. Feature importance was assessed from the regression coefficients of LASSO and Elastic Net models with ordering (most important to least important) based on the absolute value of the coefficient. Ordering by absolute value reflects that features with the largest magnitude influence the symptom severity scores the most. Feature ordering for the Random Forest algorithm (typical regression coefficients are not available) was done using the "gini importance" or mean decrease in impurity as implemented in the scikit-learn library.

Second, the forward-selection search step systematically searches through subsets of the rank-ordered features (truncated feature sets) for the subset that leads to the best model. Since having more features than samples ($p \gg n$) both increases the risk of overfitting and decreases the performance due to uninformative features adding nuisances, this data-driven way of searching the ordered feature space for an optimal subset of features was used. A series of regressions on subsets of the ordered features was run with subsets chosen in powers of two (i.e., inputting the top feature only, the top two features only, the top four features only, etc.) up to two hundred fifteen (215) features. The outer loop of nested cross-validation (the twenty-five (25) iterations of training/evaluation set splits for modeling and validation as explained above) also allowed generation of descriptive statistics for each feature subset to get median and standard deviation metric scores. The metrics chosen for the final step of evaluation were mean squared error (MSE) and $r^2$ calculated on the held-out evaluation sets. The median $r^2$ and standard deviation of $r^2$ were found for each subset. And the "best model" overall was selected by finding the maximum median $r^2$ value over all feature subsets and selecting the model that corresponded to that max median $r^2$ value (FIGS.

1A-1B). All subsequent follow-up is on the one hundred twenty-six (126) best models for each combination of input/ model type/output.

To find which input feature set (clinical scales data only, sMRI data only, fMRI data only, clinical scales data and sMRI data, clinical scales data and fMRI data, sMRI data and fMRI data, and clinical scales data, sMRI, and fMRI) and which model type (LASSO, Elastic Net, Random Forest) led to the best biomarkers, subsequent comparisons were also made based on the $r^2$ of the best models. The $r^2$ is a standardized measurement of explained variance (with a maximum value of 1 but an unbounded minimum) while the MSE values are not standardized across the different models making it less appropriate to use MSE for comparison.

Several control scenarios were implemented to test alternative hypotheses that modeling may have been impacted by overfitting or variables of no interest. Model performance for the best models (chosen by the methods above) was compared with (1) models with permuted outcome variables (to test for overfitting) and (2) models that included variables of no interest in addition to the features of interest. In the first case, the null hypothesis is that the features and severity scores are independent; however, an overfit model could misidentify dependence. But if the high performance of the disclosed models is due to identification of real structure in the data rather than overfitting, the best models will perform significantly better than models built from the permuted data and the null hypothesis can be rejected. After the original ordering of features and selection of the 2n subset that led to the best model, severity scores were permuted across participants for a given outcome variable one hundred (100) times, and one hundred (100) models were built based on the permuted scores.

Predictability (assessed with $r^2$) was calculated from these one hundred (100)-permuted models which allowed generation of an empirically-derived distribution of $r^2$ values for calculating a test statistic (p-value) compared to the median $r^2$ of the chosen best model. In the second control case, models built with predictor variables of no interest allowed assessment of the predictability of these variables in relation to predictors of interest (scales data, sMRI data, fMRI data) to see if possible confounding variables drive the results. Variables of no interest included age; gender; years of schooling; in-scanner mean framewise displacement (FD) which was calculated as an L2 norm; the six in-scanner motion measures for x, y, z directions and pitch, roll, yaw; sharp head motion (output of AFNI's @1dDiffMag); number of frames that would have been censored at a threshold of FD>0.5 mm; the current use of medication categorized by medication class; and scanner number (since two scanners were used). Six sets of models were generated for the six outcome variables also using the importance-weighted forward-selection approach. The $r^2$ score distribution from the best of the nuisance models (p that optimized median $r^2$) was compared to the best models without nuisance variables included with the non-parametric Wilcoxon rank-sum tests to assess if nuisance variables change the predictive ability of the models.

Feature Stability

Feature stability (a measure of the consistency of feature weightings) was calculated using a correlation approach for the best models. The Pearson correlation coefficient between predictor variable coefficients (i.e., the importance measurements) retains more information over feature rankings or include/exclude subsets. From the 25 subsamplings of subjects into training and evaluation sets for each subset of features (p=1, 2, 4, 8, . . . , 32768 during the forward-selection search step), feature stability was calculated across these twenty-five (25) iterations for both the 32768 set of features (as it is nearly the full set of 35564 features) and the best models (the ones with the optimal p features as found from the best median $r^2$). Thus, given the vector of predictor coefficients for each of the twenty-five (25) model iterations, the pairwise correlations can be calculated between the twenty-five (25) coefficient vectors (25*(25−1)/2=300 combinations) which gives three hundred (300) pairwise correlations for each feature subset. The mean of these three hundred (300) correlation coefficients can be taken for each feature subset to find these correlation coefficient means.

Figure 9:
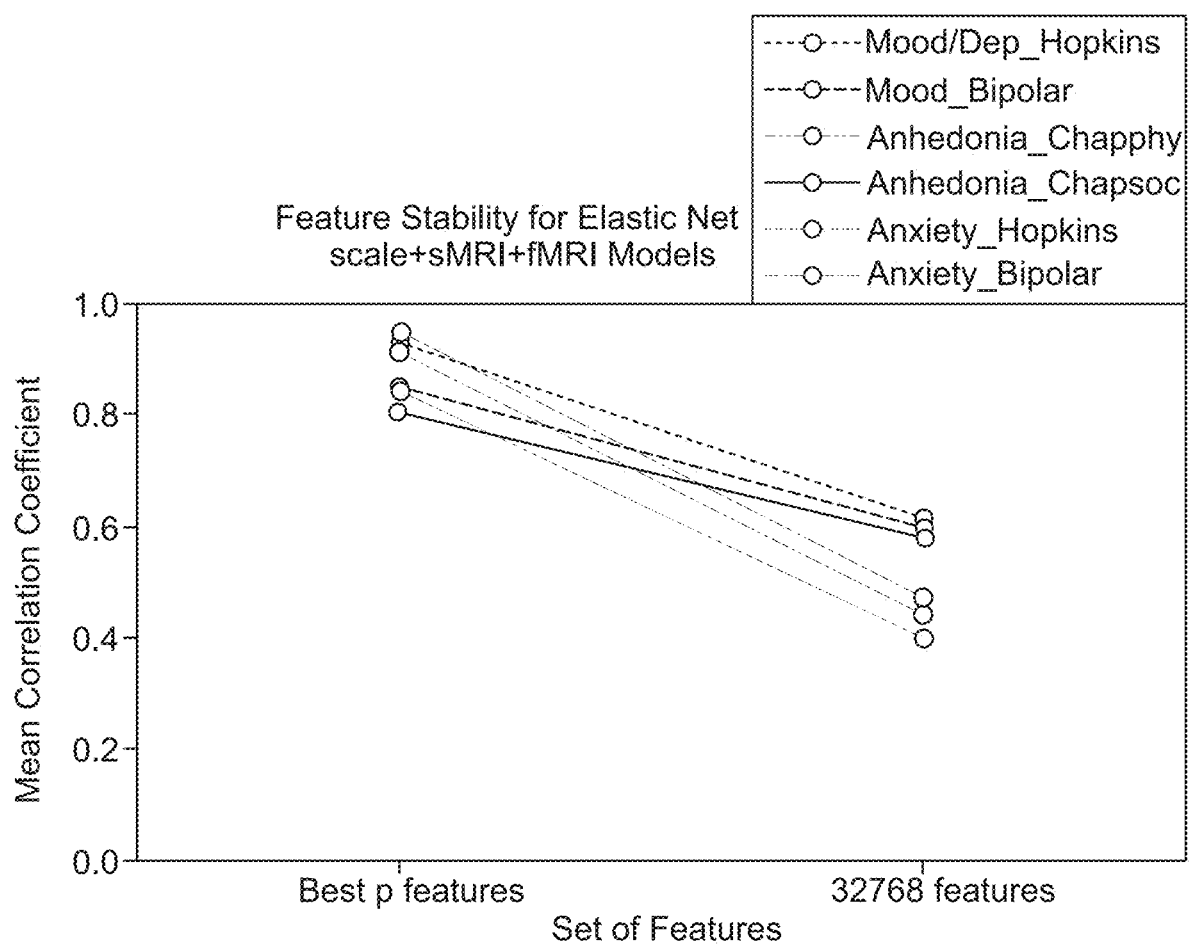
FIG. 9 illustrates a feature stability for the Elastic Net, having scales data, sMRI data, and fMRI data as input, according to some implementations of the present disclosure.

FIG. 9 shows the feature stability for the Elastic Net scales+sMRI+fMRI models. For the set of 32768 features, the correlation coefficient means were in a moderate range of 0.4 to 0.61 for Anxiety_Hopkins and Mood/Dep_Hopkins, respectively (shown in FIG. 9). In contrast, the feature stability of the models with optimal p features (as found from the best median $r^2$) range from 0.8 to 0.93 for Anhedonia_Chapsoc and Mood/Dep_Hopkins, respectively. So feature stability is moderate when using the nearly full set of features but improves when using an optimal subset selected with the forward modeling approach.

Clinical Features Associated with Symptom Severity

The disclosed methodology further examined groupings of the scale-based features sorted by the proportion of the scales from which they are derived. For each model, the scale features for the best model were proportionately selected from the scales shown in FIGS. 4A-4C. The TCI scale, in particular, was highly represented compared to the other scales in all six models (note that Hopkins, Bipolar, Chapphy, and Chapsoc items were not be included in all models). TCI contained a number of questions on temperament and character traits that could be related to a variety of symptoms, and the disclosed results suggested that it contained questions that are predictive of mood, anhedonia, and anxiety (shown in Table 6 below). Regression coefficients (ordered by magnitude) are either positive or negative, indicating that a "True" answer for the respective question increased or decreased the outcome variable score, respectively.

TABLE 6

Predictive Temperament and Character Inventory (TCI) questions for models of mood, anhedonia, and anxiety.

| Outcome Variable | Regression Coefficient | CNP Question Label | True/False Question |
| --- | --- | --- | --- |
| Mood/Dep_Hopkins | 0.06 | tci149t | I often stop what I am doing because I get worried, even when my friends tell me everything will go well. |

TABLE 6-continued

Predictive Temperament and Character Inventory (TCI) questions for models of mood, anhedonia, and anxiety.

| Outcome Variable | Regression Coefficient | CNP Question Label | True/False Question |
|---|---|---|---|
| | −0.05 | tci76p | I am more hard-working than most people. |
| | 0.04 | tci92t | I need much extra rest, support, or reassurance to recover from minor illnesses or stress. |
| | 0.02 | tci22t | I have less energy and get tired more quickly than most people. |
| | −0.01 | tci210t | People find it easy to come to me for help, sympathy, and warm understanding |
| Mood_Bipolar | 0.17 | tci140p | I often give up on a job if it takes much longer than I thought it would. |
| | 0.07 | tci12t | I often feel tense and worried in unfamiliar situations, even when others feel there is little to worry about. |
| | 0.06 | tci81t | Usually I am more worried than most people that something might go wrong in the future. |
| | 0.05 | tci217t | I usually feel tense and worried when I have to do something new and unfamiliar. |
| | 0.04 | tci53t | I lose my temper more quickly than most people. |
| Anhedonia_Chapphy | 0.77 | tci217t | I usually feel tense and worried when I have to do something new and unfamiliar. |
| | −0.52 | tci5p | I like a challenge better than easy jobs. |
| | 0.52 | tci156t | I don't go out of my way to please other people. |
| | 0.47 | tci120t | I find sad songs and movies pretty boring. |
| | 0.25 | tci83t | I feel it is more important to be sympathetic and understanding of other people than to be practical and tough-minded. |
| Anhedonia_Chapsoc | −1.19 | tci117t | I would like to have warm and close friends with me most of the time. |
| | 1.18 | tci231t | I usually stay away from social situations where I would have to meet strangers, even if I am assured that they will be friendly. |
| | −0.79 | tci21t | I like to discuss my experiences and feelings openly with friends instead of keeping them to myself |
| | 0.57 | tci44t | It wouldn't bother me to be alone all the time. |
| | 0.55 | tci46t | I don't care very much whether other people like me or the way I do things. |
| | −0.48 | tci210t | People find it easy to come to me for help, sympathy, and warm understanding |
| | 0.37 | tci201t | Even when I am with friends, I prefer not to \"open up\" very much. |
| | 0.34 | tci180t | I usually like to stay cool and detached from other people. |
| | 0.14 | tci70t | I like to stay at home better than to travel or explore new places. |
| Anxiety_Hopkins | 0.05 | tci141t | Even when most people feel it is not important, I often insist on things being done in a strict and orderly way. |
| | 0.05 | tci27t | I often avoid meeting strangers because I lack confidence with people I do not know. |
| | 0.04 | tci180t | I usually like to stay cool and detached from other people. |
| Anxiety_Bipolar | −0.25 | tci157t | I am not shy with strangers at all. |
| | 0.25 | tci54t | When I have to meet a group of strangers, I am more shy than most people. |
| | 0.23 | tci81t | Usually I am more worried than most people that something might go wrong in the future. |
| | 0.16 | tci129t | I often feel tense and worried in unfamiliar situations, even when others feel there is no danger at all. |
| | −0.14 | tci3t | I am often moved deeply by a fine speech or poetry. |
| | 0.10 | tci211t | I am slower than most people to get excited about new ideas and activities. |

TCI was a scale with important predictive features for all six models. It contained a number of questions on temperament and character traits that could be related to a variety of symptoms, and the results suggested that it contained questions that are predictive of mood, anhedonia, and anxiety, as shown above in Table 5. For example, 43% of the questions predictive of Anxiety_Bipolar were from TCI, with the most predictive question being, "I am not shy with strangers at all." Positive responses to this question predicted a lower Anxiety_Bipolar score since the regression coefficient was negative in this model. Though not uniformly so, some of the other questions also assessed shyness or worry. The Anhedonia_Chapsoc model also had a very high percentage of TCI questions, with the most predictive question being, "I would like to have warm and close friends with me most of the time." Here positive responses indicated decreased social anhedonia severity as the regression coefficient was also negative. While not all questions in the TCI pertain to people and social situations, all but one of the remaining questions that were predictive of the Anhedonia_Chapsoc score did include mention of these situations. The predictive questions for the Anhedonia_Chappy, Mood/Dep_Hopkins, Mood_Bipolar, and Anxiety_Hopkins scores were more mixed overall, though. Additionally, FIGS. 4A-4C show that Chaphyp questions were also predictive in all models (but only contributed 1-2 items in five of the six scales). The most numerous questions (6/31) from Chaphyp were for Mood_Bipolar which may be expected as the Chapman hypomanic scale, and the Mood_Bipolar subscore of this scale both included an assessment of mania (as opposed to the Mood/Dep_Hopkins score which is more related to depressed mood and depressive symptoms).

Neurobiological Characteristics of Dysregulated Mood, Anhedonia, and Anxiety

The fMRI connectivity features were composed of the strengths of network edges (connections between nodes) but can also be grouped by suggested intrinsic resting-state networks from the Power atlas. As the number of fMRI connectivity features selected by the models were a small subset of all possible fMRI connectivity features, full connectivity matrices are quite sparse (the full connectivity matrices are shown in FIGS. 10A-10C). Therefore, the number of edges within and between each intrinsic resting-state network (RSN) is shown in the connectivity matrices of FIGS. 5A-5F for each outcome variable. The predictive fMRI connectivity features appeared mostly distributed across multiple networks rather than selective to a few particular networks (FIGS. 5A-5F). Connectivity features implicate nodes in ten RSNs for Mood/Dep_Hopkins, 12 RSNs for Mood_Bipolar, 10 RSNs for Anhedonia_Chappy, 12 RSNs for Anhedonia_Chapsoc, 13 RSNs for Anxiety_Hopkins, and 10 RSNs for Anxiety_Bipolar models (out of fourteen (14) RSNs from this atlas). While Anhedonia_Chapsoc connectivity measures were also distributed, there was a higher concentration of connectivity features between the Default Mode (DM) network and other networks. In particular, the predictive edges between the DM and other networks mostly originate from the anterior cingulate and/or the medial orbitofrontal lobe. The Anhedonia_Chapsoc model also contained nodes in the top five features that were located within a reward circuit including the putamen and orbitofrontal cortex (OFC). Edges either within the DM network or between the DM and other networks consistently were the most numerous features relative to all other within- and between-network features across all models. All the features in each model, including sMRI, are available upon request from the authors.

Control models, including nuisance variables, found no predictive advantage of motion, age, gender, years of schooling, scanner number, or medication usage with the exception of SNRI antidepressants on Anhedonia_Chappy models.

Controls and Additional Models

To evaluate whether the disclosed models are influenced by confounding demographic or other variables, for each of the six outcome variables, six Elastic Net models were built with the Scales+sMRI+fMRI+nuisance features; the distribution of 25 $r^2$ measures was selected for the best nuisance models (p that optimized $r^2$) to compare with the $r^2$ measures of the best Scales+sMRI+fMRI non-nuisance models. Two comparisons returned no difference (Mood/Dep_Hopkins: Scales+sMRI+fMRI median $r^2$=0.72, Scales+sMRI+fMRI+nuisance median $r^2$=0.69, Wilcoxon Rank Sum U statistic=296, p=0.38; Mood_Bipolar: Scales+sMRI+fMRI median $r^2$=0.90, Scales+sMRI+fMRI+nuisance median $r^2$=0.90, U statistic=305, p=0.45). Two comparisons show significantly improved performance of the Scales+sMRI+fMRI models (Anxiety_Bipolar: Scales+sMRI+fMRI median $r^2$=0.85, Scales+sMRI+fMRI+nuisance median $r^2$=0.76, U statistic=135, p=0.0003; Anxiety_Hopkins: Scales+sMRI+fMRI median $r^2$=0.75, Scales+sMRI+fMRI+nuisance median $r^2$=0.59, U statistic=128, p=0.0002). And two comparisons show significantly improved performance of the Scales+sMRI+fMRI+nuisance models (Anhedonia_Chapsoc: Scales+sMRI+fMRI median $r^2$=0.80, Scales+sMRI+fMRI+nuisance median $r^2$=0.83, U statistic=221, p=0.038; Anhedonia_Chappy: Scales+sMRI+fMRI median $r^2$=0.65, Scales+sMRI+fMRI+nuisance median $r^2$=0.83, U statistic=94, p<0.0001). Critically, though Scales+sMRI+fMRI+nuisance models for Anhedonia_Chapsoc and Anhedonia_Chappy outcomes performed better, none of the nuisance variables were actually selected in models (they all had coefficients equal to zero) except for "Antidepressant-SNRI" in the Anhedonia_Chappy model (it was ranked 22 out of 207 non-zero features). Thus, current usage of SNRI antidepressants may affect physical anhedonia severity, but none of the other measured confounding variables affect the disclosed models.

Additionally, another set of Elastic Net models with the Scales+sMRI+fMRI feature set but with scrambled severity scores (a permutation testing approach) was built and used to test for overfitting, but no evidence of overfitting was found using this approach as demonstrated by the empirical null distributions (shown in FIGS. 11A-11C). For all six models, the median $r^2$ of the best models was statistically significant (p<0.01).

Methodology Using Resting-State fMRI Data

Uncovering the biological basis of patient heterogeneity is a key to creating clinically relevant biomarkers. Non-invasive imaging enables the visualization of the brain-to-symptom links underlying neurobehavioral disorders. Conventional technology is often too narrowly applied by only examining one aspect of biology (e.g., anatomical or functional MM measures) or a single diagnostic group. Since symptoms such as depression span multiple neurobehavioral disorders, a more robust symptom biomarker can be better captured by examining transdiagnostic patient cohorts and utilizing multiple neuroimaging modalities.

Therefore, embodiments of the present disclosure provide a transdiagnostic multimodal MRI model that successfully identified biomarkers that can reliably predict clinician-rated depression severity across multiple neurobehavioral disorders. This model can use the Consortium for Neuropsychiatric Phenomics dataset, which includes resting-state functional MRI (rs-fMRI) and structural-MM (sMRI) imaging measures from patients with schizophrenia, bipolar disorder, and attention deficit and hyperactivity disorder (n=142 total). Input features included preprocessed sMRI volume, surface, and thickness measures (270 features) and preprocessed rs-fMRI connectivity measures (34,716 features). The model provides an outcome measure of depression in the clinician-rated 28-item total score from the Hamilton Rating Scale for Depression (HAMD). The disclosed model also used an importance-ranked forward selection procedure with Elastic Net regression and cross-validation for an efficient, data-driven feature selection approach to identify the most predictive features from these high-dimensional data. This data-driven approach yielded a highly predictive transdiagnostic model that explained 61% of variance of the HAMD total score. Moreover, the feature selection step of this machine learning procedure returned a subset of features that were predictive and highly interpretable. Of the rs-fMRI connectivity features, the Default Mode Network was the primary source, while other predictive features were widely distributed across various resting-state networks including the Fronto-parietal Task Control, Salience, Somatosensory/motor, Subcortical, Attention, and Sensory networks. Structural features did not contribute much to the predictive strength of this model, representing only about 1% of features found to be predictive.

Altogether, the disclosed model provides an algorithm to predict depression across multiple neurobehavioral disorders. The features important to this algorithm suggest that functional connectivity, rather than anatomy, provides a "depressive brain signature," which could be targeted for intervention.

Additional Experimental Data Regarding the Disclosed Models

Table 7, below, shows metrics of the median mean square error (MSE), $r^2$ or variance explained, and p or features with non-zero regression coefficients for the three different model algorithms using the input feature set of individual scale items.

TABLE 7

Models with Scales as Input Feature Set

Scales Only Input Features

| | | Model Algorithm | | |
|---|---|---|---|---|
| Outcome Variables | Metric | Lasso | ElasticNet | RandomForest |
| Mood/Dep_Hopkins | median MSE | 0.120 | 0.148 | 0.160 |
| | median $r^2$ | 0.550 | 0.530 | 0.510 |
| | p | 30 | 50 | n/a |
| Mood_Bipolar | median MSE | 1.486 | 1.183 | 1.685 |
| | median $r^2$ | 0.791 | 0.836 | 0.745 |
| | p | 53 | 112 | n/a |

TABLE 7-continued

Models with Scales as Input Feature Set

Scales Only Input Features

| | | Model Algorithm | | |
|---|---|---|---|---|
| Outcome Variables | Metric | Lasso | ElasticNet | RandomForest |
| Anhedonia_Chapphy | median MSE | 22.145 | 19.670 | 30.152 |
| | median $r^2$ | 0.627 | 0.642 | 0.469 |
| | p | 30 | 240 | n/a |
| Anhedonia_Chapsoc | median MSE | 11.127 | 12.510 | 20.134 |
| | median $r^2$ | 0.796 | 0.782 | 0.651 |
| | P | 60 | 126 | n/a |
| Anxiety_Hopkins | median MSE | 0.123 | 0.134 | 0.183 |
| | median $r^2$ | 0.561 | 0.525 | 0.471 |
| | P | 16 | 54 | n/a |
| Anxiety_Bipolar | median MSE | 1.144 | 1.252 | 1.569 |
| | median $r^2$ | 0.608 | 0.616 | 0.523 |
| | P | 55 | 62 | n/a |

Table 8, below, shows metrics of median square error (MSE), $r^2$ or variance explained, and p or features with non-zero regression coefficients for the three different model algorithms using the input feature set of sMRI measures (subcortical volume, cortical volume, etc.).

TABLE 8

Models with sMRI as Input Feature Set.

sMRI Only Input Features

| | | Model Algorithm | | |
|---|---|---|---|---|
| Outcome Variables | Metric | Lasso | ElasticNet | RandomForest |
| Mood/Dep_Hopkins | median MSE | 0.282 | 0.299 | 0.283 |
| | median $r^2$ | 0.026 | 0.019 | 0.073 |
| | P | 4 | 3 | n/a |
| Mood_Bipolar | median MSE | 6.604 | 6.408 | 5.957 |
| | median $r^2$ | 0.041 | 0.123 | 0.135 |
| | P | 15 | 22 | n/a |
| Anhedonia_Chapphy | median MSE | 45.608 | 42.835 | 51.740 |
| | median $r^2$ | 0.083 | 0.158 | 0.019 |
| | P | 29 | 61 | n/a |
| Anhedonia_Chapsoc | median MSE | 46.644 | 43.893 | 48.993 |
| | median $r^2$ | 0.131 | 0.065 | 0.072 |
| | P | 32 | 32 | n/a |
| Anxiety_Hopkins | median MSE | 0.262 | 0.260 | 0.306 |
| | median $r^2$ | 0.035 | 0.042 | 0.042 |
| | P | 3 | 6 | n/a |
| Anxiety_Bipolar | median MSE | 2.966 | 2.865 | 3.166 |
| | median $r^2$ | 0.055 | 0.121 | 0.034 |
| | P | 15 | 16 | n/a |

Table 9, below, shows metrics of median square error (MSE), $r^2$ or variance explained, and p or features with non-zero regression coefficients for the three different model algorithms using the input feature set of fMRI connectivity features.

TABLE 9

Models with fMRI as Input Feature Set.

| Predicted Scores | Metric | Lasso | ElasticNet | RandomForest |
|---|---|---|---|---|
| Chapman Social Anhedonia | median MSE | 24.1366711 | 13.2464801 | 35.74676667 |
| | median $r^2$ | 0.5908661 | 0.7319229 | 0.258061818 |
| | p | 75 | 345 | n/a |
| Chapman Physical Anhedonia | median MSE | 30.901329 | 21.4057029 | 39.74679883 |
| | median $r^2$ | 0.61525222 | 0.65566807 | 0.247477881 |
| | p | 76 | 358 | n/a |
| HAMD, total score | median MSE | 33.2005788 | 38.9725415 | 71.34669412 |
| | median $r^2$ | 0.66777371 | 0.59569346 | 0.207388274 |
| | p | 16 | 500 | n/a |

TABLE 9-continued

| | Models with fMRI as Input Feature Set. | | | |
|---|---|---|---|---|
| Predicted Scores | Metric | Lasso | ElasticNet | RandomForest |
| HAMD, q1, 7, 8 sum score | median MSE | 0.95578396 | 0.91593487 | 2.650023529 |
| | median $r^2$ | 0.79179955 | 0.74061902 | 0.332485876 |
| | p | 28 | 191 | n/a |
| HAMD, q7 | median MSE | 0.31201916 | 0.37790437 | 0.808070588 |
| | median $r^2$ | 0.73200199 | 0.69881084 | 0.356340961 |
| | P | 38 | 54 | n/a |
| BPRS, negative score | median MSE | 0.18757938 | 0.1506109 | 0.241262868 |
| | median $r^2$ | 0.58051551 | 0.57369558 | 0.279867098 |
| | P | 15 | 131 | n/a |
| BPRS, depression-anxiety score | median MSE | 0.48898993 | 0.38228361 | 0.69174958 |
| | median $r^2$ | 0.51218225 | 0.54291803 | 0.343333691 |
| | p | 23 | 36 | n/a |
| Hopkins, anxiety score | median MSE | 0.16332994 | 0.10991548 | 0.250750368 |
| | median $r^2$ | 0.4518252 | 0.65341477 | 0.307182751 |
| | p | 24 | 85 | n/a |
| Hopkins, depression score | median MSE | 0.14661675 | 0.1591489 | 0.206618425 |
| | median $r^2$ | 0.48845674 | 0.45016098 | 0.280274072 |
| | p | 31 | 29 | n/a |
| Bipolar II, depression score | median MSE | 2.2093303 | 2.53026198 | 4.058693333 |
| | median $r^2$ | 0.64341678 | 0.62534857 | 0.323775594 |
| | p | 50 | 255 | n/a |
| Bipolar II, anxiety score | median MSE | 1.74502231 | 0.98772213 | 2.523746667 |
| | median $r^2$ | 0.48106 | 0.6442545 | 0.304516018 |
| | p | 43 | 153 | n/a |
| SANS, anhedonia factor score | median MSE | 0.57249993 | 0.44668826 | 0.671989773 |
| | median $r^2$ | 0.54341834 | 0.72603119 | 0.476297105 |
| | P | 16 | 66 | n/a |
| SANS, avolition factor score | median MSE | 0.38427335 | 0.41349887 | 0.523188636 |
| | median $r^2$ | 0.60922858 | 0.68171714 | 0.393902033 |
| | P | 20 | 63 | n/a |
| SANS, blunt affect factor score | median MSE | 0.35097663 | 0.13853868 | 0.319771716 |
| | median $r^2$ | 0.36340364 | 0.81112876 | 0.421756359 |
| | p | 22 | 29 | n/a |
| SANS, alogia factor score | median MSE | 0.1804207 | 0.0918634 | 0.208887871 |
| | median $r^2$ | 0.57666364 | 0.78317095 | 0.406578967 |
| | p | 15 | 37 | n/a |
| SANS, attention factor score | median MSE | 0.5114133 | 0.5450171 | 0.863740909 |
| | median $r^2$ | 0.58044727 | 0.55803846 | 0.351176332 |
| | p | 11 | 16 | n/a |
| SANS, anhedonia global score | median MSE | 0.6479366 | 0.653431 | 0.703936364 |
| | median $r^2$ | 0.57849286 | 0.5910022 | 0.567246117 |
| | p | 13 | 22 | n/a |
| SANS, avolition global score | median MSE | 0.65626457 | 0.45879379 | 1.112490909 |
| | median $r^2$ | 0.65501818 | 0.7356483 | 0.41697963 |
| | p | 8 | 126 | n/a |
| SANS, blunt affect global score | median MSE | 0.76806032 | 0.40498193 | 0.725527273 |
| | median $r^2$ | 0.5075324 | 0.67717999 | 0.438660494 |
| | p | 20 | 18 | n/a |
| SANS, alogia global score | median MSE | 0.18058636 | 0.25612571 | 0.360454545 |
| | median $r^2$ | 0.71239653 | 0.44974554 | 0.20472973 |
| | p | 12 | 21 | n/a |
| SANS, attention global score | median MSE | 0.82370349 | 0.84473842 | 1.018854545 |
| | median $r^2$ | 0.53408014 | 0.55862342 | 0.381446429 |
| | p | 8 | 70 | n/a |

Table 10, below, shows metrics of median square error (MSE), $r^2$ or variance explained, and p or features with non-zero regression coefficients for the three different model algorithms using the input feature set of sMRI and fMRI items.

TABLE 10

| | Models with sMRI + fMRI as Input Feature Set. | | | |
|---|---|---|---|---|
| Predicted Scores | Metric | Lasso | ElasticNet | RandomForest |
| Chapman Social Anhedonia | median MSE | 20.3800964 | 14.682152 | 34.56825833 |
| | median $r^2$ | 0.61287335 | 0.67729341 | 0.271666677 |
| | p | 30 | 559 | n/a |
| Chapman Physical Anhedonia | median MSE | 29.5944321 | 14.4191528 | 39.64058054 |
| | median $r^2$ | 0.47730737 | 0.73988389 | 0.270972364 |
| | p | 72 | 211 | n/a |

TABLE 10-continued

Models with sMRI + fMRI as Input Feature Set.

| Predicted Scores | Metric | Lasso | ElasticNet | RandomForest |
|---|---|---|---|---|
| HAMD, total score | median MSE | 40.444502 | 27.0655892 | 65.45605995 |
| | median $r^2$ | 0.46827069 | 0.61111933 | 0.317391988 |
| | p | 13 | 448 | n/a |
| HAMD, q1, 7, 8 sum score | median MSE | 2.36930173 | 1.3053619 | 2.42418007 |
| | median $r^2$ | 0.57469992 | 0.78027275 | 0.415661799 |
| | p | 21 | 78 | n/a |
| HAMD, q7 | median MSE | 0.48427727 | 0.44843705 | 0.733507692 |
| | median $r^2$ | 0.51760748 | 0.62850068 | 0.374694444 |
| | p | 4 | 95 | n/a |
| BPRS, negative score | median MSE | 0.10894905 | 0.20808541 | 0.228798077 |
| | median $r^2$ | 0.58309527 | 0.48416688 | 0.339701299 |
| | p | 10 | 12 | n/a |
| BPRS, depression-anxiety score | median MSE | 0.74672192 | 0.4527803 | 0.745567681 |
| | median $r^2$ | 0.34811518 | 0.59421236 | 0.305609826 |
| | p | 15 | 119 | n/a |
| Hopkins, anxiety score | median MSE | 0.12090694 | 0.09822079 | 0.189571301 |
| | median $r^2$ | 0.55139531 | 0.65036656 | 0.303938076 |
| | p | 8 | 29 | n/a |
| Hopkins, depression score | median MSE | 0.17540687 | 0.1383836 | 0.199493796 |
| | median $r^2$ | 0.38018872 | 0.4151432 | 0.199243267 |
| | p | 21 | 16 | n/a |
| Bipolar II, depression score | median MSE | 3.58417568 | 1.86722182 | 4.104375843 |
| | median $r^2$ | 0.45476109 | 0.71921058 | 0.297745091 |
| | p | 48 | 241 | n/a |
| Bipolar II, anxiety score | median MSE | 1.28026365 | 0.70325067 | 2.257191667 |
| | median $r^2$ | 0.60209066 | 0.78935698 | 0.32304625 |
| | p | 25 | 161 | n/a |
| SANS, anhedonia factor score | median MSE | 0.40512803 | 0.35700521 | 0.63381875 |
| | median $r^2$ | 0.71570239 | 0.77152059 | 0.552279155 |
| | p | 8 | 48 | n/a |
| SANS, avolition factor score | median MSE | 0.18738998 | 0.11302804 | 0.45203125 |
| | median $r^2$ | 0.67281 | 0.84257768 | 0.519285076 |
| | p | 7 | 41 | n/a |
| SANS, blunt affect factor score | median MSE | 0.1055558 | 0.16598636 | 0.406562166 |
| | median $r^2$ | 0.7535557 | 0.76532171 | 0.476367098 |
| | p | 24 | 65 | n/a |
| SANS, alogia factor score | median MSE | 0.40859079 | 0.11637806 | 0.236031927 |
| | median $r^2$ | 0.29255013 | 0.7725277 | 0.559877681 |
| | p | 7 | 77 | n/a |
| SANS, attention factor score | median MSE | 0.57872686 | 0.43584679 | 0.648390625 |
| | median $r^2$ | 0.6007934 | 0.60740377 | 0.31332093 |
| | p | 13 | 93 | n/a |
| SANS, anhedonia global score | median MSE | 0.88823187 | 0.57576394 | 1.095494073 |
| | median $r^2$ | 0.40161221 | 0.63872035 | 0.319304654 |
| | p | 17 | 107 | n/a |
| SANS, avolition global score | median MSE | 0.55331606 | 0.21081588 | 0.7125 |
| | median $r^2$ | 0.56105366 | 0.82726123 | 0.5096 |
| | p | 6 | 67 | n/a |
| SANS, blunt affect global score | median MSE | 0.76193885 | 0.26705401 | 0.75875 |
| | median $r^2$ | 0.5411395 | 0.84012485 | 0.526436782 |
| | p | 11 | 41 | n/a |
| SANS, alogia global score | median MSE | 0.52887025 | 0.25762776 | 0.3487375 |
| | median $r^2$ | 0.31534639 | 0.65101623 | 0.320888889 |
| | p | 8 | 26 | n/a |
| SANS, attention global score | median MSE | 0.35172813 | 0.28886716 | 0.5875 |
| | median $r^2$ | 0.70380789 | 0.75674345 | 0.5975 |
| | p | 8 | 13 | n/a |

Table 11, below, shows metrics of median square error (MSE), $r^2$ or variance explained, and p or features with non-zero regression coefficients for the three different model algorithms using the input feature set of individual scale items and sMRI features.

TABLE 11

Models with Scales + sMRI as Input Feature Set.

| Predicted Scores | Metric | Lasso | ElasticNet | RandomForest |
|---|---|---|---|---|
| Chapman Social Anhedonia | median MSE | 10.1872913 | 10.8473571 | 23.01353415 |
| | median $r^2$ | 0.8189687 | 0.79591289 | 0.599748178 |
| | p | 59 | 63 | n/a |

TABLE 11-continued

| | Models with Scales + sMRI as Input Feature Set. | | | |
|---|---|---|---|---|
| Predicted Scores | Metric | Lasso | ElasticNet | RandomForest |
| Chapman Physical Anhedonia | median MSE | 15.1648738 | 15.1775051 | 31.00075366 |
| | median $r^2$ | 0.6745091 | 0.69034822 | 0.429974564 |
| | p | 92 | 123 | n/a |
| HAMD, total score | median MSE | 44.8743169 | 21.4111889 | 51.17416788 |
| | median $r^2$ | 0.62386495 | 0.80822534 | 0.600713723 |
| | p | 31 | 123 | n/a |
| HAMD, q1, 7,8 sum score | median MSE | 2.04269051 | 1.25720156 | 2.447818182 |
| | median $r^2$ | 0.59849127 | 0.76841313 | 0.474861019 |
| | p | 38 | 110 | n/a |
| HAMD, q7 | median MSE | 0.5660152 | 0.37695234 | 0.771495455 |
| | median $r^2$ | 0.60961318 | 0.73435387 | 0.407349419 |
| | p | 28 | 58 | n/a |
| BPRS, negative score | median MSE | 0.22947823 | 0.11052677 | 0.223487784 |
| | median $r^2$ | 0.3567901 | 0.68800207 | 0.426280069 |
| | p | 12 | 54 | n/a |
| BPRS, depression-anxiety score | median MSE | 0.47774909 | 0.37200915 | 0.716768024 |
| | median $r^2$ | 0.6784626 | 0.76758706 | 0.520999457 |
| | p | 39 | 58 | n/a |
| Hopkins, anxiety score | median MSE | 0.15278469 | 0.14505891 | 0.147720373 |
| | median $r^2$ | 0.46629576 | 0.47103414 | 0.475010058 |
| | p | 14 | 49 | n/a |
| Hopkins, depression score | median MSE | 0.13015768 | 0.10560835 | 0.148762648 |
| | median $r^2$ | 0.58405287 | 0.67747487 | 0.516387069 |
| | p | 15 | 102 | n/a |
| Bipolar II, depression score | median MSE | 1.11473489 | 1.02057729 | 1.722802026 |
| | median $r^2$ | 0.84118256 | 0.86421896 | 0.745336441 |
| | p | 32 | 114 | n/a |
| Bipolar II, anxiety score | median MSE | 0.81608355 | 0.79832926 | 1.565412195 |
| | median $r^2$ | 0.7409768 | 0.73479011 | 0.523792469 |
| | p | 30 | 58 | n/a |
| SANS, anhedonia factor score | median MSE | 0.80659301 | 0.8876104 | 1.02542 |
| | median $r^2$ | 0.4847042 | 0.43714204 | 0.251376657 |
| | p | 24 | 13 | n/a |
| SANS, avolition factor score | median MSE | 0.35767455 | 0.29545236 | 0.76713875 |
| | median $r^2$ | 0.64133778 | 0.69348871 | 0.252067852 |
| | p | 30 | 54 | n/a |
| SANS, blunt affect factor score | median MSE | 0.29046712 | 0.35398284 | 0.555033335 |
| | median $r^2$ | 0.65317772 | 0.57650195 | 0.346361453 |
| | p | 15 | 29 | n/a |
| SANS, alogia factor score | median MSE | 0.27355305 | 0.22486147 | 0.370562213 |
| | median $r^2$ | 0.43984006 | 0.45944781 | 0.260900092 |
| | p | 16 | 22 | n/a |
| SANS, attention factor score | median MSE | 0.61391724 | 0.52919515 | 0.840366667 |
| | median $r^2$ | 0.42634181 | 0.56616671 | 0.26694625 |
| | p | 15 | 90 | n/a |
| SANS, anhedonia global score | median MSE | 0.82696728 | 0.91638191 | 1.31 |
| | median $r^2$ | 0.52922904 | 0.52124193 | 0.349258197 |
| | p | 16 | 57 | n/a |
| SANS, avolition global score | median MSE | 1.0735851 | 0.96201314 | 1.69874 |
| | median $r^2$ | 0.48944093 | 0.4703767 | 0.186773404 |
| | p | 15 | 92 | n/a |
| SANS, blunt affect global score | median MSE | 0.47919468 | 0.64615998 | 0.941919557 |
| | median $r^2$ | 0.56575973 | 0.5970739 | 0.403780513 |
| | p | 16 | 89 | n/a |
| SANS, alogia global score | median MSE | 0.42319702 | 0.51674167 | 0.709333333 |
| | median $r^2$ | 0.41947137 | 0.43807514 | 0.181628238 |
| | p | 15 | 16 | n/a |
| SANS, attention global score | median MSE | 0.5766073 | 0.87984786 | 1.165269856 |
| | median $r^2$ | 0.53935525 | 0.37445084 | 0.141182351 |
| | p | 23 | 56 | n/a |

Table 12, below, shows metrics of median square error (MSE), $r^2$ or variance explained, and p or features with non-zero regression coefficients for the three different model algorithms using the input feature set of individual scale items and fMRI features.

TABLE 12

Models with Scales + fMRI as Input Feature Set.

Scales + fMRI Input Features

| Outcome Variables | Metric | Model Algorithm | | |
|---|---|---|---|---|
| | | Lasso | ElasticNet | RandomForest |
| Mood/Dep_Hopkins | median MSE | 0.077 | 0.110 | 0.205 |
| | median $r^2$ | 0.709 | 0.610 | 0.360 |
| | P | 16 | 26 | n/a |
| Mood_Bipolar | median MSE | 0.861 | 0.814 | 3.003 |
| | median $r^2$ | 0.869 | 0.874 | 0.600 |
| | P | 50 | 236 | n/a |
| Anhedonia_Chapphy | median MSE | 11.439 | 9.648 | 35.942 |
| | median $r^2$ | 0.805 | 0.841 | 0.349 |
| | P | 46 | 211 | n/a |
| Anhedonia_Chapsoc | median MSE | 7.549 | 8.627 | 23.482 |
| | median $r^2$ | 0.857 | 0.829 | 0.486 |
| | p | 47 | 31 | n/a |
| Anxiety_Hopkins | median MSE | 0.150 | 0.095 | 0.205 |
| | median $r^2$ | 0.597 | 0.704 | 0.312 |
| | p | 27 | 127 | n/a |
| Anxiety_Bipolar | median MSE | 0.928 | 0.589 | 1.782 |
| | median $r^2$ | 0.729 | 0.825 | 0.469 |
| | p | 31 | 32 | n/a |

Table 13, below, shows metrics of median square error (MSE), $r^2$ or variance explained, and p or features with non-zero regression coefficients for the three different model algorithms using the input feature set of individual scale items, sMRI, and fMRI features.

TABLE 13

Models with Scales + sMRI + fMRI as Input Feature Set.

Scales + sMRI + fMRI Input Features

| Outcome Variables | Metric | Model Algorithm | | |
|---|---|---|---|---|
| | | Lasso | ElasticNet | RandomForest |
| Mood/Dep_Hopkins | median MSE | 0.132 | 0.076 | 0.129 |
| | median $r^2$ | 0.514 | 0.721 | 0.470 |
| | p | 8 | 28 | n/a |
| Mood_Bipolar | median MSE | 0.724 | 0.614 | 2.163 |
| | median $r^2$ | 0.874 | 0.904 | 0.658 |
| | p | 31 | 93 | n/a |
| Anhedonia_Chapphy | median MSE | 23.104 | 15.814 | 27.952 |
| | median $r^2$ | 0.620 | 0.652 | 0.259 |
| | p | 48 | 32 | n/a |
| Anhedonia_Chapsoc | median MSE | 7.027 | 9.886 | 25.091 |
| | median $r^2$ | 0.822 | 0.804 | 0.438 |
| | P | 30 | 106 | n/a |
| Anxiety_Hopkins | median MSE | 0.086 | 0.077 | 0.149 |
| | median $r^2$ | 0.684 | 0.751 | 0.420 |
| | P | 27 | 47 | n/a |
| Anxiety_Bipolar | median MSE | 0.521 | 0.535 | 1.745 |
| | median $r^2$ | 0.838 | 0.847 | 0.435 |
| | P | 72 | 31 | n/a |

Table 14, below, shows Wilcoxon rank-sum U statistics and p-values for a post hoc group-comparison statistic of significantly different motion measures shown in FIGS. 7A-7I. Significant p-values can be identified from the table.

TABLE 14

Post-hoc group comparison statistic of significantly different motion measures shown in FIGS. 7A-7I.

Motion Measures

| Group Comparison | Mean FD | Sharp Motion | Y-axis Motion | Z-axis Motion |
|---|---|---|---|---|
| HC v. SZ | U stat = 162 | U stat = 151 | U stat = 167 | U stat = 174 |
| | p = 0.0005 | p = 0.0003 | p = 0.0007 | p = 0.0010 |
| HC v. BD | U stat = 458 | U stat = 435 | U stat = 438 | U stat = 434 |
| | p = 0.0112 | p = 0.0058 | p = 0.0063 | p = 0.0056 |
| HC v. ADHD | U stat = 581 | U stat = 600 | U stat = 628 | U stat = 481 |
| | p = 0.2358 | p = 0.3035 | p = 0.4164 | p = 0.0357 |
| SZ v. BD | U stat = 132 | U stat = 139 | U stat = 140 | U stat = 140 |
| | p = 0.1067 | p = 0.1493 | p = 0.1562 | p = 0.1562 |
| SZ v. ADHD | U stat = 91 | U stat = 90 | U stat = 77 | U stat = 112 |
| | p = 0.0103 | p = 0.0095 | p = 0.0031 | p = 0.0465 |
| BD v. ADHD | U stat = 232 | U stat = 219 | U stat = 205 | U stat = 251 |
| | p = 0.0885 | p = 0.0537 | p = 0.0294 | p = 0.1660 |

Additional Embodiments

Additional aspects of the present disclosure include the following method: Clinical scale data, resting-state functional-MRI data, and structural-MRI scans are received for multiple patients with schizophrenia, bipolar disorder, attention deficit and hyperactivity disorder ("ADHD"), or healthy controls. The received data are preprocessed. At least one predictive model of symptom expression is generated based on the preprocessed data. Subsets of features in the received data are identified from the at least one predictive model to predict transdiagnostic symptoms related to depression, anxiety, anhedonia, and other negative symptoms.

Further aspects of the present disclosure include the following computer system: A computing system includes at least one database, a memory, and a processor. The database stores clinical scale data, resting-state functional-MRI data, and structural-MRI scans for multiple patients with schizophrenia, bipolar disorder, ADHD, or healthy controls. The memory stores computer instructions. The processor that is configured to execute the computer instructions to preprocess the data stored in the at least one database. At least one predictive model of symptom expression is generated based on the preprocessed data. Subsets of features in the received data are identified from the at least one predictive model to predict transdiagnostic symptoms related to depression, anxiety, anhedonia, and other negative symptoms.

Although the present disclosure provides for models trained on the CNP database, the present disclosure contemplates that any database comprising clinical scales data and MRI data can be used to produce models, as would be readily contemplated by one skilled in the art.

The disclosed models selected as informative the features which trend in the same direction for all participants. The present disclosure contemplates that brain activity can be examined which diverges between patient groups; such an approach can yield other features.

Although the present disclosure discusses input primarily in terms of fMRI data and sMRI data, other embodiments can provide for receiving rs-fMRI.

Altogether, the present disclosure provides a data-driven way to improve biomarker development for predicting symptom severity transdiagnostically and can be used in a personalized medicine approach in diagnosing and treating behavioral disorders.

Machine Learning Implementation

Various aspects of the present disclosure can be performed by a machine-learning algorithm, as readily understood by a person skilled in the art. In some examples, step 1540 of FIG. 15 and methodology 1600 of FIG. 16 can be performed by a supervised or unsupervised algorithm. For instance, the system may utilize more basic machine learning tools including 1) decision trees ("DT"), (2) Bayesian networks ("BN"), (3) artificial neural network ("ANN"), or (4) support vector machines ("SVM"). In other examples, deep learning algorithms or other more sophisticated machine learning algorithms, e.g., convolutional neural networks ("CNN"), or capsule networks ("CapsNet") may be used.

DT are classification graphs that match input data to questions asked at each consecutive step in a decision tree. The DT program moves down the "branches" of the tree based on the answers to the questions (e.g., First branch: Did the clinical scales data include certain input? yes or no. Branch two: Did the MRI data include certain features? yes or no, etc.).

Bayesian networks ("BN") are based on likelihood something is true based on given independent variables and are modeled based on probabilistic relationships. BN are based purely on probabilistic relationships that determine the likelihood of one variable based on another or others. For example, BN can model the relationships between MRI data, clinical scales data, and any other information as contemplated by the present disclosure. Particularly, if a question type and particular features of the patient's MRI data are known, a BN can be used to compute a symptom severity indicator. Thus, using an efficient BN algorithm, an inference can be made based on the input data.

Artificial neural networks ("ANN") are computational models inspired by an animal's central nervous system. They map inputs to outputs through a network of nodes. However, unlike BN, in ANN the nodes do not necessarily represent any actual variable. Accordingly, ANN may have a hidden layer of nodes that are not represented by a known variable to an observer. ANNs are capable of pattern recognition. Their computing methods make it easier to understand a complex and unclear process that might go on during determining a symptom severity indicator based on a variety of input data.

Support vector machines ("SVM") came about from a framework utilizing of machine learning statistics and vector spaces (linear algebra concept that signifies the number of dimensions in linear space) equipped with some kind of limit-related structure. In some cases, they may determine a new coordinate system that easily separates inputs into two classifications. For example, a SVM could identify a line that separates two sets of points originating from different classifications of events.

Deep neural networks (DNN) have developed recently and are capable of modeling very complex relationships that have a lot of variation. Various architectures of DNN have been proposed to tackle the problems associated with algorithms such as ANN by many researchers during the last few decades. These types of DNN are CNN (Convolutional Neural Network), RBM (Restricted Boltzmann Machine), LSTM (Long Short Term Memory) etc. They are all based on the theory of ANN. They demonstrate a better performance by overcoming the back-propagation error diminishing problem associated with ANN.

Machine learning models require training data to identify the features of interest that they are designed to detect. For instance, various methods may be utilized to form the machine learning models, including applying randomly assigned initial weights for the network and applying gradient descent using back propagation for deep learning algorithms. In other examples, a neural network with one or two hidden layers can be used without training using this technique.

In some examples, the machine learning model can be trained using labeled data, or data that represents certain user input. In other examples, the data will only be labeled with the outcome and the various relevant data may be input to train the machine learning algorithm.

For instance, to determine whether particular mental health disorder fits the input data, various machine learning models may be utilized that input various data disclosed herein. In some examples, the input data will be labeled by having an expert in the field label the relevant regulations according to the particular situation. Accordingly, the input to the machine learning algorithm for training data identifies various data as from a healthy control or from a patient.

Exemplary NMR System

Figure 17A:
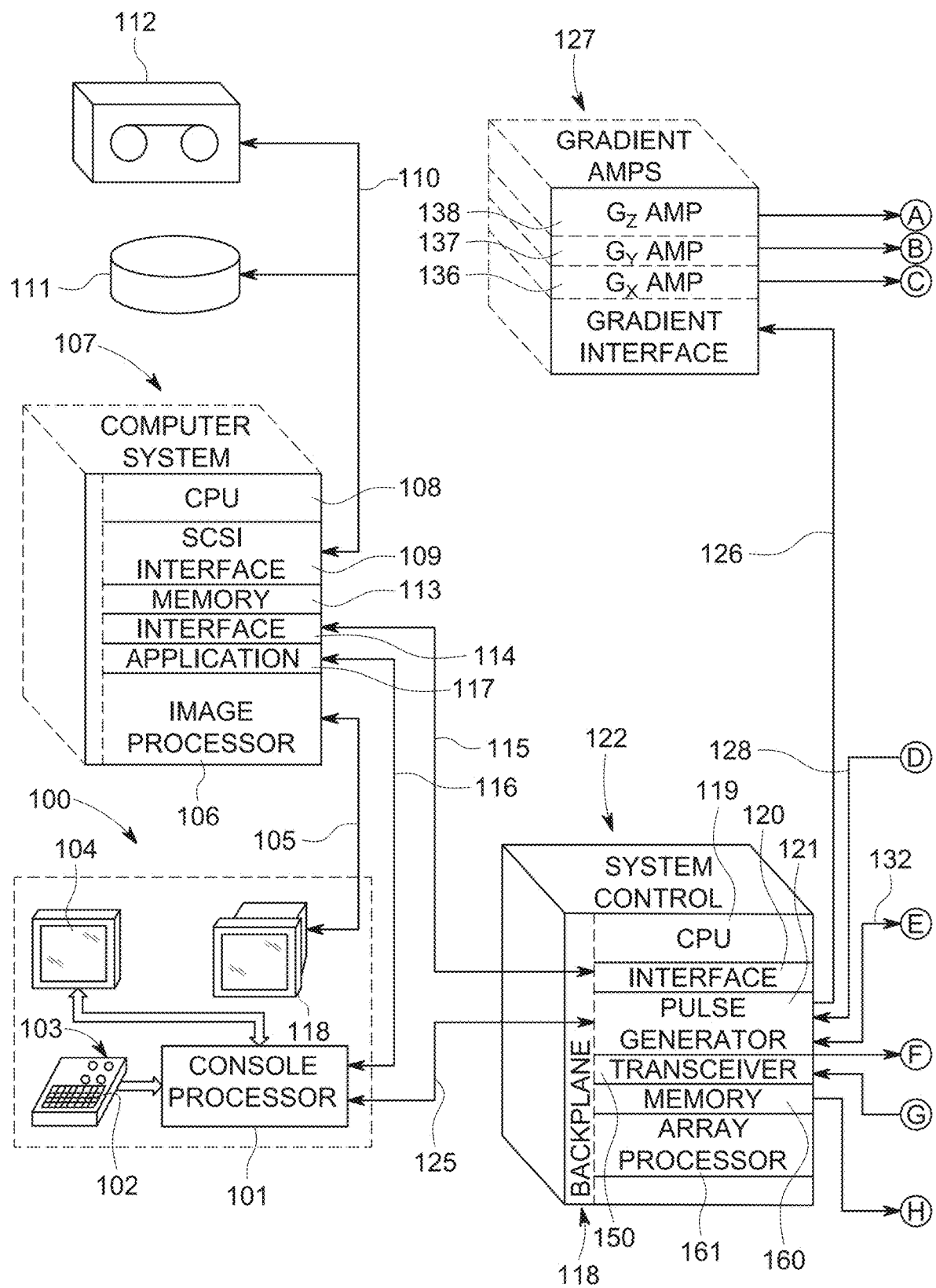
FIGS. 17A-17B illustrate a block diagram of an MRI system used to acquire NMR data, according to some implementations of the present disclosure.
Figure 17B:
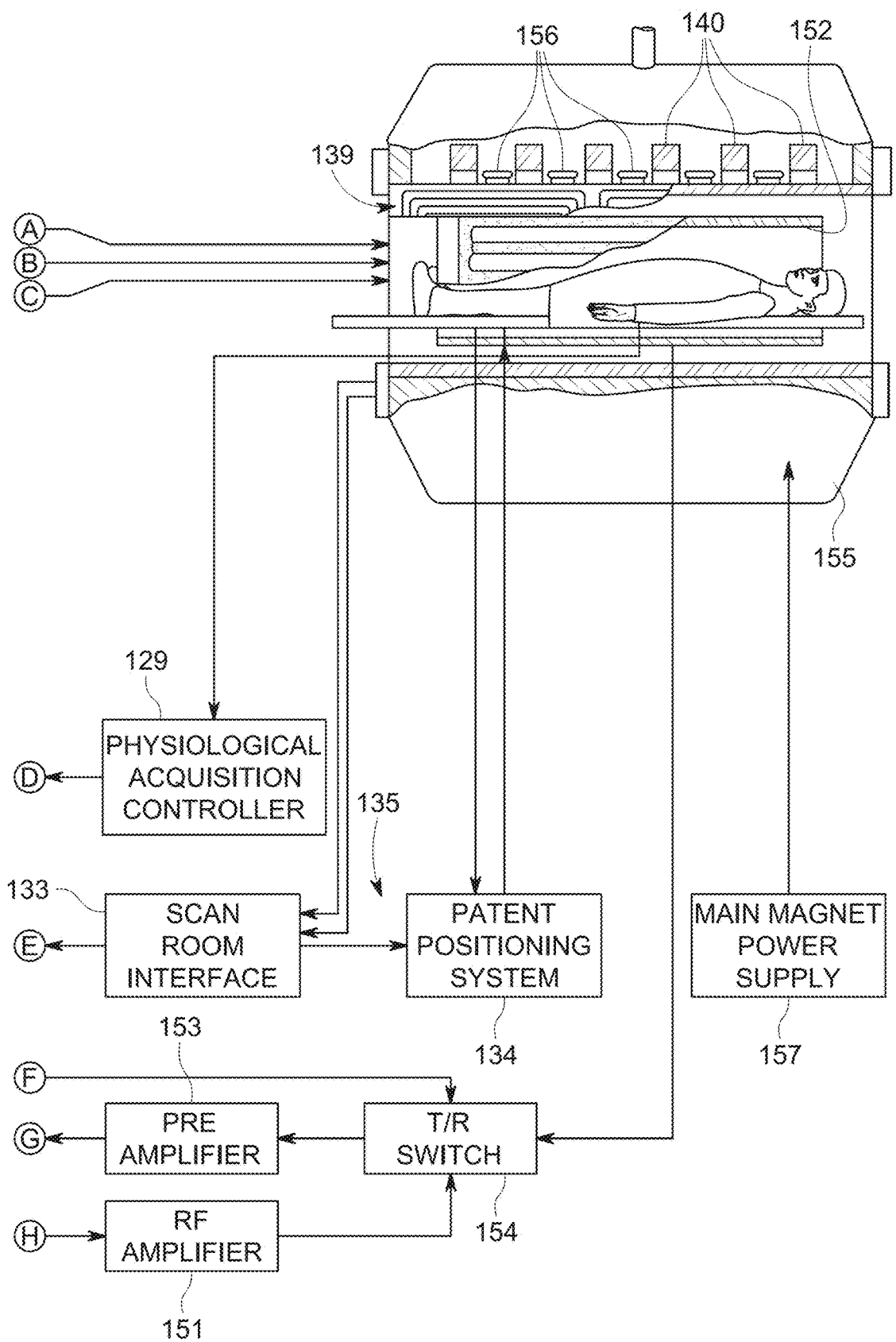
Figure 18:
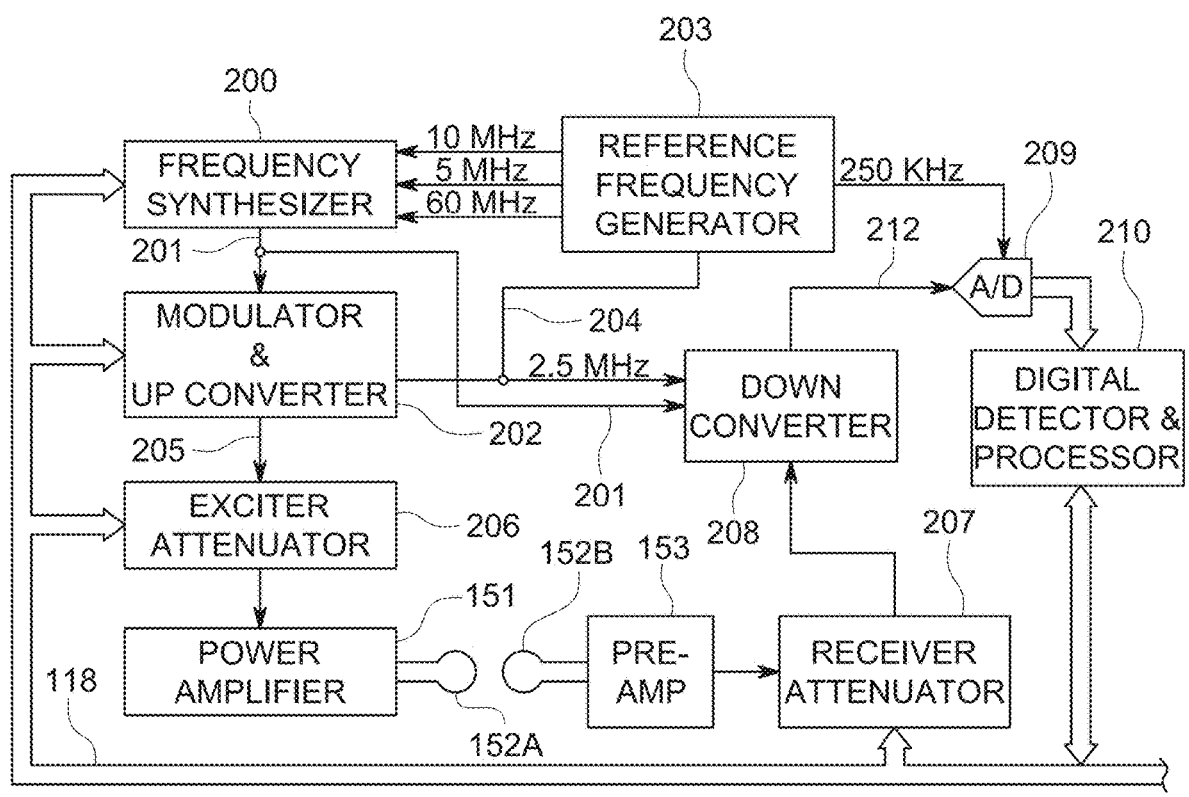
FIG. 18 illustrates a block diagram of a transceiver which forms part of the MRI system of FIG. 17A.

Referring now to FIGS. 17A-18, the methods and embodiments of the present disclosure can be performed on an exemplary nuclear magnetic resonance ("NMR system"). As a person of ordinary skill in the art understands, NMR commonly refers to the hardware used to generate different types of scans, including MRI scans. Referring now to FIGS. 17A-18, there is shown the major components of an NMR system which can be used to carry out the methods of the various embodiments. FIG. 18 shows the components of an exemplary transceiver for the NMR system of FIGS. 17A-17B. It should be noted that the methods of the various embodiments can also be carried out using other NMR systems.

The operation of the system of FIGS. 17A-18 is controlled from an operator console 100 which includes a console processor 101 that scans a keyboard 102 and receives inputs from a human operator through a control panel 103 and a plasma display/touch screen 104. The console processor 101 communicates through a communications link 116 with an applications interface module 117 in a separate computer system 107. Through the keyboard 102 and controls 103, an operator controls the production and display of images by an image processor 106 in the computer system 107, which connects directly to a video display 118 on the console 100 through a video cable 105.

The computer system 107 is formed about a backplane bus which conforms with the VME standards, and it includes a number of modules which communicate with each other through this backplane. In addition to the application interface 117 and the image processor 106, these include a CPU module 108 that controls the VME backplane, and an SCSI interface module 109 that connects the computer system 107 through a bus 110 to a set of peripheral devices, including disk storage 111 and tape drive 112. The computer system 107 also includes a memory module 113, known in the art as a frame buffer for storing image data arrays, and a serial interface module 114 that links the computer system 107 through a high speed serial link 115 to a system interface module 120 located in a separate system control cabinet 122.

The system control 122 includes a series of modules which are connected together by a common backplane 118. The backplane 118 is comprised of a number of bus structures, including a bus structure which is controlled by a CPU module 119. The serial interface module 120 connects this backplane 118 to the high speed serial link 115, and pulse generator module 121 connects the backplane 118 to the operator console 100 through a serial link 125. It is through this link 125 that the system control 122 receives commands from the operator which indicate the scan sequence that is to be performed.

The pulse generator module 121 operates the system components to carry out the desired scan sequence. It produces data which indicates the timing, strength and shape of the RF pulses which are to be produced, and the timing of and length of the data acquisition window. The pulse generator module 121 also connects through serial link 126 to a set of gradient amplifiers 127, and it conveys data thereto which indicates the timing and shape of the gradient pulses that are to be produced during the scan. The pulse generator module 121 also receives patient data through a serial link 128 from a physiological acquisition controller 129. The physiological acquisition control 129 can receive a signal from a number of different sensors connected to the patient. For example, it may receive ECG signals from electrodes or respiratory signals from a bellows and produce pulses for the pulse generator module 121 that synchronizes the scan with the patient's cardiac cycle or respiratory cycle. And finally, the pulse generator module 121 connects through a serial link 132 to scan room interface circuit 133 which receives signals at inputs 135 from various sensors associated with the position and condition of the patient and the magnet system. It is also through the scan room interface circuit 133 that a patient positioning system 134 receives commands which move the patient cradle and transport the patient to the desired position for the scan.

The gradient waveforms produced by the pulse generator module 121 are applied to a gradient amplifier system 127 comprised of Gx, Gy, and Gz amplifiers 136, 137 and 138, respectively. Each amplifier 136, 137, and 138 is utilized to excite a corresponding gradient coil in an assembly generally designated 139. The gradient coil assembly 139 forms part of a magnet assembly 155 which includes a polarizing magnet 140 that produces a 1.5 Tesla polarizing field that extends horizontally through a bore. The gradient coils 139 encircle the bore, and when energized, they generate magnetic fields in the same direction as the main polarizing magnetic field, but with gradients Gx, Gy and Gz directed in the orthogonal x-, y- and z-axis directions of a Cartesian coordinate system. That is, if the magnetic field generated by the main magnet 140 is directed in the z direction and is termed B0, and the total magnetic field in the z direction is referred to as Bz, then Gx=∂Bz/∂x, Gy=∂Bz/∂y and Gz=∂Bz/∂z, and the magnetic field at any point (x,y,z) in the bore of the magnet assembly 141 is given by B(x,y,z)=B0+Gxx+Gyy+Gzz. The gradient magnetic fields are utilized to encode spatial information into the NMR signals emanating from the patient being scanned. Because the gradient fields are switched at a very high speed when an EPI sequence is used to practice the preferred embodiment of the invention, local gradient coils are employed in place of the whole-body gradient coils 139. These local gradient coils are designed for the head and are in close proximity thereto. This enables the inductance of the local gradient coils to be reduced and the gradient switching rates increased as required for the EPI pulse sequence. For a description of these local gradient coils which is incorporated herein by reference, see U.S. Pat. No. 5,372,137 issued on Dec. 13, 1994, and entitled "NMR Local Coil For Brain Imaging".

Located within the bore 142 is a circular cylindrical whole-body RF coil 152. This coil 152 produces a circularly polarized RF field in response to RF pulses provided by a transceiver module 150 in the system control cabinet 122. These pulses are amplified by an RF amplifier 151 and coupled to the RF coil 152 by a transmit/receive switch 154 which forms an integral part of the RF coil assembly. Waveforms and control signals are provided by the pulse generator module 121 and utilized by the transceiver module 150 for RF carrier modulation and mode control. The resulting NMR signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150.

The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate local RF head coil to be used in the transmit and receive mode to improve the signal-to-noise ratio of the received NMR signals. With currently available NMR systems such a local RF coil is preferred in order to detect small variations in NMR signal. Reference is made to the above cited U.S. Pat. No. 5,372,137 for a description of the preferred local RF coil.

In addition to supporting the polarizing magnet 140 and the gradient coils 139 and RF coil 152, the main magnet assembly 141 also supports a set of shim coils 156 associated with the main magnet 140 and used to correct inhomogeneities in the polarizing magnet field. The main power supply 157 is utilized to bring the polarizing field produced by the superconductive main magnet 140 to the proper operating strength and is then removed.

The NMR signals picked up by the RF coil are digitized by the transceiver module 150 and transferred to a memory module 160 which is also part of the system control 122. When the scan is completed and an entire array of data has been acquired in the memory modules 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the video display 118 as will be described in more detail hereinafter.

Referring particularly to FIG. 18, the transceiver 150 includes components which produce the RF excitation field B1 through power amplifier 151 at a coil 152A and components which receive the resulting NMR signal induced in a coil 152B. As indicated above, the coils 152A and B may be a single whole-body coil, but the best results are achieved with a single local RF coil specially designed for the head. The base or carrier frequency of the RF excitation field is produced under control of a frequency synthesizer 200 which receives a set of digital signals (CF) through the backplane 118 from the CPU module 119 and pulse generator module 121. These digital signals indicate the frequency and phase of the RF carrier signal, which is produced at an output 201. The commanded RF carrier is applied to a modulator and up converter 202 where its amplitude is modulated in response to a signal R(t) also received through the backplane 118 from the pulse generator module 121. The signal R(t) defines the envelope, and therefore the bandwidth, of the RF excitation pulse to be produced. It is produced in the module 121 by sequentially reading out a series of stored digital values that represent the; desired envelope. These stored digital values may, in turn, be changed from the operator console 100 to enable any desired RF pulse envelope to be produced. The modulator and up converter 202 produces an RF pulse at the desired Larmor frequency at an output 205. The magnitude of the RF excitation pulse output through line 205 is attenuated by an exciter attenuator circuit 206 which receives a digital command, TA, from the backplane 118. The attenuated RF excitation pulses are applied to the power amplifier 151 that drives the RF coil 152A. For a more detailed description of this portion of the transceiver 122, reference is made to U.S. Pat. No. 4,952,877, which is incorporated herein by reference.

Referring still to FIGS. 17A-18, the NMR signal produced by the subject is picked up by the receiver coil 152B and applied through the preamplifier 153 to the input of a receiver attenuator 207. The receiver attenuator 207 further amplifies the NMR signal, and this is attenuated by an amount determined by a digital attenuation signal (RA) received from the backplane 118. The receive attenuator 207 is also turned on and off by a signal from the pulse generator module 121 such that it is not overloaded during RF excitation. The received NMR signal is at or around the Larmor frequency, which in the preferred embodiment is around 63.86 MHz for 1.5 Tesla. This high-frequency signal is down-converted in a two-step process by a down converter 208 which first mixes the NMR signal with the carrier signal on line 201 and then mixes the resulting difference signal with the 2.5 MHz reference signal on line 204. The resulting down-converted NMR signal on line 212 has a maximum bandwidth of 125 kHz, and it is centered at a frequency of 187.5 kHz. The down-converted NMR signal is applied to the input of an analog-to-digital (A/D) converter 209, which samples and digitizes the analog signal at a rate of 250 kHz. The output of the A/D converter 209 is applied to a digital detector, and signal processor 210 which produce 16-bit in-phase (I) values and 16-bit quadrature (Q) values corresponding to the received digital signal. The resulting stream of digitized I and Q values of the received NMR signal is output through backplane 118 to the memory module 160 where they are employed to reconstruct an image.

To preserve the phase information contained in the received NMR signal, both the modulator and up converter 202 in the exciter section and the down converter 208 in the receiver section are operated with common signals. More particularly, the carrier signal at the output 201 of the frequency synthesizer 200 and the 2.5 MHz reference signal at the output 204 of the reference frequency generator 203 are employed in both frequency conversion processes. Phase consistency is thus maintained, and phase changes in the detected NMR signal accurately indicate phase changes produced by the excited spins. The 2.5 MHz reference signal as well as 5, 10 and 60 MHz reference signals are produced by the reference frequency generator 203 from a common 20 MHz master clock signal. The latter three reference signals are employed by the frequency synthesizer 200 to produce the carrier signal on output 201. For a more detailed description of the receiver, reference is made to U.S. Pat. No. 4,992,736, which is incorporated herein by reference.

Computer & Hardware Implementation of Disclosure

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present invention, but merely be understood to illustrate one example implementation thereof.

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back-end component (e.g., as a data server) or a middleware component (e.g., an application server) or a front-end component (e.g., a client computer having a graphical user interface or a Web browser through which a user can interact with an implementation of the subject matter described in this specification) or any combination of one or more such back-end, middleware, or front-end components. The components of the system can be interconnected by any form or medium of digital data communication (e.g., a communication network). Examples of communication networks include a local area network ("LAN") and a wide area network ("WAN"), an internetwork (e.g., the Internet), and peer-to-peer networks (e.g., ad hoc peer-to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs (i.e., one or more modules of computer program instructions) encoded on computer storage medium for execution by, or to control the operation of, data processing apparatus. Alternatively or in addition, the program instructions can be encoded on an artificially-generated propagated signal (e.g., a machine-generated electrical, optical, or electromagnetic signal) that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry (e.g., an FPGA (field-programmable gate array) or an ASIC (application-specific integrated circuit)). The apparatus can also include, in addition to hardware, code that creates an execution environment for the computer program in question (e.g., code that constitutes processor firmware, a protocol stack, a database management system, an operating system, a cross-platform runtime environment, a virtual machine, or a combination of one or more of them). The apparatus and execution environment can realize various different computing model infrastructures, such as web services, distributed computing, and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry (e.g., an FPGA (field-programmable gate array) or an ASIC (application-specific integrated circuit)).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data (e.g., magnetic, magneto-optical disks, or optical disks). However, a computer need not have such devices. Moreover, a computer can be embedded in another device (e.g., a mobile telephone, a personal digital assistant (PDA), a mobile audio or video player, a game console, a Global Positioning System (GPS) receiver, or a portable storage device (e.g., a universal serial bus (USB) flash drive), to name just a few). Devices suitable for storing computer program instructions and data include all forms of non-volatile memory, media and memory devices, including by way of example semiconductor memory devices (e.g., EPROM, EEPROM, and flash memory devices; magnetic disks, e.g., internal hard disks or removable disks; magneto-optical disks; and CD-ROM and DVD-ROM disks). The processor and the memory can be supplemented by, or incorporated in, special purpose logic circuitry.

CONCLUSION

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features, and steps discussed above, as well as other known equivalents for each such element, feature or step, can be employed in various combinations by one of ordinary skill in this art to perform methods in accordance with the principles described herein. Among the various elements, features, and steps, some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

Particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

While various examples of the present disclosure have been described above, it should be understood that they have been presented by way of example only, and not limitation. Numerous changes to the disclosed examples can be made in accordance with the disclosure herein without departing from the spirit or scope of the disclosure. Thus, the breadth and scope of the present disclosure should not be limited by any of the above described examples. Rather, the scope of the disclosure should be defined in accordance with the following claims and their equivalents.

Although the disclosure has been illustrated and described with respect to one or more implementations, equivalent alterations and modifications will occur to others skilled in the art upon the reading and understanding of this specification and the annexed drawings. In addition, while a particular feature of the disclosure may have been disclosed with respect to only one of several implementations, such feature may be combined with one or more other features of the other implementations as may be desired and advantageous for any given or particular application.

The terminology used herein is for the purpose of describing particular examples only and is not intended to be limiting of the disclosure. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this disclosure belongs. Furthermore, terms, such as those defined in commonly used dictionaries, should be interpreted as having a meaning that is consistent with their meaning in the context of the relevant art, and will not be interpreted in an idealized or overly formal sense unless expressly so defined herein.

REFERENCES 1. (2018, May 2): BEST (Biomarkers, EndpointS, and other Tools) Resource—NCBI Bookshelf. Retrieved from https://www.ncbi.nlm.nih.gov/booksNBK326791/.
2. Abi-Dargham A, Horga G (2016): The search for imaging biomarkers in psychiatric disorders. Nature Medicine. 22: 1248-1255.
3. Alexander L, Gaskin P, Sawiak S J, Fryer T D, Hong Y T, Cockcroft G J, et al. (2018): Fractionating Blunted Reward Processing Characteristic of Anhedonia by Over-Activating Primate Subgenual Anterior Cingulate Cortex. Neuron. 101: 307-320.e6.
4. Anderson J S, Ferguson M A, Lopez-Larson M, Yurgelun-Todd D (2011): Reproducibility of Single-Subject Functional Connectivity Measurements. Am J Neuroradiol. 32: 548-555.
5. Beane J, Sebastiani P, Whitfield T H, Steiling K, Dumas Y-M, Lenburg M E, Spira A (2008): A Prediction Model for Lung Cancer Diagnosis that Integrates Genomic and Clinical Features. Cancer Prev Res. 1: 56-64.
6. Belleau E L, Taubitz L E, Larson C L (2015): Imbalance of default mode and regulatory networks during externally focused processing in depression. Soc Cogn Affect Neur. 10: 744-751.
7. Benjamini Y, Hochberg Y (1995): Controlling the False Discovery Rate: A Practical and Powerful Approach to Multiple Testing. J Royal Statistical Soc Ser B Methodol. 57: 289-300.
8. Breiman L (2001): Random Forests. Mach Learn. 45: 5-32.
9. Bzdok D, Meyer-Lindenberg A (2017): Machine Learning for Precision Psychiatry: Opportunities and Challenges. Biological Psychiatry Cognitive Neurosci Neuroimaging. doi: 10.1016/j.bpsc.2017.11.007.
10. Celikel F, Kose S, Cumurcu B, Erkorkmaz U, Sayar K, Borckardt J J, Cloninger R C (2009): Cloninger's temperament and character dimensions of personality in patients with major depressive disorder. Compr Psychiat. 50: 556-561.
11. Cenik B, Cenik C, Snyder M P, Brown S E (2017): Plasma sterols and depressive symptom severity in a population-based cohort. Plos One. 12: e0184382.

12. Chang L J, Gianaros P J, Manuck S B, Krishnan A, Wager T D (2015): A Sensitive and Specific Neural Signature for Picture-Induced Negative Affect. Plos Biol. 13: e1002180.
13. Chapman L J, Chapman J P, Raulin M L (1976): Scales for physical and social anhedonia. J Abnorm Psychol. 85: 374.
14. Chapman L J, Chapman J P, Raulin M L (1978): Body-image aberration in schizophrenia. J Abnorm Psychol. 87: 399.
15. Chase H W, Phillips M L (2016): Elucidating Neural Network Functional Connectivity Abnormalities in Bipolar Disorder: Toward a Harmonized Methodological Approach. Biological Psychiatry Cognitive Neurosci Neuroimaging. 1: 288-298.
16. Cloninger R C, Svrakic D M, Przybeck T R (1993): A Psychobiological Model of Temperament and Character. Arch Gen Psychiat. 50: 975-990.
17. Cole M W, Repovš G, Anticevic A (2014): The Frontoparietal Control System. Neurosci. 20: 652-664.
18. Consortium T, Anttila V, Bulik-Sullivan B, Finucane H K, Walters R K, Bras J, et al. (2018): Analysis of shared heritability in common disorders of the brain. Science. 360: eaap8757.
19. Cox R W (1996): AFNI: Software for Analysis and Visualization of Functional Magnetic Resonance Neuroimages. Comput Biomed Res. 29: 162-173.
20. Cui Z, Gong G (2018): The effect of machine learning regression algorithms and sample size on individualized behavioral prediction with functional connectivity features. Neuroimage. doi: 10.1016/j.neuroimage.2018.06.001.
21. Derogatis L R, Lipman R S, Rickels K, Uhlenhuth E, Covi L (1974): The Hopkins Symptom Checklist (HSCL). Mod Trends Psychiatry. 7: 79-110.
22. Desikan R S, Ségonne F, Fischl B, Quinn B T, Dickerson B C, Blacker D, et al. (2006): An automated labeling system for subdividing the human cerebral cortex on MRI scans into gyral based regions of interest. Neuroimage. 31: 968-980.
23. Dickman S J (1990): Functional and dysfunctional impulsivity: Personality and cognitive correlates. J Pers Soc Psychol. 58: 95.
24. Dubois J, Adolphs R (2016): Building a Science of Individual Differences from fMRI. Trends Cogn Sci. 20: 425-443.
25. Dubois J, Galdi P, Paul L K, Adolphs R (2018): A distributed brain network predicts general intelligence from resting-state human neuroimaging data. Phil Trans R Soc B. 373: 20170284.
26. Eckblad M, Chapman L J (1986): Development and validation of a scale for hypomanic personality. J Abnorm Psychol. 95: 214.
27. Elliott M L, Romer A, Knodt A R, Hariri A R (2018): A Connectome Wide Functional Signature of Transdiagnostic Risk for Mental Illness. Biol Psychiat. doi: 10.1016/j.biopsych.2018.03.012.
28. Eysenck S, Pearson P R, Easting G, Allsopp J F (1985): Age norms for impulsiveness, venturesomeness and empathy in adults. Pers Indiv Differ. 6: 613-619.
29. Fava M, Rush J A, Alpert J E, Balasubramani G, Wisniewski S R, Carmin C N, et al. (2008): Difference in Treatment Outcome in Outpatients With Anxious Versus Nonanxious Depression: A STAR*D Report. Am J Psychiat. 165: 342-351.
30. Fischer A S, Keller C J, Etkin A (2016): The Clinical Applicability of Functional Connectivity in Depression: Pathways Toward More Targeted Intervention. Biological Psychiatry Cognitive Neurosci Neuroimaging. 1: 262-270.
31. Fischl B, Dale A M (2000): Measuring the thickness of the human cerebral cortex from magnetic resonance images. Proc National Acad Sci. 97: 11050-11055.
32. Fischl B, Salat D H, Busa E, Albert M, Dieterich M, Haselgrove C, et al. (2002): Whole Brain Segmentation Automated Labeling of Neuroanatomical Structures in the Human Brain. Neuron. 33: 341-355.
33. Gao S, Calhoun V D, Sui J (2018): Machine learning in major depression: From classification to treatment outcome prediction. Cns Neurosci Ther. doi: 10.1111/cns.13048.
34. Gheiratmand M, Rish I, Cecchi G A, Brown M R, Greiner R, Polosecki P I, et al. (2017): Learning stable and predictive network-based patterns of schizophrenia and its clinical symptoms. Npj Schizophrenia. 3: 22.
35. Golden R R, Meehl P E (1979): Detection of the schizoid taxon with MMPI indicators. J Abnorm Psychol. 88: 217.
36. Goodkind M, Eickhoff S B, Oathes D J, Jiang Y, Chang A, Jones-Hagata L B, et al. (2015): Identification of a Common Neurobiological Substrate for Mental Illness. Jama Psychiatry. 72: 305-315.
37. Gordon E M, Laumann T O, Gilmore A W, Newbold D J, Greene D J, Berg J J, et al. (2017): Precision Functional Mapping of Individual Human Brains. Neuron. doi: 10.1016/j.neuron.2017.07.011.
38. Gotts S J, Simmons K W, Milbury L A, Wallace G L, Cox R W, Martin A (2012): Fractionation of social brain circuits in autism spectrum disorders. Brain. 135: 2711-2725.
39. Greicius M D, Flores B H, Menon V, Glover G H, Solvason H B, Kenna H, et al. (2007): Resting-State Functional Connectivity in Major Depression: Abnormally Increased Contributions from Subgenual Cingulate Cortex and Thalamus. Biol Psychiat. 62: 429-437.
40. Grisanzio K A, Goldstein-Piekarski A N, Wang M, Ahmed A P, Samara Z, Williams L M (2017): Transdiagnostic Symptom Clusters and Associations With Brain, Behavior, and Daily Function in Mood, Anxiety, and Trauma Disorders. Jama Psychiatry. doi: 10.1001/jamapsychiatry.2017.3951.
41. Hagele C, Schlagenhauf F, Rapp M, Sterzer P, Beck A, Bermpohl F, et al. (2015): Dimensional psychiatry: reward dysfunction and depressive mood across psychiatric disorders. Psychopharmacology. 232: 331-341.
42. Hastie T, Tibshirani R, Friedman J (2009): The elements of statistical learning: data mining, inference, and prediction, 2nd ed. Springer.
43. Insel T, Cuthbert B, Garvey M, Heinssen R, Pine D S, Quinn K, et al. (2010): Research Domain Criteria (RDoC): Toward a New Classification Framework for Research on Mental Disorders. Am J Psychiat. 167: 748-751.
44. Insel T R, Cuthbert B N (2015): Brain disorders? Precisely. Science. 348: 499-500.
45. Jo H, Saad Z S, Simmons K W, Milbury L A, Cox R W (2010): Mapping sources of correlation in resting state FMRI, with artifact detection and removal. Neuroimage. 52: 571-582.
46. Joyce D W, Kehagia A A, Tracy D K, Proctor J, Shergill S S (2017): Realising stratified psychiatry using multidimensional signatures and trajectories. J Transl Med. 15: 15.
47. Kaiser R H, Andrews-Hanna J R, Wager T D, Pizzagalli D A (2015): Large-Scale Network Dysfunction in Major Depressive Disorder: A Meta-analysis of Resting-State Functional Connectivity. Jama Psychiatry. 72: 603-611.
48. Kalousis A, Prados J, Hilario M (2007): Stability of feature selection algorithms: a study on high-dimensional spaces. Knowl Inf Syst. 12: 95-116.
49. KESSLER RC, ADLER L, MINNIE A, DEMLER O, FARAONE S, HIRIPI E, et al. (2005): The World Health Organization adult ADHD self-report scale (ASRS): a short screening scale for use in the general population. Psychol Med. 35: 245-256.
50. Kitchens S, Rosen L, Braaten E (1999): Differences in anger, aggression, depression, and anxiety between ADHD and non-ADHD children. J Atten Disord. 3: 77-83.
51. Kring A M (2008): Emotion disturbances as transdiagnostic processes in psychopathology. Handbook of emotion. 3.
52. Li W, Mai X, Liu C (2014): The default mode network and social understanding of others: what do brain connectivity studies tell us. Front Hum Neurosci. 8: 74.
53. Lo A, Chernoff H, Zheng T, Lo S-H (2015): Why significant variables aren't automatically good predictors. Proc National Acad Sci. 112: 13892-13897.
54. Mars R B, Neubert F-X, Noonan M P, Sallet J, Toni I, Rushworth M F (2012): On the relationship between the "default mode network" and the "social brain." Front Hum Neurosci. 6: 189.
55. Martino M, Magioncalda P, Huang Z, Conio B, Piaggio N, Duncan N W, et al. (2016): Contrasting variability patterns in the default mode and sensorimotor networks balance in bipolar depression and mania. Proc National Acad Sci. 113: 4824-4829.
56. Mateos-Pérez J, Dadar M, Lacalle-Aurioles M, Iturria-Medina Y, Zeighami Y, Evans A C (2018): Structural neuroimaging as clinical predictor: A review of machine learning applications. Neuroimage Clin. doi: 10.1016/j.nicl.2018.08.019.
57. Mayberg H S, Liotti M, Brannan S K, McGinnis S, Mahurin R K, Jerabek P A, et al. (1999): Reciprocal Limbic-Cortical Function and Negative Mood: Converging PET Findings in Depression and Normal Sadness. Am J Psychiat. 156: 675-682.
58. Mayberg H S, Lozano A M, Voon V, McNeely H E, Seminowicz D, Hamani C, et al. (2005): Deep Brain Stimulation for Treatment-Resistant Depression. Neuron. 45: 651-660.
59. McMakin D L, Olino T M, Porta G, Dietz L J, Emslie G, Clarke G, et al. (2012): Anhedonia Predicts Poorer Recovery Among Youth With Selective Serotonin Reuptake Inhibitor Treatment-Resistant Depression. J Am Acad Child Adolesc Psychiatry. 51: 404-411.
60. Menon V (2015): Brain Mapping. Syst. 597-611.
61. Nevins J R, Huang E S, Dressman H, Pittman J, Huang A T, West M (2003): Towards integrated clinico-genomic models for personalized medicine: combining gene expression signatures and clinical factors in breast cancer outcomes prediction. Hum Mol Genet. 12: R153-R157.
62. Noble S, Spann M N, Tokoglu F, Shen X, Constable R T, Scheinost D (2017): Influences on the Test-Retest Reliability of Functional Connectivity MM and its Relationship with Behavioral Utility. Cereb Cortex. 1-15.
63. Ohi K, Otowa T, Shimada M, Sasaki T, Tanii H (2019): Shared genetic etiology between anxiety disorders and psychiatric and related intermediate phenotypes. Psychol Med. 1-13.
64. Ojala M, Garriga G C (2010): Permutation Tests for Studying Classifier Performance. Journal of Machine Learning Research. 11: 1833-1863.
65. Öngür D, Farabaugh A, Iosifescu D V, Perlis R, Fava M (2005): Tridimensional Personality Questionnaire Factors in Major Depressive Disorder: Relationship to Anxiety Disorder Comorbidity and Age of Onset. Psychother Psychosom. 74: 173-178.
66. Osuch E, Gao S, Wammes M, Thèberge J, Willimason P, Neufeld R, et al. (2018): Complexity in mood disorder diagnosis: fMIRI connectivity networks predicted medication-class of response in complex patients. Acta Psychiat Scand. doi: 10.1111/acps.12945.
67. Patrick C J, Kramer M D (2017): Encyclopedia of Personality and Individual Differences. 1-5.
68. Patton J H, Stanford M S, Barratt E S (1995): Factor structure of the barratt impulsiveness scale. J Clin Psychol. 51: 768-774.
69. Peterson A, Thome J, Frewen P, Lanius R A (2013): Resting-State Neuroimaging Studies: A New Way of Identifying Differences and Similarities among the Anxiety Disorders? Can J Psychiatry. 59: 294-300.
70. Pittman J, Huang E, Dressman H, Horng C-F, Cheng S H, Tsou M-H, et al. (2004): Integrated modeling of clinical and gene expression information for personalized prediction of disease outcomes. P Natl Acad Sci Usa. 101: 8431-8436.
71. Poldrack R A, Congdon E, Triplett W, Gorgolewski K J, Karlsgodt K H, Mumford J A, et al. (2016): A phenome-wide examination of neural and cognitive function. Sci Data. 3: 160110.
72. Power J D, Barnes K A, Snyder A Z, Schlaggar B L, Petersen S E (2012): Spurious but systematic correlations in functional connectivity Mill networks arise from subject motion. Neuroimage. 59: 2142-2154.
73. Power J D, Cohen A L, Nelson S M, Wig G S, Barnes K, Church J A, et al. (2011): Functional Network Organization of the Human Brain. Neuron. 72: 665-678.
74. Power J D, Mitra A, Laumann T O, Snyder A Z, Schlaggar B L, Petersen S E (2014): Methods to detect, characterize, and remove motion artifact in resting state fMRI. Neuroimage. 84: 320-341.
75. Reddan M C, Lindquist M A, Wager T D (2017): Effect Size Estimation in Neuroimaging. Jama Psychiatry. doi: 10.1001/jamapsychiatry.2016.3356.
76. Saeys Y, Inza I, Larrañaga P (2007): A review of feature selection techniques in bioinformatics. Bioinformatics. 23: 2507-2517.
77. Satterthwaite T, Cook P, Bruce S, Conway C, Mikkelsen E, Satchell E, et al. (2015): Dimensional depression severity in women with major depression and post-traumatic stress disorder correlates with fronto-amygdalar hypoconnectivty. Mol Psychiatr. 21: 894-902.
78. Sharma A, Wolf D H, Ciric R, Kable J W, Moore T M, Vandekar S N, et al. (2017): Common Dimensional Reward Deficits Across Mood and Psychotic Disorders: A Connectome-Wide Association Study. Am J Psychiat. 174: 657-666.
79. Shen X, Finn E S, Scheinost D, Rosenberg M D, Chun M M, Papademetris X, Constable T R (2017): Using connectome-based predictive modeling to predict individual behavior from brain connectivity. Nat Protoc. 12: 506-518.
80. Spielberg J M, Beall E B, Hulvershorn L A, Altinay M, Karne H, Anand A (2016): Resting State Brain Network Disturbances Related to Hypomania and Depression in Medication-Free Bipolar Disorder. Neuropsychopharmacol. 41: 3016.
81. Sternat T, Fotinos K, Fine A, Epstein I, Katzman M A (2018): Low hedonic tone and attention-deficit hyperactivity disorder: risk factors for treatment resistance in depressed adults. Neuropsych Dis Treat. 14: 2379-2387.
82. Sylvester C M, Corbetta M, Raichle M E, Rodebaugh T L, Schlaggar B L, Sheline Y I, et al. (2012): Functional network dysfunction in anxiety and anxiety disorders. Trends Neurosci. 35: 527-535.
83. The Temperament and Character Inventory (TCI): A Guide to Its Development and Use (n.d.).
84. Tibshirani R (1996): Regression shrinkage and selection via the lasso. Journal of the Royal Statistical Society, Series B. 58: 267-288.
85. Uher R, Perlis R, Henigsberg N, Zobel A, Rietschel M, Mors O, et al. (2011): Depression symptom dimensions as predictors of antidepressant treatment outcome: replicable evidence for interest-activity symptoms. Psychol Med. 42: 967-980.
86. Wall D, Kosmicki J, DeLuca T, Harstad E, Fusaro V (2012): Use of machine learning to shorten observation-based screening and diagnosis of autism. Transl Psychiat. 2: e100.
87. Webb C A, Trivedi M H, Cohen Z D, Dillon D G, Fournier J C, Goer F, et al. (2018): Personalized prediction of antidepressant v. placebo response: evidence from the EMBARC study. Psychol Med. 1-10.
88. Whitton A E, Treadway M T, Pizzagalli D A (2015): Reward processing dysfunction in major depression, bipolar disorder and schizophrenia. Curr Opin Psychiatr. 28: 7.
89. Williams L M (2016): Precision psychiatry: a neural circuit taxonomy for depression and anxiety. Lancet Psychiatry. 3: 472-480.
90. Williams L M (2017): Defining biotypes for depression and anxiety based on large-scale circuit dysfunction: a theoretical review of the evidence and future directions for clinical translation. Depress Anxiety. 34: 9-24.
91. Xia C, Ma Z, Ciric R, Gu S, Betzel R F, Kaczkurkin A N, et al. (2018): Linked dimensions of psychopathology and connectivity in functional brain networks. Nat Commun. 9: 3003.
92. Yang G J, Murray J D, Repovs G, Cole M W, Savic A, Glasser M F, et al. (2014): Altered global brain signal in schizophrenia. Proc National Acad Sci. 111: 7438-7443.
93. Yang Y, Zhong N, Imamura K, Lu S, Li M, Zhou H, et al. (2016): Task and Resting-State fMRI Reveal Altered Salience Responses to Positive Stimuli in Patients with Major Depressive Disorder. Plos One. 11: e0155092.
94. Yang Z, Gu S, Honnorat N, Linn K A, Shinohara R T, Aselcioglu I, et al. (2018): Network changes associated with transdiagnostic depressive symptom improvement following cognitive behavioral therapy in MDD and PTSD. Mol Psychiatr. 1-10.
95. Yarkoni T, Westfall J (2017): Choosing Prediction Over Explanation in Psychology: Lessons From Machine Learning. Perspect Psychol Sci. 12: 1100-1122.
96. Yuen L D, Miller S, Wang P W, Hooshmand F, Holtzman J N, Goffin K C, et al. (2016): Current irritability robustly related to current and prior anxiety in bipolar disorder. J Psychiatr Res. 79: 101-107.
97. Zhang W-N, Chang S-H, Guo L-Y, Zhang K-L, Wang J (2013): The neural correlates of reward-related processing in major depressive disorder: A meta-analysis of functional magnetic resonance imaging studies. J Affect Disorders. 151: 531-539.
98. Zou H, Hastie T (2005): Regularization and variable selection via the elastic net. J Royal Statistical Soc Ser B Statistical Methodol. 67: 301-320.

What is claimed is:

1. A system for evaluating mental health of a patient, the system comprising:
  a display device;
  a user interface;
  a memory containing machine readable medium comprising machine executable code having stored thereon instructions for performing a method;
  a control system coupled to the memory comprising one or more processors, the control system configured to execute the machine executable code to cause the control system to:
    receive, from the user interface, a selection of answers corresponding to each question in a series of questions from mental health questionnaires;
    receive, unprocessed MRI data corresponding to a set of MRI images of a biological structure;
    process, using a machine learning model, the selection of answers, and the unprocessed MRI data to output a symptom severity indicator for a mental health category of the patient,
  wherein the machine learning model was generated by:
    receiving labeled training data for a plurality of individuals indicating whether each of the plurality of individuals has one or more mental health disorders and a severity of symptoms corresponding to the one or more mental health disorders, the labeled training data comprising:
      MRI data recorded for each of the plurality of individuals;
      a selection of answers to the series of questions for each of the plurality of individuals;
    determining a plurality of features from the labeled training data;
    training an initial machine learning model in a supervised manner, based on the plurality of features;
    extracting importance measures for each of the plurality of features, based on the training of the initial machine learning model;
    generating a plurality of subset machine learning models based on the extracted importance measures for the plurality of features;
    evaluating a classification performance of the generated plurality of subset machine learning models; and
    selecting at least one of the subset machine learning models as the machine learning model.

2. The system of claim 1, wherein the machine learning model is trained on clinical scales data corresponding to the plurality of individuals.

3. The system of claim 1, wherein the machine learning model is trained on fMRI full connectivity data corresponding to the plurality of individuals.

4. The system of claim 1, wherein the machine learning model is trained on sMRI data corresponding to the plurality of individuals, the sMRI data comprising cortical volume data, cortical thickness data, and cortical surface area data.

5. The system of claim 1, wherein the machine learning model is trained on input data corresponding to the plurality of individuals, wherein, for each individual, the input data comprises clinical scales data and fMRI data.

6. The system of claim 1, wherein the machine learning model is trained on input data corresponding to the plurality of individuals, wherein, for each individual, the input data comprises clinical scales data and sMRI data.

7. The system of claim 1, wherein the machine learning model is trained on input data corresponding to the plurality of individuals, wherein, for each individual, the input data comprises fMRI data and sMRI data.

8. The system of claim 1, wherein the machine learning model is trained on input data corresponding to the plurality of individuals, wherein, for each individual, the input data comprises fMRI data, clinical scales data, and sMRI data.

* * * * *